United States Patent
Polacek et al.

(10) Patent No.: US 11,389,525 B2
(45) Date of Patent: Jul. 19, 2022

(54) POLYGENE INFLUENZA VACCINE

(71) Applicant: Statens Serum Institut, Copenhagen (DK)

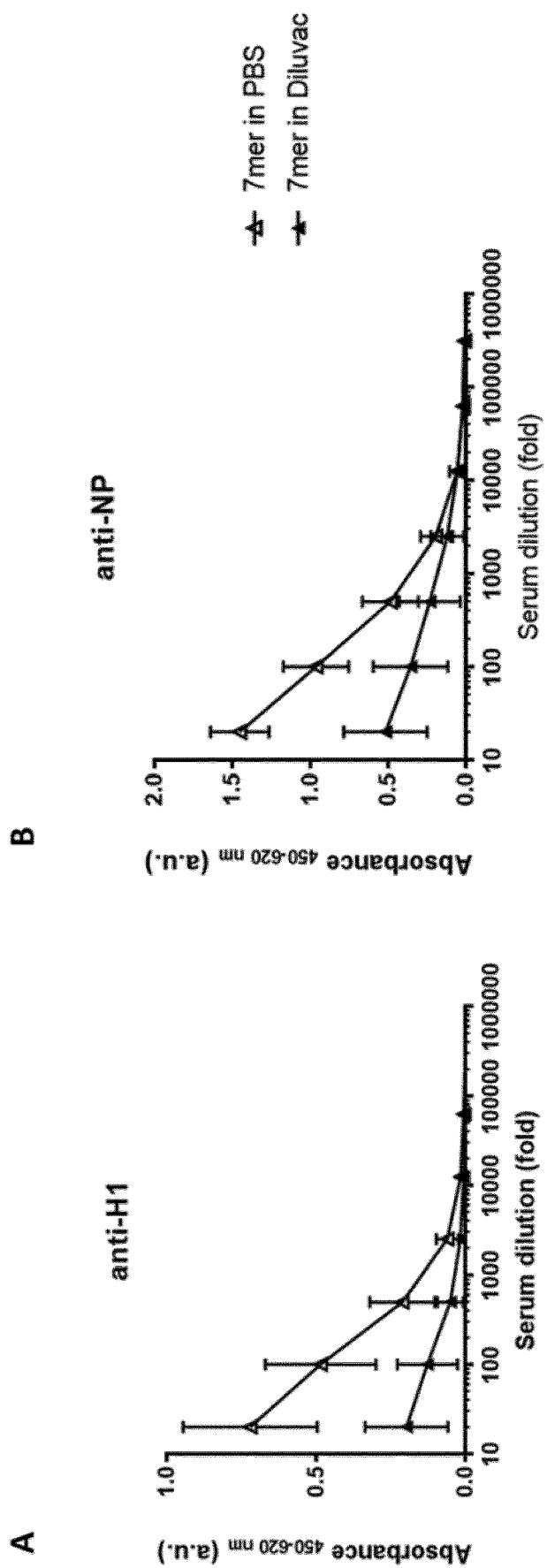
Fig. 6A-B

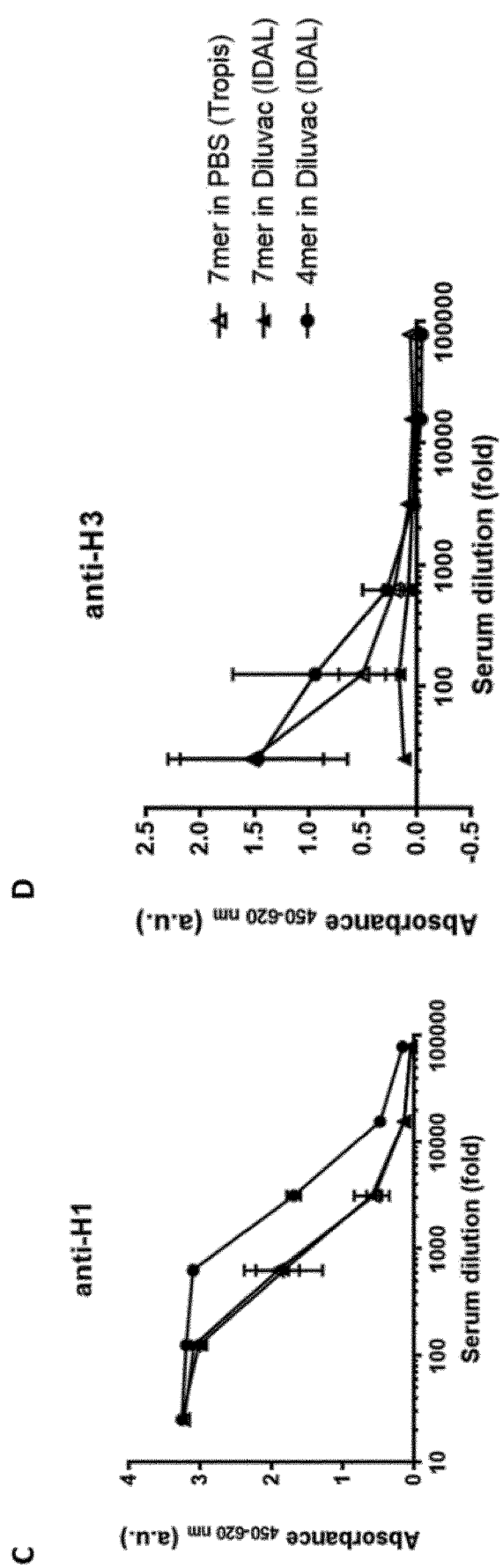
Fig. 6C-D

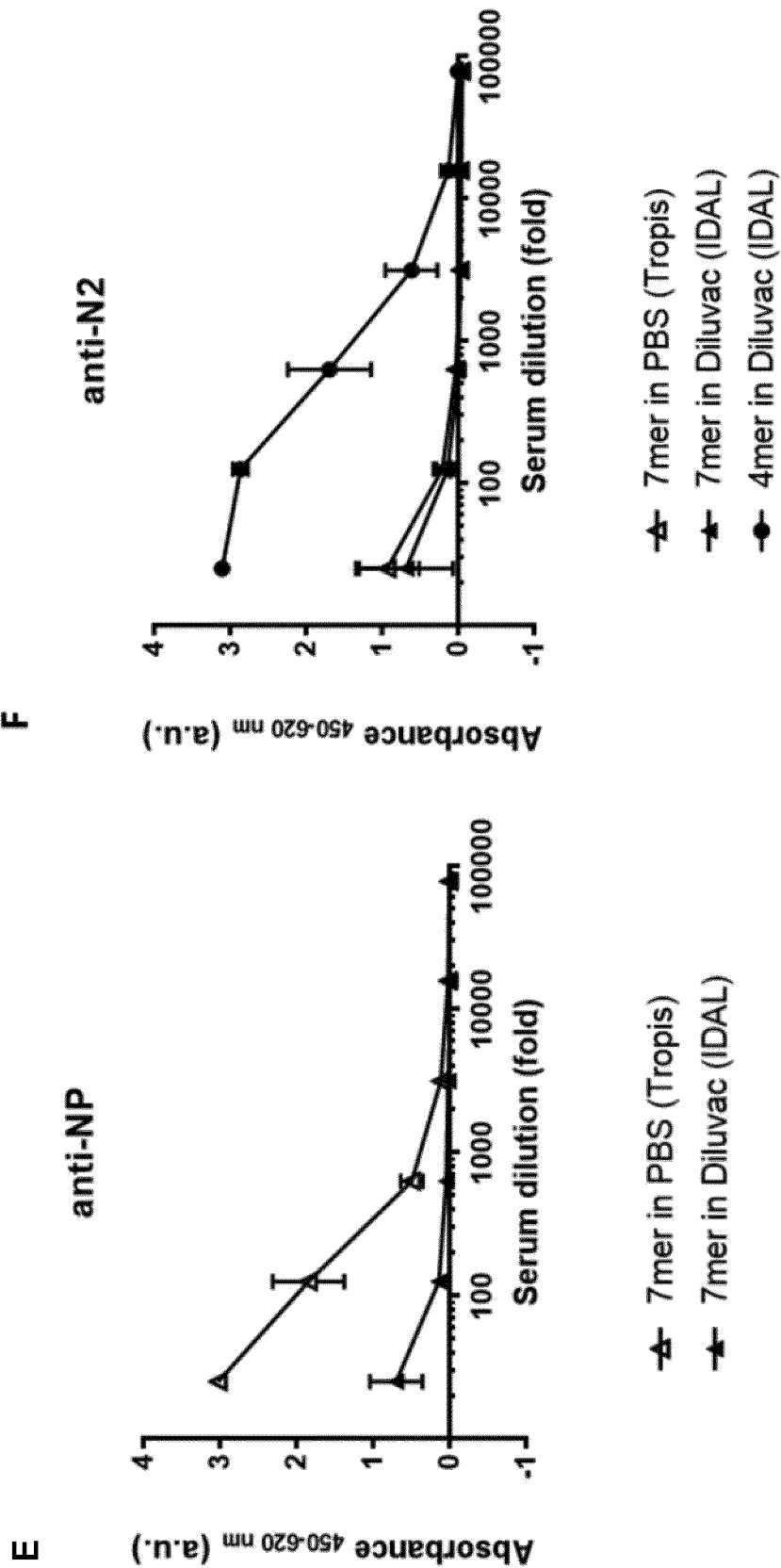
Fig. 6E-F

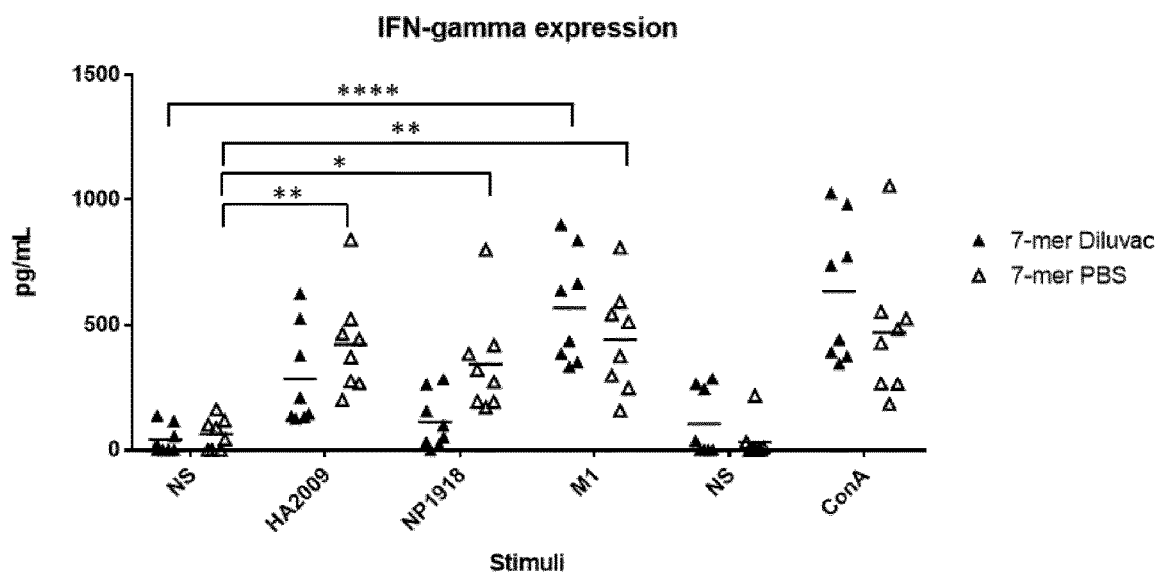
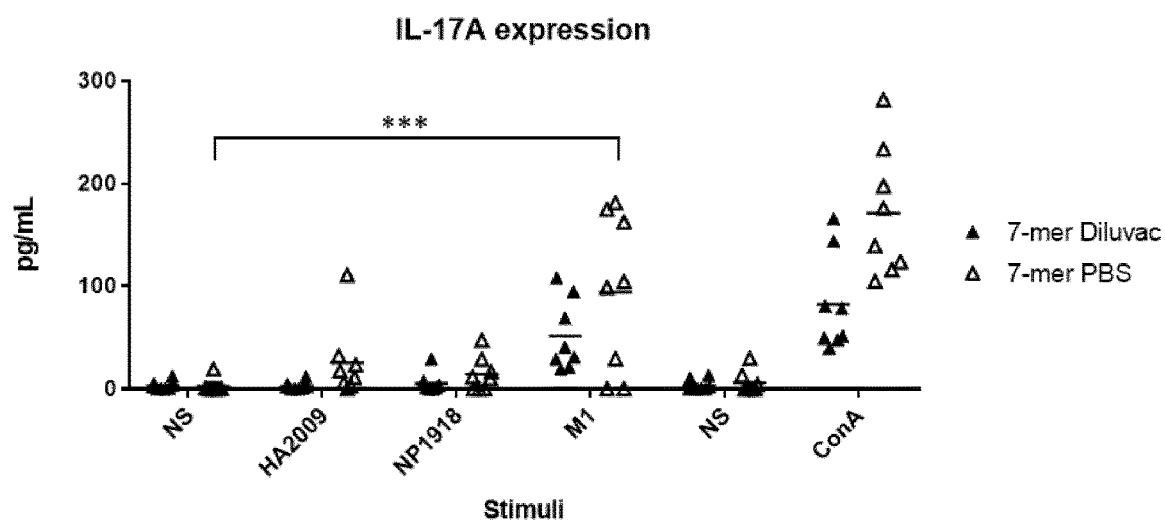
Fig. 7A-B

POLYGENE INFLUENZA VACCINE

INCORPORATION-BY-REFERENCE OF MATERIAL SUBMITTED IN ELECTRONIC FORM

Incorporation herein by reference in its entirety is the sequence listing submitted via EFS-Web as a text file named SEQLIST.txt, created Feb. 3, 2022, and having a size of 94,460 bytes.

TECHNICAL FIELD OF THE INVENTION

The present invention relates to a nucleic acid vaccine. Specifically, the use of a single nucleic acid sequence comprising combinations of influenza genes coding for selected hemagglutinin (HA), neuraminidase (NA), matrix protein 1 (M1), matrix protein 2 (M2) and nucleoprotein (NP) interspaced with selected linkers comprising cleavage sites to produce individual proteins, together forming one polyvalent influenza vaccine for use in medicine for humans and animals.

BACKGROUND OF THE INVENTION

Vaccination is the preferred choice for influenza prophylaxis. Inactivated influenza virus vaccines are licensed worldwide while cold-adapted live vaccines are licensed only in Russia and the USA. The most common prophylaxis of annual influenza infections is vaccination with inactivated protein vaccines from influenza A virus propagated in hens' eggs or cell lines. Thus, the common vaccines are the inactivated vaccine viruses, which are propagated in hens' eggs or cell lines and inactivated e.g. by formaldehyde or β-propiolactone. There are three main classes of inactivated vaccines; whole virus, protein split (chemically disrupted with ether or tributyl phosphate) and protein subunit (purified surface glycoproteins), administrated intramuscularly or subcutaneously. Whole, inactivated influenza vaccine is not widely used due to varying protective effect and high levels of side effects and adverse reactions. The seasonal influenza vaccine (split and subunit) for humans is trivalent or tetravalent, comprising an H3N2 and an H1N1 influenza A virus strain and one or two influenza B virus strains. The normal human vaccine dose is standardised to 15 µg HA protein of each virus component administrated once in normal healthy adults and twice in children and persons with no pre-existing influenza A immunity. The conventional vaccines induce merely a humoral immune response and are strain specific. These vaccines provide limited protection in case of antigen mismatch, when the circulating virus strains and the vaccine differ. The protective effect of the traditional protein split vaccine is therefore very limited with little or no cross-protection to influenza A virus variants. Because of the continuous evolution of influenza A virus strains, the high mutation rate in HA and NA and the type-specific antibodies induced by the conventional vaccines, a new vaccine has to be produced every year based on the most recent circulating influenza A strain. Even the efficacy of live attenuated influenza vaccines are affected by the extent of antigenic similarity between the vaccine strain and the circulating virus strains as well as the age of the vaccines. Several vaccine improvements are necessary in case of a new emerging human influenza A strain. Virus vaccine production in cell lines in vitro is a relatively slow process with relatively low yields which is suboptimal when high amounts of vaccine is needed, and the vaccine strain has first to be designed and adapted for growth in cells. In the case of emerging strains, egg adaptation and production of a certain influenza virus strain is too slow (6-12 months). If this strain is also a highly pathogenic avian influenza (HPAI) virus, egg production in fertilized eggs might be impossible, because the virus kills the egg embryo. In addition, the availability of eggs might be limited during outbreaks of avian influenza among birds, thus slowing down the vaccine production even further. In terms of populations with no pre-existing immunity, two vaccinations would be necessary, thereby further burdening the vaccine production. Even if there is no new pandemic influenza A circulating among humans, and only spread of HPAI among poultry, the shortage of eggs will limit the production of traditional seasonal influenza vaccines in eggs. In addition, traditional influenza protein vaccines do not have optimal protection as prophylaxis and lack therapeutic effect. Thus, there is a great need for alternative influenza vaccines with more "universal" or broad-range protection and easier and faster production free of egg proteins.

Although DNA vaccines were developed more than 20 years ago, clinical trials preceding stage I and II in humans are rare. Currently, about one hundred stage I and II clinical trials for DNA vaccines in humans are being conducted. However, three prophylactic veterinary DNA vaccines, have been licensed: one for West Nile Virus (in horses) and a second for Infectious Hematopoietic Necrosis virus in Salmon, and an immunotherapeutic vaccine for cancer in dogs. A forth DNA plasmid construct is licensed as a growth hormone therapy for pigs (production animals). This demonstrates that DNA vaccines can have good and protective effects and that new DNA vaccines are not limited by the size of the animal or species. The great success with DNA vaccines observed for the murine model for the first generation of DNA vaccines did initially not translate well to humans.

However, the field has moved significantly forward through improvements of gene expression, the vaccine gene constructs, the vector backbones, use of adjuvants, the delivery methods, the vaccine modality such as different prime-boost strategies, DNA dose and vaccine intervals, and have together made the nucleotide vaccines highly clinically relevant. Researchers have recently demonstrated protective antibodies levels by a single dose of gene gun administrated HA DNA vaccine to humans. "Nucleic acid immunization", which is a more correct term since both naked DNA and RNA can be used, or the commonly preferred name "DNA vaccine", is the inoculation of antigen-encoding DNA or RNA as either synthetic genes or incorporated into various expression cassettes or vectors in order to induce immunity to the gene product. The genes may instead be incorporated into viral vectors with the purpose of inducing immunity to the gene product. Thus, in the present definition of a "DNA vaccine" is meant a nucleotide vaccine, which includes all kinds of delivery systems for the antigen encoding DNA or RNA. The vaccine gene of interest can be in the form of a naked circular plasmid or linear expression cassette with only the key features necessary for expression (e.g. promotor, gene of interest and polyadenylation signal) from a DNA or RNA. Delivery systems may most often be naked DNA in buffer with or without adjuvant, DNA coupled to nanoparticles and/or formulated into adjuvant containing compounds or inserted into live bacterial or viral vectors such as Adenovirus, adeno-associated virus (AAV), alphavirus, poxvirus and herpes virus.

Nucleic-acid vaccines based on synthetic RNA encoding the gene of interest are also possible either as a conventional, non-amplifying mRNA or as a so called self-amplifying mRNA). The self-amplifying mRNAs can be derived from modified alphavirus single-stranded RNA genome that are expressed in the host cells with the additional intrinsic innate immune stimulating capabilities. Self-amplifying RNA (saRNA) can even be inserted into a circular plasmid as a DNA vaccine that upon injection can generate multiple RNA copies inside the transfected cell. The mRNA nucleic acid vaccine can be delivered separately or formulated e.g. with emulsions with or without adjuvants or as lipid nanoparticles. Alpha-tocopherol based adjuvant for nucleic acid vaccines has previously been disclosed in WO2016041562.

Previously, DNA and RNA vaccines against influenza A virus with a broad protection against homologous and heterologous influenza A viruses have been developed, i.e. challenge in animals with common circulating strains belonging to H1N1 and to H3N2 types with and without adjuvants. WO2008145129 and WO2010060430 disclose the use of pandemic influenza A genes to produce nucleotide vaccines to induce immune responses able to cross-react and cross-protect against drifted virus variants and even heterologous strains and heterotypic strains like the highly pathogenic H5N1 in ferrets. These nucleotide vaccines can be used for both annual seasonal influenza A vaccine development as well as vaccines in the case of emerging new influenza A strains. The broad protective DNA/RNA vaccines disclosed in WO2008145129 and WO2010060430, comprising selected influenza A genes, can also protect pigs from circulating swine influenza A virus strains including the wide spread H1N1 pdm strain. Thus, influenza A DNA vaccine has been found to be very immunogenic in pigs and able to induce protection against shedding and disease in pigs after various influenza A virus challenge.

A major disadvantage with these vaccines is that the production is complicated and expensive due to the need for separate manufacturing of the several individual nucleic acid components (plasmids) i.e. as individual DNA plasmid components comprising the nucleic acid influenza A virus vaccine.

Hence, an improved method for production of nucleotide vaccines and provision of such nucleotide vaccines would be advantageous. In particular, a more efficient and/or less expensive method for providing nucleotide vaccines comprising multiple antigen-encoding nucleic acids would be advantageous.

SUMMARY OF THE INVENTION

Thus, an object of the present invention relates to the provision of an efficient method for providing nucleotide vaccines comprising multiple antigen-encoding nucleic acids.

In particular, it is an object of the present invention to provide a nucleotide influenza vaccine comprising a single nucleic acid sequence encoding several selected influenza proteins, with various modifications, interspaced with selected cleavage-inducing linkers, thus enabling the expression of separate influenza proteins from one single open reading frame, both in vitro and in vivo.

Thus, one aspect of the invention relates to a nucleotide sequence comprising one or more influenza genes encoding haemagglutinin (HA) and one or more influenza genes encoding neuraminidase (NA), said influenza genes being connected by linkers each comprising at least one cleavage site.

Another aspect of the present invention relates to a nucleotide vaccine comprising a nucleotide sequence as described herein.

Yet another aspect of the present invention relates to the provision of a nucleotide sequence or a nucleotide vaccine as described herein for use in the prevention of influenza infection.

Still another aspect of the present invention is to provide a kit comprising:
(i) an effective amount of a nucleotide sequence as described herein, or
(ii) an effective amount of a nucleotide vaccine as described herein, and
(ii) optionally, instructions for use.

A further aspect of the present invention relates to a method for producing a nucleotide vaccine comprising multiple antigen-encoding nucleic acids, said method comprising the following steps:
(i) providing a nucleotide sequence of at least two genes encoding antigenic peptides, wherein said at least two genes are connected by linkers comprising at least one cleavage site, and
(ii) mixing said nucleotide sequence with a pharmaceutical acceptable diluent, excipient and/or adjuvant, thereby providing a nucleotide vaccine.

BRIEF DESCRIPTION OF THE FIGURES

FIG. 6 shows antibody responses in mice and rabbits vaccinated with nucleotide vaccine. Antibody response for (A) anti-H1 and (B) anti-NP in mice vaccinated with 7mer in PBS or in Diluvac Forte. Antibody response (C) anti-H1, (D) anti-H3, (E) anti-NP and (F) anti-N2 in rabbits vaccinated with 7mer in PBS, or 4mer or 7mer in Diluvac Forte.

FIG. 7 shows cytokine responses in isolated immune cells from polygene DNA vaccinated mice. Mice were vaccinated with 7mer in PBS of Diluvac Forte and splenocytes isolated from the mice were stimulated with a panel of influenza proteins and analysed in a cytokine-ELISA specific for (A) IFN-gamma, or (B) IL-17A.

DETAILED DESCRIPTION OF THE INVENTION

Definitions

Figure 1:
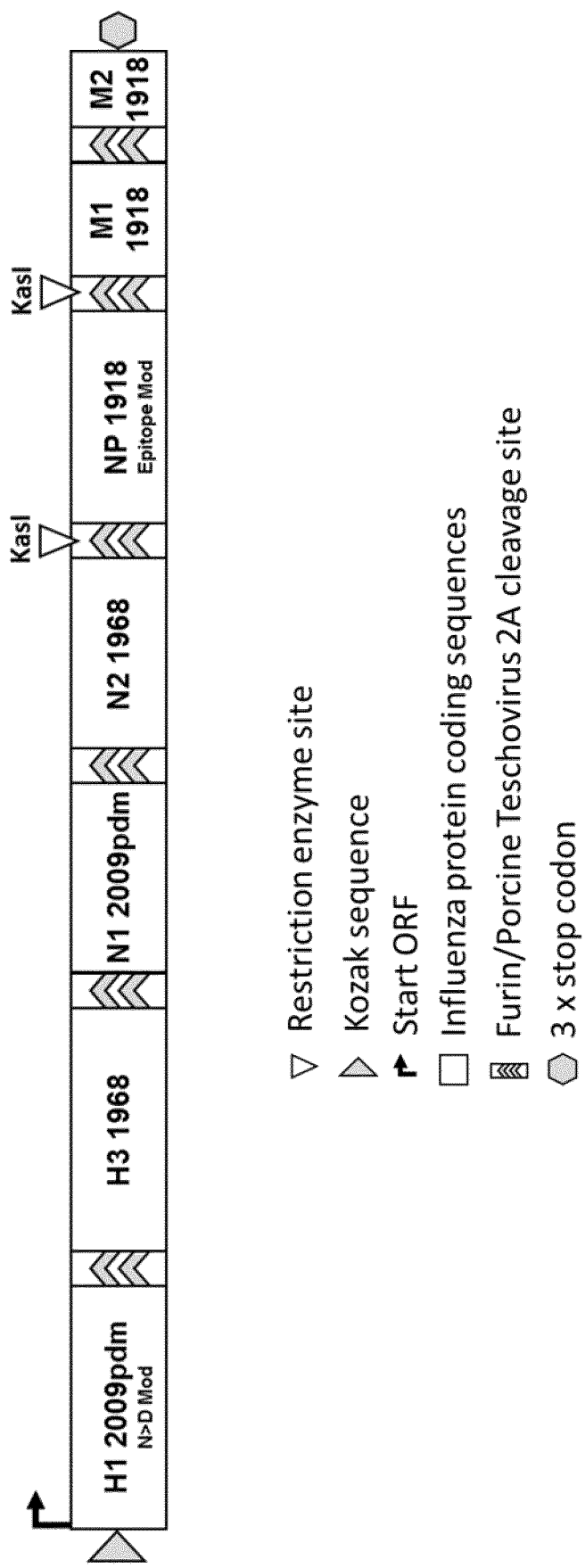
FIG. 1 shows an overview of the polygene influenza vaccine. The polygene, or single nucleic acid, construct express 7 different selected influenza A virus proteins (HA (H1 and H3), NA (N1 and N2), NP, M1 and M2), interspaced with cleavage sites for furin and porcine teschovirus-1 2A (P2A), here referred to as 7mer. The possibility to exchange or remove an influenza coding region is exemplified here by the alternative furin/P2A linkers flanking the coding sequence for NP, which are modified to harbor one KasI site each. One single codon in H1 and one epitope region in NP are modified to minimize the potential risk for narcolepsy in certain humans.

Prior to discussing the present invention in further details, the following terms and conventions will first be defined:

Nucleotide Sequence

In the present context, the term "nucleotide sequence" refers to a polymer of nucleotides comprising nucleotides A,C,T,U,G, or other naturally occurring nucleotides or artificial nucleotide analogues. Thus, nucleotide sequences may be comprised of e.g. DNA or RNA. In the present context, nucleotide sequences may comprise multiple genes of any origin, but preferably originating from Orthomyxoviridae, including *Influenzae* A-D virus. The genes encompassed by the nucleotide sequences are separated by cleavable linkers.

Haemagglutinin

In the present context, the term "haemagglutinin" (HA) refers to the glycoprotein found on the surface of influenza viruses. HA is involved in host cell binding, internalization and particle formation of influenza virus. HA is found in at least 18 subtypes that may be used to categorize different variants of Influenza virus. Thus, as used herein, e.g. "H1" denotes haemagglutinin subtype 1, "H5" denotes haemagglutinin subtype 5, and so forth.

Neuraminidase

In the present context, the term "neuraminidase" (NA) refers to the enzyme found on the surface of influenza viruses. NA removes sialic acid from glycoproteins to avoid virus particle aggregation and promotes viral release from the host cell. NA is found at least 11 subtypes that may be used to categorize different variants of Influenza virus. Thus, as used herein, e.g. "N1" denotes neuraminidase subtype 1, "N3" denotes neuraminidase subtype 3, and so forth.

Together, haemagglutinin and neuraminidase may therefore be used to characterize different variants of influenza virus, such as H1N1 (haemagglutinin subtype 1, neuraminidase subtype 1).

Variants

In the present context, the term "variant" refers to a nucleic acid sequence or polypeptide comprising a sequence, which differs (by deletion, insertion, and/or substitution of an nucleic acid or amino acid) in one or more nucleic acid or amino acid positions from that of a wild type nucleic acid or polypeptide sequence.

Linker

In the present context, the term "linker" refers to a connection between two protein coding sequences or their protein products. Linkers comprise a stretch of contiguous nucleic acids or amino acids, which holds at least one cleavage site that enables separation of the genes or their products through cleavage of the linker. Preferably, the linker comprise a cleavage site at its 5' end and a cleavage site at its 3' end, or a cleavage site at its N-terminal end and a cleavage site at its C-terminal end.

Cleavage Site

In the present context, the term "cleavage site" refers to a nucleic acid or amino acid motif, which may trigger cleavage of a nucleotide sequence or amino acid sequence. The cleavage may be performed by a variety of mechanisms including, but not limited to, enzymatic cleavage and self-cleavage activity. Thus, a cleavage site may be utilized to divide a nucleotide sequence or amino acid sequence into smaller fragments, e.g. individual genes or peptides.

Polygenic and Polycistronic

In the present context, the term "polygenic" and "polycistronic" gene refers to single DNA and RNA sequences, respectively, that encodes multiple different peptides or proteins. Thus, the nucleotide sequence comprising multiple antigen-encoding peptides or proteins as described herein, may be either polygenic or polycistronic.

Influenza Genes

In the present context, the term "influenza genes" refers to any protein coding sequence originating form an influenza virus and which may express an immunogenic peptide or protein relevant for preparation of a nucleotide vaccine.

Influenza Infection

In the present context, the term "influenza infection" refers to an acute viral infection by an influenza virus. Influenza infection may cause symptoms, such as fever, chills and muscle pain.

Codon Optimization

In the present context, the term "codon optimization" refers to changing the codons of a nucleotide sequence without altering the amino acid sequence that it encodes in order to favour expression in a specific species. Codon optimization may be used to increase the abundance of the peptide or protein that the nucleotide sequence encodes since "rare" codons are removed and replaced with abundant codons.

In the present context, the nucleotide sequences as described herein may be codon optimized specifically for expression in humans.

Expression Vector

In the present context, the term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression systems. Expression vectors include all those known in the art, such as cosmids, plasmids (e.g., naked or contained in liposomes) and viruses or viral vectors that incorporate the recombinant polynucleotide.

Operatively Linked

In the present context, the term "operatively linked" refers to the connection of elements being a part of a functional unit such as a gene, a protein coding sequence or an open reading frame. Accordingly, by operatively linking a promoter to a nucleic acid sequence encoding a polypeptide, the two elements becomes part of a functional unit. The linking of the expression control sequence (promoter) to the nucleic acid sequence enables the transcription of the nucleic acid sequence directed by the promoter. By operatively linking two heterologous nucleic acid sequences encoding a polypeptide, the sequences becomes part of the functional unit—an open reading frame encoding a fusion protein comprising the amino acid sequences encoded by the heterologous nucleic acid sequences. Homologous nucleic acid sequences may be operatively linked in a similar manner.

Vaccine and Nucleotide Vaccine

In the present context, the term "vaccine" refers to a composition intended to induce immunity to a disease. A vaccine functions by exposing the immune system to antigenic peptides or proteins. One type of vaccines are "nucleotide vaccines" that functions by inoculation of antigen-encoding DNA or RNA as either synthetic genes or incorporated into various expression cassettes or vectors in order to induce immunity to the gene product. Thus, a nucleotide vaccine may comprise a nucleotide sequence composed of either DNA or RNA. The nucleotide vaccine may include any type of delivery system for the antigen-encoding DNA or RNA, including, but not limited to, plasmids, expression cassettes, adjuvants, particles, and bacterial or viral vectors.

Immunogenic

In the present context, the term "immunogenic" refers to the ability of an antigenic peptide or protein to elicit an immune response that induce protective immunity to the antigenic peptide or protein over time. Thus, an immunogenic peptide or protein may be used as antigen in a vaccine.

Pharmaceutically Acceptable

In the present context, the term "pharmaceutically acceptable" refers to a vaccine that is physiologically tolerable and do not typically produce an unintended allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

Adjuvant

In the present context, the term "adjuvant" refers to a compound or mixture that enhances the immune response to an antigen. An adjuvant can serve as a tissue depot that slowly releases the antigen and as a lymphoid system activator, which non-specifically enhances the immune response. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, DL-α-tocopherol and potentially useful human adjuvants such as BCG (bacille Calmette-Guerin) and *Corynebacterium parvum*. *Preferably, the adjuvant is pharmaceutically acceptable.*

Excipient

In the present context, the term "excipient" refers to a diluent, adjuvant, carrier, or vehicle with which the composition of the invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Effective Amount

In the present context, the term "effective amount" refers to a dosage or amount sufficient to produce a desired effect. The desired effect may comprise an objective or subjective improvement in the recipient of the dosage or amount, such as preventive protection of an individual against infection.

Prophylactic/Preventive Treatment

In the present context, the term "prophylactic treatment" refers to a treatment administered to an individual who does not display signs or symptoms of a disease, pathology, or infection, or displays only early signs or symptoms of a disease, pathology, or infection, such that treatment is administered for the purpose of diminishing, preventing, or decreasing the risk of developing the disease, pathology, or infection. A prophylactic treatment functions as a preventative treatment against a disease or infection, and therefore the terms "prophylactic treatment" and "preventive treatment" are used interchangeably herein.

Sequence Identity

In the present context, the term "sequence identity" is here defined as the sequence identity between genes or proteins at the nucleotide, base or amino acid level, respectively. Specifically, a DNA and a RNA sequence are considered identical if the transcript of the DNA sequence can be transcribed to the corresponding RNA sequence.

Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical in that position. The percent identity between the two sequences is a function of the number of identical positions shared by the sequences (i.e., % identity=# of identical positions/total # of positions (e.g., overlapping positions)×100). In one embodiment, the two sequences are the same length.

In another embodiment, the two sequences are of different length and gaps are seen as different positions. One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecule of the invention. BLAST protein searches may be performed with the XBLAST program, score=50, wordlength=3 to obtain amino acid sequences homologous to a protein molecule of the invention.

To obtain gapped alignments for comparison purposes, Gapped BLAST may be utilized. Alternatively, PSI-Blast may be used to perform an iterated search, which detects distant relationships between molecules. When utilising the NBLAST, XBLAST, and Gapped BLAST programs, the default parameters of the respective programs may be used.

See http://www_ncbi_nim_nih_gov. Alternatively, sequence identity may be calculated after the sequences have been aligned e.g. by the BLAST program in the EMBL database (www_ncbi_nlm_nih_gov/cgi-bin/BLAST).

Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted. An embodiment of the present invention thus relates to sequences of the present invention that has some degree of sequence variation.

The invention will now be described in more details.

The present invention discloses nucleotide sequence constructs comprising the influenza genes coding for selected hemagglutinins (HA) and neuraminidases (NA) fused together with a linker comprising at least one cleavage site. The nucleotide constructs can additionally comprise influenza genes coding for matrix protein 1 (M1) and matrix protein 2 (M2) and nucleoprotein (NP), interspaced or fused together with linkers comprising at least one protein cleavage site, and where the genes preferably stem from a pandemic influenza strain as depicted in FIG. 1. The nucleotides of this polygene construct are either DNA or RNA.

The nucleotide sequence comprising multiple antigen-encoding influenza genes may, upon administration to a subject, such as a human or animal, be expressed as a single polypeptide or polyprotein in vivo in the recipient of the nucleotide sequence. Subsequent to expression, the individual gene products are separated via intracellular cleavage of the polypeptide or polyprotein at the designed cleavage sites. Thus, the strategy described herein takes advantage of the cellular machinery of the recipient to process the nucleotide sequence into final antigenic peptides or proteins.

An advantage of the described strategy is the reduced time consumption of producing the vaccine as only a single nucleotide sequence construct must be produced and introduced in a single "vaccine-plasmid" for GMP production and QA. The alternative of producing the individual gene constructs separately, such as seven individual constructs, which is subsequently mixed, is not only a more complex solution with higher risks of error, but also a less attractive economic solution.

Another advantage of the described strategy is that the nucleotide sequence described herein is expressed in equimolar ratios of the separate genes, which negates the risk of variable expression of multiple individual constructs caused by inter-gene competition between a mixture of plasmids. An additional concern with mixtures of plasmids is whether all cells receive and get exposed to all antigens. Such concerns are redundant for the nucleotide sequence construct described herein. Thus, the nucleotide sequence comprising multiple antigen-encoding influenza genes as described herein will benefit from enhanced vaccine effect and fewer QA concerns.

A further advantage achieved by the present invention is that the recipient of the nucleotide vaccine as described herein only has to receive the vaccination regimen once to obtain sustained protection against a broad spectrum of influenza strains. Thus, there is no need for the recipient to receive repeated annual influenza vaccinations as is the standard today. This will lower the cost of influenza vaccination programs.

Thus, a first aspect of the present invention relates to a nucleotide sequence comprising one or more influenza genes encoding haemagglutinin (HA) and one or more influenza genes encoding neuraminidase (NA), said influenza genes being connected by linkers each comprising at least one cleavage site.

Historically, the influenza virus is evolving fast and it is an eternal challenge to keep up with new variants of known epidemic influenza strains. Variants of influenza strains arise not only from mutations of viral antigens, but also from combinations of antigens. Thus, the nucleotide sequence as described herein may comprise a variety of different combinations of HA and NA.

Therefore, an embodiment of the present invention relates to the nucleotide sequence as described herein, wherein the one or more influenza genes encoding haemagglutinin (HA) are selected from the group consisting of subtypes H1-H18 and variants thereof.

Another embodiment of the present invention relates to the nucleotide sequence as described herein, wherein the one or more influenza genes encoding neuraminidase (NA) are selected from the group consisting of subtypes N1-N11 and variants thereof.

Figure 2:
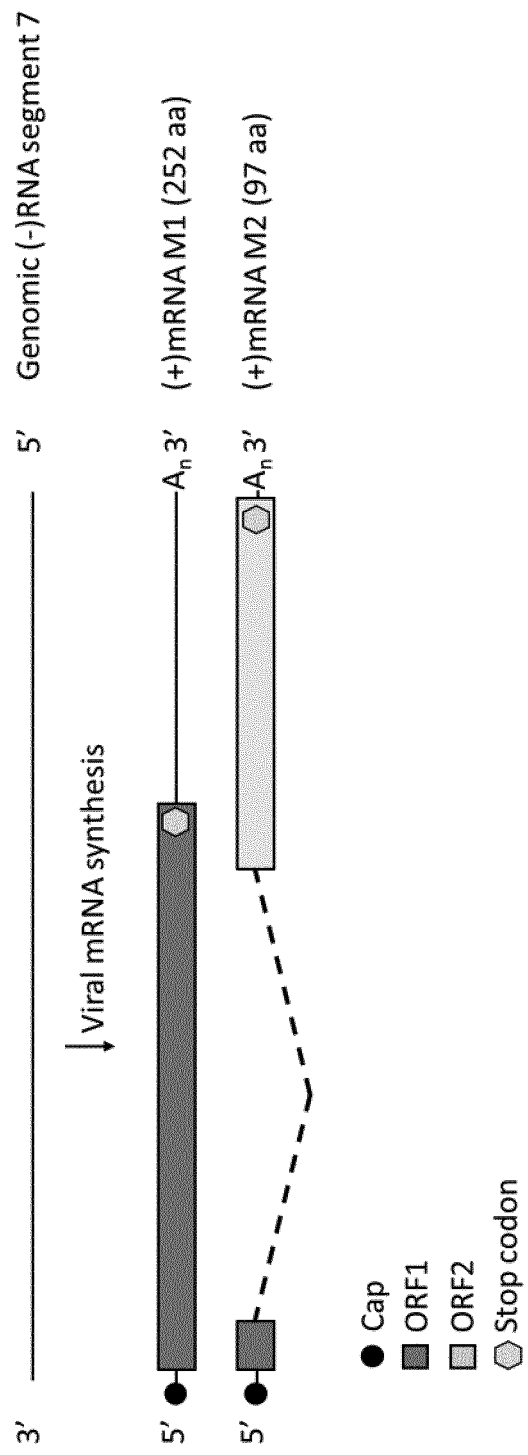
FIG. 2 shows generation of alternative splice variants of influenza A matrix mRNA. During viral mRNA synthesis, the influenza A virus segment 7 gives rise to alternatively spliced RNAs, which encodes matrix proteins M1 and M2. Cap: 5'-cap structure, ORF: open reading frame, aa: amino acid.

In nature, the influenza A matrix-encoding genomic RNA generates at least two alternative spliced mRNAs; mRNA M1 and mRNA M2 (FIG. 2). These two mRNAs encode matrix proteins M1 and M2, respectively. To enable codon optimization of the matrix sequence for M1 and M2 expression in humans without interfering with wild type splicing, the nucleotide sequence comprises separate M1- and M2 coding sequences.

Thus, an embodiment of the present invention relates to the nucleotide sequence as described herein, wherein the nucleotide sequence further comprises one or more influenza genes encoding matrix proteins selected from matrix protein 1 (M1) and matrix protein 2 (M2) and variants thereof.

Influenza virus nucleoprotein (NP) is a structural protein which encapsidates the viral negative stranded RNA. It is a key component of the ribonucleoprotein complex necessary for viral RNA synthesis with a relatively well conserved amino acid sequence. NP is one of the main determinants of species specificity and constitutes a relevant antigenic target for vaccination.

Therefore, an embodiment of the present invention relates to the nucleotide sequence as described herein, wherein the nucleotide sequence further comprises an influenza gene encoding nucleoprotein (NP) or variants thereof.

The nucleotide sequences may be utilized in vaccines termed "nucleotide vaccines". These vaccines are neither built on inactivated or attenuated virulent microorganisms nor protein subunits, but instead functions by inoculation of antigen-encoding DNA or RNA as either synthetic genes or incorporated into various expression cassettes or vectors in order to induce immunity to the gene product. Thus, a nucleotide vaccine may comprise a nucleotide sequence composed of either DNA or RNA Consequently, an embodiment of the present invention relates to the nucleotide sequence as described herein, wherein the nucleotide sequence is comprised of DNA or RNA nucleotides.

A preferred embodiment of the present invention relates to the nucleotide sequence as described herein, wherein the nucleotide sequence is comprised of DNA nucleotides.

Influenza viruses are negative stranded RNA viruses that make up four of the seven genera of the family Orthomyxoviridae. The four genera are denoted Influenza A virus, Influenza B virus, Influenza C virus and Influenza D virus.

Therefore, an embodiment of the present invention relates to the nucleotide sequence as described herein, wherein the influenza genes originate from Influenza A virus or Influenza B virus.

Especially, influenza A virus is of interest since it is known to comprise the most virulent human pathogens among the four influenza genera and causes the severest disease with the risk of causing pandemics with rather frequent occurrences. Examples of variants of influenza A virus that has caused pandemics include H1N1 (Spanish Flu in 1918, Swine Flu in 2009) and H3N2 (Hong Kong flu 1968). It has also caused panzootics, including the H5N1 (Bird flu 2004), which caused a global concern for potential recombination with human strains. Consequently, protection against influenza A virus is of high relevance.

Thus, a preferred embodiment of the present invention relates to the nucleotide sequence as described herein, wherein the influenza genes originates from Influenza A virus.

Another embodiment of the present invention relates to the nucleotide sequence as described herein, wherein the influenza genes originate from one or more pandemic influenza strains.

The nucleotide sequence construct may encode multiple selected influenza proteins derived from pandemic strains like H1N1 1918, H2N2 1957, H1N1pdm2009, H3N2 1968. However, the applicability of the nucleotide sequence as described herein is not limited to any specific influenza strain.

Thus, a further embodiment of the present invention relates to the nucleotide sequence as described herein, wherein the pandemic influenza strains are one or more selected from the group consisting of H1N1pdm2009, H3N2 1968, H2N2 1957 and H1N1 1918.

The influenza virus proteins haemagglutinin (HA) and neuraminidase (NA) play crucial roles as antigenic targets for vaccination directed against influenza. Many variants of influenza virus with different combinations of subtypes of HA and NA exist, with some variants being more abundant and/or pathogenic. HA exist in at least 18 subtypes denoted H1-H18 and NA exist in at least 11 subtypes denoted N1-N11, in which e.g. H1-H18 is to be understood as H1, H2, H3, H4, H5, H6, H7, H8, H9, H10, H11, H12, H13, H14, H15, H16, H17 and H18.

Thus, an embodiment of the present invention relates to the nucleotide sequence as described herein, wherein the one or more influenza genes encoding haemagglutinin (HA) are selected from H1-H18 and the one or more influenza genes encoding neuraminidase (NA) are selected from N1-N11. Especially favored are combinations of H1, H3, N1 and N2.

Although the present invention is not limited to any specific combination of subtypes of HA and NA, some combinations of HA and NA are preferred in the present context.

Thus, an embodiment of the present invention relates to the nucleotide sequence as described herein, wherein the one or more influenza genes encoding haemagglutinin (HA) are selected from:
  (i) SEQ ID NO:8 or SEQ ID NO:12, or
  (ii) a nucleic acid sequence having at least 80% sequence identity to SEQ ID SEQ ID NO:8 or SEQ ID NO: 12,
    wherein the amino acid sequences resulting from the nucleic acid sequences of (ii) are immunogenic.

Another embodiment of the present invention relates to the nucleotide sequence as described herein, wherein the nucleic acid sequence has at least 80% sequence identity to SEQ ID NO:8 or SEQ ID NO:12, such as at least 85%, at least 90%, at least 91%, at least 92%, at least 93%, at least 94%, at least 95%, at least 96%, at least 97%, at least 98%, at least 99%, and at least 99.5%.

A further embodiment of the present invention relates to the nucleotide sequence as described herein, wherein the one or more influenza genes encoding neuraminidase (NA) are selected from:
  (i) SEQ ID NO:14 or SEQ ID NO:16, or
  (ii) a nucleic acid sequence having at least 80% sequence identity to SEQ ID SEQ ID NO: 14 or SEQ ID NO: 16,
    wherein the amino acid sequences resulting from the nucleic acid sequences of (ii) are immunogenic.

Another embodiment of the present invention relates to the nucleotide sequence as described herein, wherein the nucleic acid sequence has at least 80% sequence identity to SEQ ID NO: 14 or SEQ ID NO: 16, such as at least 85%, at least 90%, at least 91%, at least 92%, at least 93%, at least 94%, at least 95%, at least 96%, at least 97%, at least 98%, at least 99%, and at least 99.5%.

Yet another embodiment of the present invention relates to the nucleotide sequence as described herein, wherein the one or more influenza genes encoding matrix proteins are selected from:
  (i) SEQ ID NO:22 or SEQ ID NO:24, or
  (ii) a nucleic acid sequence having at least 80% sequence identity to SEQ ID SEQ ID NO: 22 or SEQ ID NO: 24,
    wherein the amino acid sequences resulting from the nucleic acid sequences of (ii) are immunogenic.

Another embodiment of the present invention relates to the nucleotide sequence as described herein, wherein the nucleic acid sequence has at least 80% sequence identity to SEQ ID NO:22 or SEQ ID NO:24, such as at least 85%, at least 90%, at least 91%, at least 92%, at least 93%, at least 94%, at least 95%, at least 96%, at least 97%, at least 98%, at least 99%, and at least 99.5%.

A still further embodiment of the present invention relates to the nucleotide sequence as described herein, wherein the influenza gene encoding nucleoprotein (NP) are selected from:
  (i) SEQ ID NO:18, or
  (ii) a nucleic acid sequence having at least 80% sequence identity to SEQ ID SEQ ID NO:18,
    wherein the amino acid sequences resulting from the nucleic acid sequences of (ii) are immunogenic.

Another embodiment of the present invention relates to the nucleotide sequence as described herein, wherein the nucleic acid sequence has at least 80% sequence identity to SEQ ID NO:18, such as at least 85%, at least 90%, at least 91%, at least 92%, at least 93%, at least 94%, at least 95%, at least 96%, at least 97%, at least 98%, at least 99%, and at least 99.5%.

It is to be understood that the nucleic acid sequences encoding various influenza genes may have higher sequence identity with the sequences (SEQ ID NOs) to which they refer. Thus, an embodiment of the present invention relates to the nucleotide sequence as described herein, wherein the nucleic acid sequence has at least 80% sequence identity, such as at least 85%, at least 90%, at least 91%, at least 92%, at least 93%, at least 94%, at least 95%, at least 96%, at least 97%, at least 98%, at least 99%, and at least 99.5%.

A preferred embodiment of the present invention relates to the nucleotide sequence as described herein, wherein the nucleotide sequence comprises:
  (i) SEQ ID NO:8 and SEQ ID NO:14, and/or
  (ii) SEQ ID NO:12 and SEQ ID NO:16, and/or
  (iii) SEQ ID NO:22, SEQ ID NO:24 and SEQ ID NO:18, and variants of any of (i), (ii) and/or (iii).

Another embodiment of the present invention relates to the nucleotide sequence as described herein, wherein the nucleotide sequence comprises:
(i) SEQ ID NO:8 and SEQ ID NO:14, and
(ii) SEQ ID NO:12 and SEQ ID NO:16,
and variants of any of (i) and (ii).

An even further embodiment of the present invention relates to the nucleotide sequence as described herein, wherein the nucleotide sequence comprises:
(i) SEQ ID NO:8 and SEQ ID NO:14, and
(ii) SEQ ID NO:12 and SEQ ID NO:16, and
(iii) SEQ ID NO:22, SEQ ID NO:24 and SEQ ID NO: 18, and variants of any of (i), (ii) and (iii).

All nucleotide sequence as described herein may be preceded by a Kozak sequence. The Kozak sequence is a sequence which occurs on eukaryotic mRNA and plays an important role in the initiation of the translation process.

Thus, an embodiment of the present invention relates to the nucleotide sequence as described herein, wherein the nucleotide sequence comprises a Kozak sequence (SEQ ID NO:30). Another embodiment of the present invention relates to the nucleotide sequence as described herein, wherein the Kozak sequence (SEQ ID NO:30) is located at the 5' end of the nucleotide sequence.

Moreover, the nucleotide sequence may be terminated with three stop codons in three different reading frames. Thus, an embodiment of the present invention relates to the nucleotide sequence as described herein, wherein the nucleotide sequence comprises three stop codons at the 3' end.

The nucleotide sequence as described here comprise multiple influenza genes that are connected by linkers. The linkers between the influenza protein coding regions hold at least one of the two protein cleavage sites; 1) a furin cleavage site, and 2) a self-cleaving 2A peptide.

The furin cleavage site consists of the motif R-X-R/K-R and its function is to release the newly synthesized protein at its C-terminus, but allow the ribosome to continue translation. In the single nucleic acid construct, each (downstream) furin cleavage site is responsible for the release of the upstream protein, except for the final protein, which terminates with a stop codon. The furin cleavage site sequence can be chosen from RXRR(SEQ ID NO: 31) or RXKR(SEQ ID NO: 32), where X can be any amino acid. Thus, an embodiment of the present invention relates to the nucleotide sequence as described herein, wherein the linkers each comprise a furin cleavage site comprising a sequence selected from RXRR(SEQ ID NO: 31) or RXKR(SEQ ID NO: 32). The present invention exemplifies the furin cleavage site with the amino acid sequence RRKR(SEQ ID NO: 4).

An embodiment of the present invention relates to the nucleotide sequence as described herein, wherein the furin cleavage site comprises the amino acid sequence according to SEQ ID NO:4.

Another embodiment of the present invention relates to the nucleotide sequence according to any one of claims 19-25, wherein the furin cleavage site comprises the nucleotide sequence according to SEQ ID NO:3.

After cleavage, the remaining C-terminal amino acids of the furin cleavage site are eliminated by cellular carbopeptidases, which remove the basic amino acids R and K. The furin cleavage sites in the polygene are thus removed from each mature protein of interest.

The self-cleaving 2A peptide may consist of an amino acid sequence chosen from APVKQTLNFDLLKLAGDVESNPGP (SEQ ID NO:26), ATNFSLLKQAGDVEEN-PGP (SEQ ID NO:27), QCTNYALLKLAGDVESNPGP (SEQ ID NO:28) and EGRGSLLTCGDVEENPGP (SEQ ID NO:29).

Therefore, an embodiment of the present invention relates to the nucleotide sequence as described herein, wherein the self-cleaving 2A peptide comprises an amino acid sequence selected from the group consisting of SEQ ID NO:26, SEQ ID NO:27, SEQ ID NO:28 and SEQ ID NO:29.

The self-cleaving 2A peptide is present to release the linker from the N-terminal end of the downstream protein to be translated. The present invention exemplifies the self-cleaving porcine teschovirus-1 (also known as Teschovirus A) 2A peptide (P2A) with a nucleotide sequence coding for ATNFSLLKQAGDVEENPGP (SEQ ID NO: 27). The P2A has been shown to be highly efficient in its self-processing through ribosome skipping, which impairs the bond between the final glycine (G) and proline (P), without affecting the translation of the downstream protein.

While two specific cleavage sites are described more thoroughly herein, the present invention is not limited to these two specific cleavage sites. Thus, the cleavage sites include, but are not limited to, a self-cleaving 2A peptide, a furin cleavage site, and cleavage sites of cellular enzymes.

In one variant of the nucleotide sequence, the seven selected vaccine genes are separated by selected spacers of a viral 2A self-processing peptide that results in a co-translational cleavage in an unconventional process during intracellular translation resulting in production of all individual vaccine proteins intracellularly. As an alternative and enhancing cleavage strategy, a furin enzyme cleavage site may be incorporated in the cleavage sequence.

Thus, an embodiment of the present invention relates to the nucleotide sequence as described herein, wherein the linkers each comprises a self-cleaving 2A peptide and/or a furin cleavage site.

Another embodiment of the present invention relates to the nucleotide sequence as described herein, wherein the linkers each comprises a self-cleaving 2A peptide.

Cleavage of the expressed nucleotide sequence may be enhanced by introduction of an additional cleavage site, thereby enabling cleavage at the N- and C-terminals of two adjacent gene products of the nucleotide sequence.

Therefore, an embodiment of the present invention relates to the nucleotide sequence as described herein, wherein the linkers each comprises at least two cleavage sites.

A preferred embodiment of the present invention relates to the nucleotide sequence as described herein, wherein the linkers each comprises a furin cleavage site and a self-cleaving 2A peptide.

To even further enhance the cleavage of the 2A peptide, a GSG peptide coding sequence may be inserted between the furin cleavage site and the self-cleaving 2A. This setup allows for a versatile monocistronic polyprotein generating construct, which can express several individual proteins from one single open reading frame in equimolar ratios.

Therefore, an embodiment of the present invention relates to the nucleotide sequence as described herein, wherein the linkers each comprise a GSG peptide between the furin cleavage site and the self-cleaving 2A peptide.

In the present invention, the nucleotide sequence may also comprise a cassette with unique restriction enzyme sites for easy molecular deletion of particular components like one or more vaccine genes like the internally influenza protein NP. Thus, in an embodiment of the present invention, the two linkers flanking the sequence coding for NP may be modified to comprise a restriction enzyme site (KasI) to enable the removal, or exchange, of NP. The nucleic acid sequence has been modified, but the protein sequence is the same as in the unmodified linker. This modification does not affect the expression of the proteins and can be applied to other linkers in the nucleotide vaccine construct, if desired.

Thus, an embodiment of the present invention relates to the nucleotide sequence as described herein, wherein the linkers each comprises SEQ ID NO:5 or SEQ ID NO:7.

Previous influenza vaccines have been subject to different adverse effects, such as cases of narcoleptic seizures. To avoid a presumed narcolepsy risk for certain individuals that was coupled to the Pandemrix influenza vaccine, putative narcolepsia epitopes in NP and HA may be carefully mutated to minimize or prevent induction of immunity to human epitopes suggested to be involved in narcolepsy. Thus, to minimize the potential risk of narcolepsy, the HA (H1N1) amino acid sequence HDSNKGV (SEQ ID NO: 33) may be changed to HDSDKGV (SEQ ID NO: 34) and the NP (H1N1) epitope sequence YDKEEIRRIWR (SEQ ID NO: 35) may be changed to WEKDDIKRIYK (SEQ ID NO: 36). Hence, both putative regions, suspected of potentially playing a role for narcolepsy, may in some embodiments be altered.

Thus, an embodiment of the present invention relates to the nucleotide sequence as described herein, wherein SEQ ID NO:8 is replaced by SEQ ID NO: 10.

Another embodiment of the present invention relates to the nucleotide sequence as described herein, wherein an amino acid sequence resulting from translation of said one or more influenza genes encoding haemagglutinin (HA) comprises SEQ ID NO:11.

A further embodiment of the present invention relates to the nucleotide sequence as described herein, wherein SEQ ID NO: 18 is replaced by SEQ ID NO: 20.

An even further embodiment of the present invention relates to the nucleotide sequence as described herein, wherein an amino acid sequence resulting from translation of said influenza gene encoding nucleoprotein (NP) comprises SEQ ID NO:21.

In one version of the nucleotide sequence as described herein, seven selected individual influenza vaccine genes are used in a selected order as one polycistronic-like or multigene sequence. The nucleotide sequence (as depicted in FIG. 1 and SEQ ID NO: 1) comprises the influenza A virus genes coding for hemagglutinins (HA) from H1N1 (including an amino acid change in the site implicated in narcolepsy) and from H3N2, neuraminidases (NA) from H1N1 and H3N2, matrix protein 1 (M1), matrix protein 2 (M2) and nucleoprotein (NP) from H1N1 (including an epitope change in the site suspected playing a role in narcolepsy), all interspaced with furin-P2A linkers comprising cleavage sites to produce individual proteins. A Kozak sequence (GCCACC, SEQ ID NO:30) is present at the 5'-end, and the sequence terminates with three stop codons in three different reading frames (TGAcTAGtTAA, SEQ ID NO: 37). Sequences coding for HA, NA, NP, M1, M2 and furin have been codon optimized for expression in humans.

Thus, a preferred embodiment of the present invention relates to the nucleotide sequence as described herein, wherein the nucleotide sequence comprises SEQ ID NO:1.

Another embodiment of the present invention relates to the nucleotide sequence as described herein, wherein the nucleotide sequence consists of SEQ ID NO: 1.

The nucleotide sequence as described herein may be designed for insertion in a DNA plasmid for eukaryotic in vivo expression as a naked DNA where the key element of the vector is CMV Immediate early promotor, Kozak sequence, stop codons in all three reading frames and a polyadenylation signal and a bacterial selection marker for DNA production that do not need to be an antibiotic resistance selection.

The nucleotide sequence as described herein may also be designed for insertion in an mRNA producing vector containing a T7 promotor for RNA production and thus RNA vaccination. Alternatively, the nucleotide sequence can also be inserted in a self-amplifying RNA construct derived from alphavirus as a naked self-amplifying RNA or be inserted into a live viral vector that can be used for live-vector genetic vaccinations. Thus, the nucleotide as described herein is not limited to a specific delivery system.

An embodiment of the present invention relates to the nucleotide sequence as described herein, wherein the nucleotide sequence is incorporated into an expression vector.

In one embodiment, the eukaryotic expression vector in the DNA vaccine plasmid will contain the key elements: a strong constitutive CMV IE promotor, a Kozak translation initiation sequence, a polyadenylation signal, origin of replication and a selection marker for propagating the plasmid in suitable *E. coli* bacteria. To improve safety of the plasmid, the use of an antibiotic selection marker may be substituted with the use of an miRNA shutting down a suicide gene in the permissive *E. coli* strain, using the so called HyperGRO technology, but other plasmids and production methods may be used to optimize production yields and safety e.g. for pigs and other production animals. For mRNA vaccine production, the nucleotide influenza vaccine gene can e.g. be inserted in a vector with a T7, SP6 or T3 promoter for mRNA vaccine production or in expression constructs with alphavirus genes to produce self-amplifying RNA vaccines. Optimization of the immune induction to naked DNA plasmids also involve the delivery method. In this regard, needle-free delivery to the skin, e.g. in rabbits and pigs, may improve the immune induction equally to or better than intradermal injection followed by electroporation. In agreement, others have found that needle-free delivery of DNA vaccine to the skin is superior to delivery to the muscle of pigs. Therefore, to improve the immunogenicity and to save vaccination time, thus avoid retention of many pigs that also improve animal welfare, herein is preferred the needle-free delivery to the skin of DNA or RNA e.g. in mass-vaccinations of pigs and other production animals, but which is also suitable for humans.

Subsequent to delivery to a subject, the nucleotide sequence is expressed and processed to the final individual antigenic peptides or proteins.

Thus, an embodiment of the present invention relates to the nucleotide sequence as described herein, wherein the nucleotide sequence is expressed and cleaved at each cleavage site in vivo in a subject to provide the individual antigenic peptides encoded by said influenza genes.

The vaccination strategy described herein is not limited to human use, but is in principle applicable to all mammals. Thus, an embodiment of the present invention relates to the nucleotide sequence as described herein, wherein the subject is a mammal.

Another embodiment of the present invention relates to the nucleotide sequence as described herein, wherein the subject is selected from the group consisting of humans, pigs, horses, birds, cattle, dogs, ferrets, mice, rabbits and guinea pigs.

A further and preferred embodiment of the present invention relates to the nucleotide sequence as described herein, wherein the subject is a human.

The influenza genes of the nucleotide sequence may be codon optimized for high expression in human cells and thus other mammalian cells.

Therefore, an embodiment of the present invention relates to the nucleotide sequence as described herein, wherein the nucleotide sequence is codon optimized for expression in humans.

The present invention additionally relates to a nucleotide vaccine for immunizing against influenza A disease in humans and animals. The nucleotide vaccine gene construct has several features in its design that together provide a more safe, polyvalent and broad protection against influenza A strains in humans and animals, e.g. pigs, horses and birds.

Therefore, another aspect of the present invention relates to a nucleotide vaccine comprising a nucleotide sequence as described herein.

The nucleotide vaccine may comprise components normally provided together with a vaccine and which would be known to a person skilled in the art. Such components include, but are not limited to, diluents, excipients and adjuvants.

Thus, an embodiment of the present invention relates to the nucleotide vaccine as described herein, wherein the nucleotide vaccine is provided with a pharmaceutical acceptable diluent, excipient and/or adjuvant.

When used as a naked DNA vaccine the single nucleotide sequence may be incorporated into a eukaryotic expression vector as a circular plasmid.

The present invention is also concerned with prevention of disease by providing an effective nucleotide vaccination. The nucleotide vaccine may be administered by standard means and in doses suitable for inducing an immune response and obtaining a sustained protective effect.

Consequently, a further aspect of the present invention relates to a nucleotide sequence as described herein or a nucleotide vaccine as described herein for use in the prevention of influenza infection.

Another embodiment of the present invention relates to the nucleotide sequence or nucleotide vaccine as described herein for use as a therapeutic vaccine.

An embodiment of the present invention relates to the nucleotide sequence or nucleotide vaccine for use as described herein, wherein the nucleotide sequence or nucleotide vaccine is administered in an effective amount.

The nucleotide sequence constructs may be used in influenza A vaccines for human or animal use. Thus, another embodiment of the present invention relates to the nucleotide sequence or nucleotide vaccine for use as described herein, wherein the nucleotide sequence or nucleotide vaccine as described herein is administered to a human or an animal, preferably a human.

The nucleotide sequence or nucleotide vaccine may be supplied as a kit for easy use.

Consequently, another aspect of the present invention relates to a kit comprising:
  (i) an effective amount of a nucleotide sequence as described herein, or
  (ii) an effective amount of a nucleotide vaccine as described herein, and
  (ii) optionally, instructions for use.

The strategy of expressing a single nucleotide sequence comprising cleavage sites for easy in vivo separation of the individual antigenic peptides or proteins encoded by the nucleotide sequence is a general concept that may be expanded to development of vaccines for many different diseases.

Therefore, yet another aspect of the present invention relates to a method for producing a nucleotide vaccine comprising multiple antigen-encoding nucleic acids, said method comprising the following steps:
  (i) providing a nucleotide sequence of at least two genes encoding antigenic peptides or proteins, wherein said at least two genes are connected by linkers comprising at least one cleavage site, and
  (ii) mixing said nucleotide sequence with a pharmaceutical acceptable diluent, excipient and/or adjuvant, thereby providing a nucleotide vaccine.

An embodiment of the present invention relates to the method as described herein, wherein said antigen-encoding nucleic acids originates from a genus selected from the group consisting of alphainfluenzavirus and betainfluenzavirus.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1: Construction of Polygene DNA Vaccines

All selected influenza A sequences are obtained from GenBank and codon optimized for expression in humans, maintaining their original amino acid sequence. The DNA is synthetically synthesized and cloned into a high efficiency expression vector, NTC-9385R (Nature Technology Corp., Lincoln Nebr., USA). Key features of this expression vector are small vector size, high expression and antibiotic-free selection marker RNA-OUT (Williams J A, Vaccines 2013, 1, 225-249).

Two variants of the invention are produced I) a 7mer, coding for seven influenza proteins [hemagglutinins (HA) and neuraminidases (NA) from A/California/04/09 (H1N1) and A/Aichi/2/1968 (H3N2), and nucleoprotein (NP), Matrix protein 1 (M1) and Matrix protein 2 (M2) from A/Brevig Mission/1/1918 (H1N1)], and II) a 4mer, coding for four influenza proteins [hemagglutinins (HA) and neuraminidases (NA) from A/California/04/09 (H1N1) and A/Aichi/2/1968 (H3N2)]. Both constructs are under the control of a CMV promoter and their start codons are in a Kozak sequence context (gccaccatg . . . ). The influenza coding sequences are interspersed by linkers containing a furin cleavage site and a Porcine Teschovirus 1 2A self-cleaving peptide, enabling the processing of the polyprotein into individual proteins. The polyprotein sequences are terminated by three stop codons, one in each reading frame, to ensure translation termination. Both constructs were sequenced, and manufactured under GMP conditions.

Figure 3:
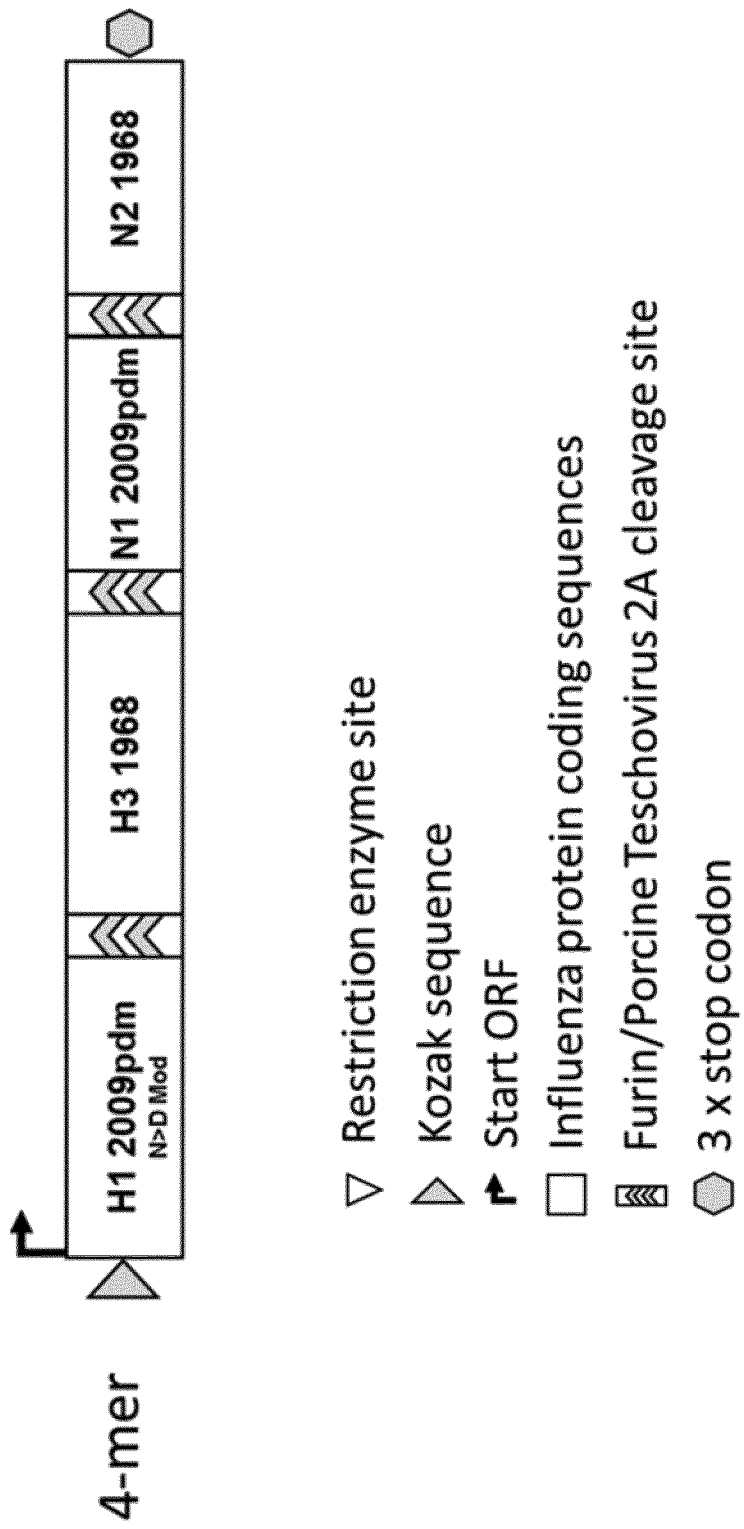
FIG. 3 shows an overview of a 4mer polygene influenza vaccine construct comprising 4 different selected influenza A virus proteins (HA (H1 and H3), NA (N1 and N2)), interspaced with cleavage sites for furin and porcine teschovirus-1 2A (P2A).
Figure 4:
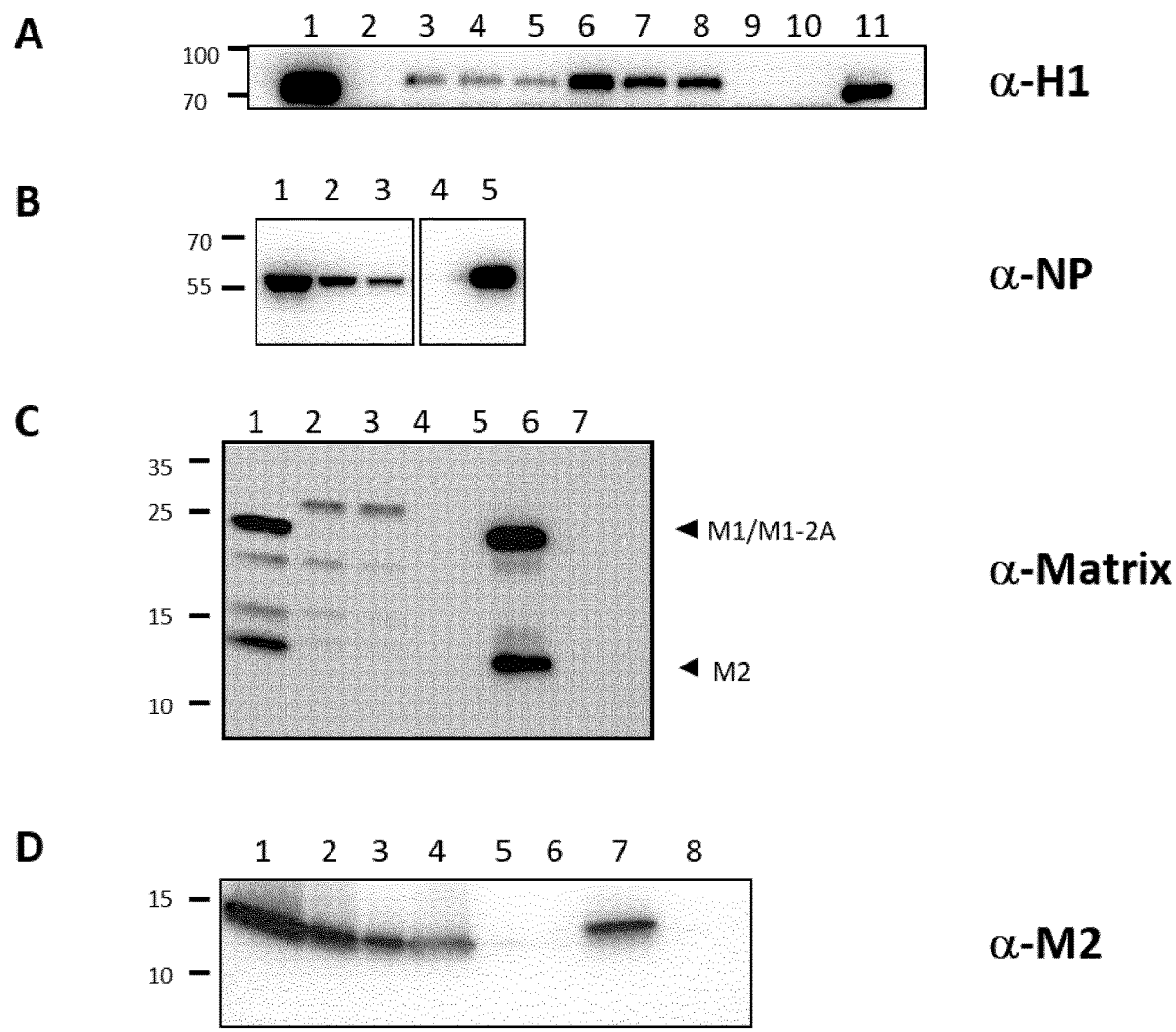
FIG. 4 shows expression of processed influenza proteins from the 7mer and 4mer. (A) Expression of processed hemagglutinin (HA; H1N1). (B) Expression of processed nucleoprotein (NP; H1N1). (C) Expression of processed Matrix proteins 1 and 2 (M1, M2; H1N1). (D) Expression of processed Matrix protein 2 (M2; H1N1).

The 7mer construct is depicted in FIG. 1 and the 4mer construct is depicted in FIG. 3.

Example 2: Expression of Processed Proteins from Polygene DNA Vaccine

To confirm expression from the polygene DNA vaccine constructs, the plasmids are transfected into eukaryotic cells (HEK 293) and examined by immunoblotting. Transfected cells are harvested at 24 or 48 h post transfection, and cytoplasmic lysates are prepared. The lysates are separated on SDS-PAGE and analyzed by western blot using antibodies against the influenza proteins H1 (anti-HA (H1N1) A01500, Genscript), NP (anti-Inf A 1918 NP, clone IC5-1B7 BEI, USA), M1 and M2 (anti-Inf A M1, HYB344-01, SSI, Denmark, and anti-Inf A M2, PA5-32233, ThermoFisher).

The resulting expression of proteins comprised in the DNA vaccine construct is depicted in FIG. 4A-D. More specifically, the lanes of the immunoblots depicted in FIG. 4A-D represents the following:

(A) Expression of Processed Hemagglutinin (HA; H1N1) HEK 293 cells transfected with (1) H1 expression plasmid, (2) H3 expression plasmid, (3-4) 4mer, (5) 4mer+furin expression plasmid, (6-7) 7mer, (8) 7mer+furin expression plasmid, (9) furin-expression plasmid, (10) uninfected HEK 293 cells, and positive control (11) MDCK cells infected with A/California/04/09.

(B) Expression of Processed Nucleoprotein (NP; H1N1) HEK 293 cells transfected with (1) NP-expressing plasmid (positive control), (2-3) 7mer. Negative control (4) uninfected HEK 293. Positive control (5) MDCK cells infected with A/California/04/09.

(C) Expression of Processed Matrix Proteins 1 and 2 (M1, M2; H1N1) HEK 293 cells transfected with (1) Matrix-expressing plasmid (positive control), (2-3) 7mer. Negative controls (4) uninfected HEK 293, and (7) uninfected MDCK cells. Positive control (5) MDCK cells infected with A/California/04/09.

(D) Expression of Processed Matrix Protein 2 (M2; H1N1)
HEK 293 cells transfected with (1) Matrix-expressing plasmid (positive control), (2-3) 7mer, (4) 7mer and furin expressing plasmid or (5) furin plasmid. Negative controls (6) uninfected HEK 293, and (8) uninfected MDCK cells. Positive control (7) MDCK cells infected with A/California/04/09.

Conclusion

In vitro expression of the proteins encoded by the DNA vaccine construct is confirmed. In vitro processing of the polyprotein into individual proteins, exemplified by H1, NP and M2, is confirmed. In vitro processing of the modified linker (SEQ ID NO: 7) flanking NP, is confirmed.

Example 3: Vaccination in Animal Models

The immune response against the polygene DNA vaccine is examined in two animal models; mice (FIG. 6A-B) and rabbits (FIG. 6C-F).

In the experiment conducted in mice, 16 female mice (strain CB6F1, 8 weeks of age) are divided in two groups. The first group (n=8) receives the 7mer vaccine in PBS, while the second group (n=8) receives the 7mer vaccine in the adjuvant Diluvac Forte® (adjuvant component of PRRSV vaccine, MSD Animal Health). The active adjuvant component of Diluvac Forte® is DL-α-tocopherol. The mice receive two vaccinations, at day 0 and day 21, with 50 µg DNA vaccine/vaccination, administered intracutaneously by injection. Blood samples are collected at three occasions; pre-vaccination (day −1), pre-boost (day−20) and two weeks after second vaccination (day 35). Splenocytes are isolated at day 35 and used for cellular immune response analyses.

In the experiment conducted in rabbits, 9 female rabbits (strain NZW, 10 weeks of age) are divided in three groups with three rabbits in each group. Group 1 receives the 7mer in PBS, administered intradermally by a needle-free device (2×100 uL, Tropis, Pharmajet). Group 2 receives the 7mer in Diluvac Forte®, administered intradermally by a needle-free device (1×200 µL, IDAL gun, IDAL). Group 3 receives the 4mer in Diluvac Forte®, administered intradermally by a needle-free device (1×200 µL, IDAL gun, IDAL). All groups are vaccinated twice, on day 0 and day 22 with 125 µg DNA vaccine at each occasion. Blood samples are taken pre-vaccination (day −1), pre-boost (day 21) and two weeks after the second vaccination (day 35).

Figure 5:
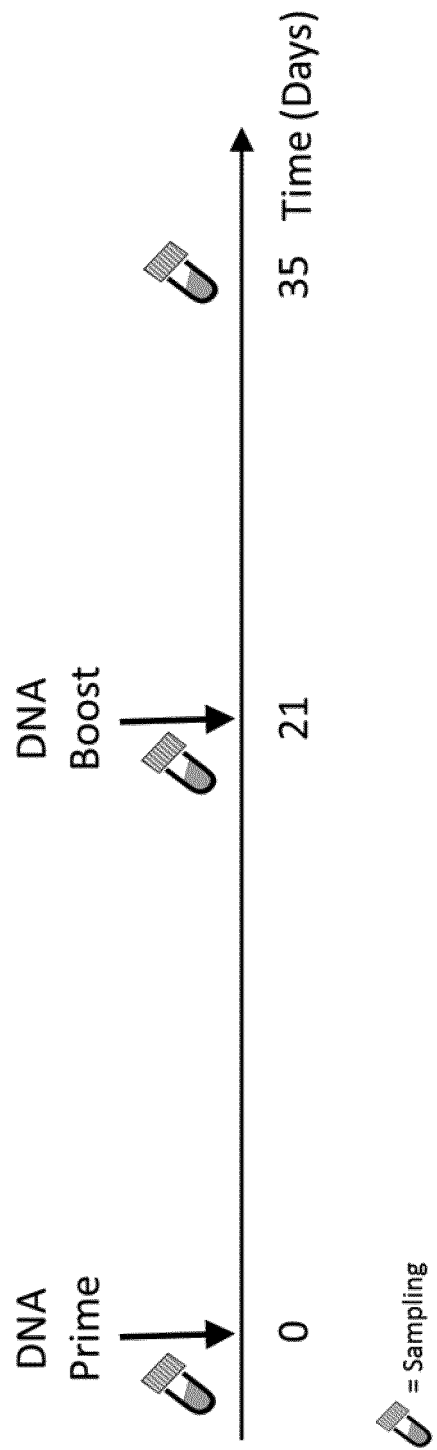
FIG. 5 shows DNA vaccination and blood sampling scheme for mice and rabbits.

The vaccination scheme is outlined in FIG. 5.

Conclusion

All animals were reported to be in good health post vaccination, and did not react adversely against the vaccine.

Example 4: Generation of Antibody Response Against the Polygene DNA Vaccine

The generation of an antibody response against the influenza proteins present in the DNA vaccine is analyzed in both mice and rabbits by antibody ELISA. 96-well plates are coated with 100 µL influenza protein (0.2 µg/mL for mice and 2 µg/mL for rabbits, Sino Biologicals) in carbonate buffer pH 9.6 overnight at 4° C. Wells are then blocked with 2% skim milk in dilution buffer (SSI Diagnostica) for 1 h at room temperature (RT) followed by a wash with PBS with 0.1% Triton X-100. Wells are then incubated with serially diluted serum and incubated for 1 h at RT. Unbound antibodies are washed away with PBS with 0.1% Triton X-100 and an HRP-labeled secondary antibody is added matching the primary antibody and the plate is incubated 1 h at RT. Plates are washed again with PBS with 0.1% Triton X-100 and 100 µL of TMB substrate (KemEnTech) is added. The reaction is incubated at RT in the dark for 30 min, whereupon 150 µL 0.2M $H_2SO_4$ is added to stop the reaction. Reactants are identified by measuring absorbance at 450 nm. All absorbances are calculated as the difference between Abs450 nm and Abs620 nm, with subtracted blank values. Error bars: SEM.

In mice, a strong response against HA (H1N1 A/Cal/04/09) and NP (H1N1 A/Brevig Mission/1/18) was observed after vaccination with the 7mer (see FIG. 6A-B).

In rabbits, both DNA vaccines (7mer and 4mer) antibody responses were induced against HA (H1N1 A/Cal/04/09), H3 and N2 (see FIG. 6C-D and FIG. 6F). The 7mer also induced an antibody response against NP (H1N1 A/Brevig Mission/1/18), a protein lacking in the 4mer vaccine (see FIG. 6E).

Conclusion

The polygene DNA vaccine is able to induce antibody production against both early and late proteins in the polygene construct (e.g. H1 and NP) and these antibodies can react against purified influenza proteins.

Example 5: Generation of Cellular Response Against the Polygene Nucleotide Vaccine To assess the ability of the 7mer polygene vaccine to induce cellular immune responses, splenocytes from mice immunized with 7mer in the presence of PBS or Diluvac Forte, were isolated and re-stimulated with homologous influenza proteins (HA, NP and M1) for 72 h.

Following stimulation, supernatants were collected and interferon gamma (INF-gamma) and IL-17A were quantified in cytokine-ELISAs specific for IFN-gamma or IL-17A, as surrogates for T helper 1 (Th1) and Th17 cellular responses, respectively (see FIG. 7A-B). Average responses are indicated as a horizontal line in each group. Statistical analysis was performed using ANOVA comparison paired with Sidak significance analysis (95% confidence interval).

*P≤0.05, P≤0.01, *P≤0.001, ****P≤0.0001

All three influenza proteins induced IFN-gamma production. Conversely, only M1 induced IL-17A production.

The 7mer polygene vaccine induces cellular immune responses characterized by the secretion of IFN-gamma upon stimulation with (i) wild type influenza surface protein (HA) as well as (ii) wild type internal proteins (NP and M1) (FIG. 7A). This provides additional evidence towards the production, processing and presentation of the vaccine-associated viral proteins to antigen presenting cells. The isolated immune cells from this experiment could also be stimulated by M1 to produce IL-17A (FIG. 7B), which is an important cytokine for the recruitment of immune cells that eliminate infected cells.

Conclusion

The observed responses against IFN-gamma and IL-17A confirm the priming of the immune system by the 7mer polygene vaccine and supports the observation of an acquired ability of the immune system to recognize influenza viruses as well as the activation of different subset of immune cells.

Example 6: Relative Protein Expression from Polygene Nucleotide Vaccine

A DNA influenza vaccine composed of six individual plasmids encoding the seven influenza proteins present in the 7mer polygene has previously been described in WO2010060430. Here, the 7mer polygene nucleotide vaccine is compared to the DNA influenza vaccine of WO2010060430.

Figure 8:
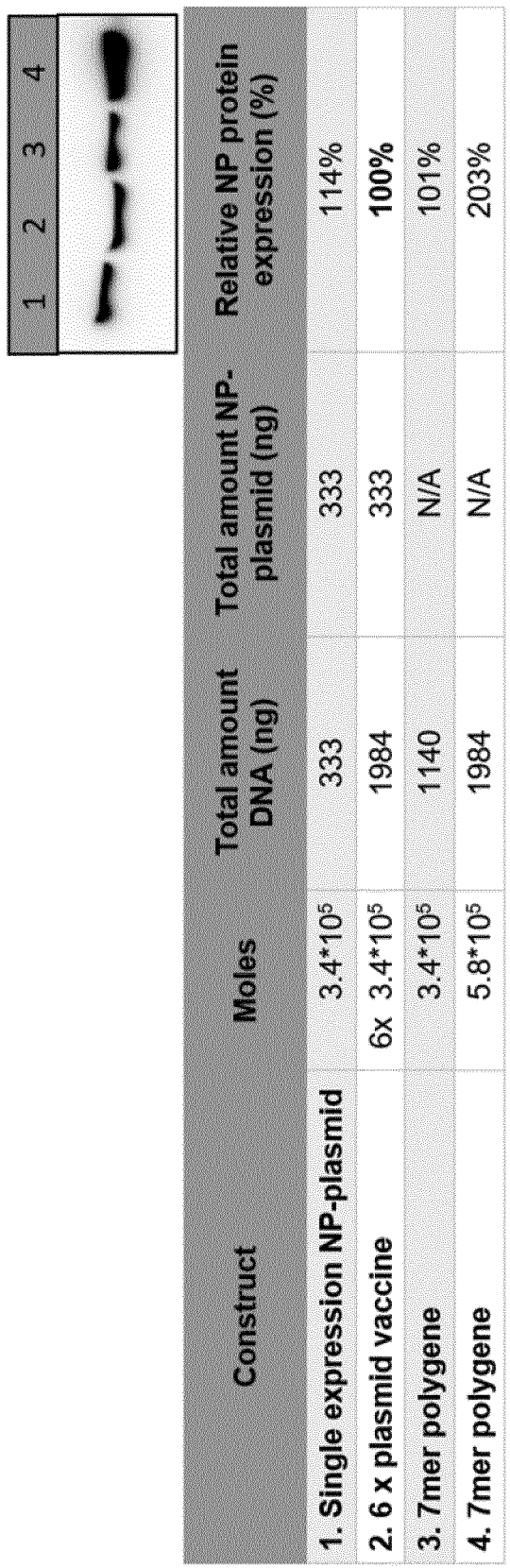
FIG. 8 Relative nucleoprotein (NP) expression from polygene nucleotide construct. HEK 293 cells were transfected with either equimolar or equal DNA amounts of 7mer nucleotide, a single NP-expression plasmid or a mix of six individual plasmids expressing the seven influenza proteins encoded by the 7mer nucleotide. Equal amounts of cytoplasmic extracts were evaluated with a western blot specific for NP. Subsequent densiometric analysis was performed with Scion Image Beta 4.0.2. Relative protein expression was calculated using 6× plasmid vaccine as reference.

The relative protein expression of these two vaccine candidates was evaluated in vitro by transfection of HEK 293 cells with equimolar and equal absolute DNA amounts of these constructs. As a comparison, one of the six plasmids present in the six-plasmid vaccine, encoding NP, was used as a control. Cells were lipofected with PolyFect with various amounts of DNA (see FIG. 8 for details) using the protocol for transient transfection provided by the manufacturer (PolyFect transfection reagent, Qiagen). Cytoplasmic extracts were prepared 48 h post lipofection, and 30 µg of extract was analyzed on a 10% PAGE followed by a western blot specific for NP (primary antibody; mouse Mab Inf A 1918 NP clone IC5-1B7 (NR-43899) BEI, USA). The relative expression was then calculated using densitometry data obtained with Scion Image Beta 4.0.2. The previously characterized six-plasmid vaccine was used as a reference to calculate the relative protein expression of NP.

When using equimolar amounts of NP-expressing plasmids, i.e. (i) single expression NP-plasmid, (ii) six-plasmid vaccine, or (iii) 7mer polygene nucleotide vaccine, equal amounts of NP-protein is obtained. However, if the same absolute DNA amounts of the six-plasmid vaccine and the 7mer polygene nucleotide vaccine is used, the 7mer polygene nucleotide vaccine produces approximately twice as much NP-protein (see FIG. 8).

Conclusion

Consequently, vaccination with the same DNA amount of the six-plasmid vaccine and the 7mer polygene nucleotide vaccine generates a superior protein expression by the 7mer polygene nucleotide vaccine (exemplified by NP). Therefore, less DNA can be used for vaccination with the 7mer polygene nucleotide vaccine.

REFERENCES

WO2016041562
WO2008145129
WO2010060430
Williams J. Vector design for improved DNA vaccine efficacy, safety and production. Vaccines 2013; 1:225-249

Items

Item 1. A single nucleotide sequence comprising the influenza genes coding for haemagglutinin (HA) and neuraminidase (NA) fused together with linkers comprising two cleavage sites.

Item 2. A single nucleotide sequence comprising according to item 1, additionally comprising influenza genes coding matrix protein 1 (M1) and matrix protein 2 (M2) fused together with linkers comprising two cleavage sites.

Item 3. A single nucleotide sequence comprising the influenza genes according to item 2, additionally comprising an influenza gene coding nucleoprotein (NP).

Item 4. A single nucleotide sequence according to any one of items 1-3, wherein the influenza genes stems from pandemic influenza strains.

Item 5. A single nucleotide sequence according to item 4, where the HA (H1) and NA (N1) stems from H1N1pdm2009, HA (H3) and NA (N2) stems from H3N2 1968 and M1, M2 and NP stems from H1N1 1918.

Item 6. A single nucleotide sequence according to any one of items 1-5, wherein the nucleotides are DNA or RNA.

Item 7. A single nucleotide sequence according to item 6, where the nucleotide sequences are codon optimized for expression in humans.

Item 8. A single nucleotide sequence according to item 7, wherein the linkers comprise a cleavage site for furin.

Item 9. A single nucleotide sequence according to item 8, where the amino acid sequence for the furin cleavage site is RRKR(SEQ ID NO: 4).

Item 10. A single nucleotide sequence according to any one of items 8 or 9, where the linker comprises SEQ ID NO 3.

Item 11. A single nucleotide sequence according to item 7, where the cleavage site is a self-cleaving 2A peptide.

Item 12. A single nucleotide sequence according to item 11, where the self-cleaving 2A peptide amino acid sequence is chosen from the following sequences APVKQTLNFDLLKLAGDVESNPGP (SEQ ID NO: 26), ATNFSLLKQAGDVEENPGP (SEQ ID NO: 27), QCTNYALLKLAGDVESNPGP (SEQ ID NO: 28) and EGRGSLLTCGDVEENPGP (SEQ ID NO: 29).

Item 13. A single nucleotide sequence according to any one of items 1-12, where the linkers comprise a furin cleavage site and a self-cleaving 2A peptide.

Item 14. A single nucleotide sequence according to item 13, where the linkers comprise a GSG peptide between the furin cleavage site and the self-cleaving 2A peptide.

Item 15. A single nucleotide sequence according to item 14, where the linker comprises SEQ ID NO 5 or 7.

Item 16. A single nucleotide sequence according to any one of items 1-15, where the HA (H1N1) amino acid sequence HDSNKGV optionally is changed to HDSDKGV.

Item 17. A single nucleotide sequence according to item 16, where the gene coding for HA comprises SEQ ID NO 8 or 10.

Item 18. A single nucleotide sequence according to any one of items 3-17, where the NP (H1N1) epitope YDKEEIRRIWR optionally is changed to WEKDDIKRIYK.

Item 19. A single nucleotide sequence according to item 18, where the gene coding for NP comprises SEQ ID NO 18 or 20.

Item 20. A single nucleotide sequence according to any one of items 1-19, where the polygene nucleotide sequence is incorporated into an expression vector.

Item 21. A single nucleotide sequence according to any one of items 3-18 as given in SEQ ID NO 1.

Item 22. A vaccine comprising a single nucleotide sequence according to any one of item 1-21.

```
Sequence listing
Polygene nucleotide sequences
                                              (SEQ ID NO 1)
GCCACCATGAAGGCTATCCTGGTGGTGCTGCTGTACACCTTCGCCACCGC

CAACGCCGATACCCTGTGCATCGGCTACCACGCCAACAACAGCACCGACA

CCGTGGATACCGTGCTGGAAAAGAACGTGACCGTGACCCACAGCGTGAAC

CTGCTGGAAGATAAGCACAACGGCAAGCTGTGCAAGCTGAGAGGCGTGGC

CCCTCTGCACCTGGGCAAGTGCAATATCGCCGGCTGGATCCTGGGCAACC

CCGAGTGCGAGAGCCTGAGCACCGCCAGCTCTTGGTCCTACATCGTGGAG

ACACCCAGCAGCGACAACGGCACCTGTTACCCCGGCGACTTCATCGACTA

CGAGGAACTGCGGGAGCAGCTGTCCAGCGTGTCCAGCTTCGAGCGGTTCG

AGATCTTCCCCAAGACCAGCTCCTGGCCCAACCACGACAGCGATAAGGGC

GTGACCGCCGCCTGTCCTCACGCTGGGGCAAGAGCTTCTACAAGAACCT

GATCTGGCTGGTGAAGAAGGGCAACAGCTACCCCAAGCTGTCCAAGAGCT

ACATCAACGACAAGGGCAAAGAGGTGCTGGTGCTGTGGGGCATCCACCAC

CCTAGCACCAGCGCCGACCAGCAGAGCCTGTACCAGAACGCCGACACCTA

CGTGTTCGTGGGCAGCAGCCGGTACAGCAAGAAGTTCAAGCCCGAGATCG

CCATCAGACCCAAAGTGCGGGACCAGGAAGGCCGGATGAACTACTACTGG

ACCCTGGTGGAGCCCGGCGACAAGATCACCTTCGAGGCCACCGGCAATCT

GGTGGTGCCCAGATACGCCTTCGCCATGGAAAGAAACGCCGGCAGCGGCA

TCATCATCAGCGACACCCCCGTGCACGACTGCAACACCACCTGTCAGACC

CCCAAGGGGGCCATCAACACCAGCCTGCCCTTCCAGAACATCCACCCCAT

CACCATCGGCAAGTGCCCTAAGTACGTGAAGTCCACCAAGCTGAGACTGG

CCACCGGCCTGCGGAACATCCCCAGCATCCAGAGCAGAGGCCTGTTCGGG

GCCATTGCCGGCTTTATCGAGGGCGGCTGGACCGGAATGGTGGACGGGTG

GTACGGCTACCACCACCAGAATGAGCAGGGCAGCGGCTACGCCGCCGACC

TGAAGTCCACACAGAACGCCATCGACGAGATCACCAACAAAGTGAACAGC

GTGATCGAGAAGATGAACACCCAGTTCACCGCCGTGGGCAAAGAGTTCAA

CCACCTGGAAAAGCGGATCGAGAACCTGAACAAGAAGGTGGACGACGGCT

TCCTGGACATCTGGACCTACAACGCCGAGCTGCTGGTGCTGCTGGAAAAC

GAGCGGACCCTGGACTACCACGACTCCAACGTGAAGAATCTGTACGAGAA

AGTGCGGAGCCAGCTGAAGAACAACGCCAAAGAGATCGGCAACGGCTGCT

TCGAGTTCTACCACAAGTGCGACAACACCTGTATGGAAAGCGTGAAGAAC

GGCACCTACGACTACCCCAAGTACAGCGAGGAAGCCAAGCTGAACCGGGA

AGAGATCGACGGCGTGAAGCTGGAAAGCACCCGGATCTACCAGATCCTGG

CCATCTACAGCACCGTGGCCAGCTCACTGGTCCTGGTCGTGTCCCTGGGC

GCTATCAGCTTCTGGATGTGCAGCAACGGCAGCCTGCAGTGCCGGATCTG

CATCCGGCGGAAGCGGggaagcggagctactaacttcagcctgctgaagc aggctggagacgtggaggagaaccctggacctATGAAAACCATCATCGCC

CTGAGCTACATCTTCTGCCTCGCCCTCGGCCAGGACCTGCCCGGCAACGA

CAACAGCACCGCCACCCTGTGCCTGGGCCACCACGCCGTGCCCAACGGCA

CCCTGGTGAAAACAATTACCGACGACCAGATCGAGGTGACCAACGCCACC

GAGCTGGTGCAGAGCAGCAGCACCGGCAAGATCTGCAACAACCCCCACCG

CATCCTGGACGGCATCGACTGCACCCTGATCGACGCCCTGCTGGGCGACC

CTCACTGCGACGTGTTCCAGAACGAGACCTGGGACCTGTTCGTGGAGCGC

AGCAAGGCCTTCAGCAACTGCTACCCCTACGACGTGCCCGACTACGCTTC

CCTGCGCAGCCTGGTCGCCAGCTCCGGGACCCTGGAGTTCATCACCGAGG

GCTTCACCTGGACCGGGGTCACACAGAATGGGGGGTCCAACGCCTGCAAG

CGCGGACCCGGCAGCGGCTTCTTCAGCCGCCTGAACTGGCTGACCAAGAG

CGGCAGCACCTACCCCGTGCTGAACGTGACCATGCCCAACAACGACAACT

TCGACAAGCTGTACATCTGGGGCGTGCACCACCCCAGCACCAACCAGGAA

CAGACCAGCCTGTACGTGCAGGCCAGCGGCAGGGTGACCGTGAGCACCCG

CCGCAGCCAGCAGACCATCATCCCCAACATCGAGTCCCGGCCCTGGGTCC

GCGGGCTGTCCAGCCGCATCAGCATCTACTGGACCATCGTGAAGCCCGGC

GACGTGCTGGTGATCAACAGCAACGGCAACCTGATCGCCCCCAGGGGCTA

CTTCAAGATGCGGACCGGCAAGAGCAGCATCATGCGCAGCGACGCCCCCA

TCGACACCTGCATCAGCGAGTGCATCACCCCCAACGGCAGCATCCCCAAC

GACAAGCCCTTCCAGAACGTGAACAAGATCACCTACGGGGCCTGTCCTAA

GTACGTGAAGCAGAACACCCTGAAGCTCGCTACCGGCATGCGGAACGTGC

CCGAGAAGCAGACCAGGGGCCTGTTCGGGGCCATCGCCGGCTTCATCGAG

AACGGCTGGGAGGGCATGATCGACGGGTGGTATGGCTTCCGCCACCAGAA

CAGCGAGGGCACCGGCCAGGCCGCCGACCTGAAGAGCACCCAGGCCGCCA

TCGACCAGATCAACGGCAAGCTGAACCGCGTGATCGAGAAAACCAACGAG

AAGTTCCACCAGATCGAGAAAGAGTTCAGCGAGGTCGAGGGCCGCATCCA

GGACCTGGAGAAGTACGTGGAGGACACCAAGATCGACCTGTGGAGCTACA

ACGCCGAGCTGCTGGTCGCCCTGGAGAACCAGCACACCATCGACCTGACC

GACAGCGAGATGAACAAGCTGTTCGAGAAAACCCGCAGGCAGCTGCGCGA

GAACGCCGAGGACATGGGCAACGGCTGCTTCAAGATCTACCACAAGTGCG

ACAACGCCTGCATCGAGAGCATCCGCAACGGCACCTACGACCACGACGTG

TACCGCGACGAGGCCCTGAACAACCGCTTCCAGATCAAGGGCGTGGAGCT

GAAGAGCGGCTACAAGGACTGGATCCTGTGGATCAGCTTCGCTATCAGCT

GCTTCCTGCTGTGCGTGGTGCTGCTGGGCTTCATCATGTGGGCCTGCCAG

CGGGGCAACATCCGCTGCAACATCTGCATCCGGCGGAAGCGGggaagcgg agctactaacttcagcctgctgaagcaggctggagacgtggaggagaacc ctggacctATGAACCCCAACCAGAAGATCATCACCATCGGCAGCGTGTGC

ATGACCATCGGCATGGCCAACCTGATCCTGCAGATCGGCAACATCATCAG

CATCTGGATCAGCCACAGCATCCAGCTGGGCAACCAGAACCAGATCGAGA

CATGCAACCAGAGCGTGATCACCTACGAGAACAACACCTGGGTGAACCAG

ACCTACGTGAACATCAGCAACACCAACTTCGCCGCTGGCCAGAGCGTGGT

GTCTGTGAAGCTGGCCGGCAACAGCAGCCTGTGCCCTGTGTCCGGCTGGG
```

-continued

```
CCATCTACAGCAAGGACAACAGCGTGCGGATCGGCAGCAAGGGCGACGTG
TTCGTGATCCGGGAGCCCTTCATCAGCTGCAGCCCCCTGGAATGCCGGAC
CTTCTTCCTGACCCAGGGGGCCCTGCTGAACGACAAGCACAGCAACGGCA
CCATCAAGGACAGAAGCCCCTACCGGACCCTGATGAGCTGCCCCATCGGC
GAGGTGCCCAGCCCCTACAACAGCAGATTCGAGTCCGTGGCTTGGAGCGC
CTCTGCCTGCCACGACGGCATCAACTGGCTGACAATCGGCATCAGCGGCC
CTGATAACGGCGCTGTGGCCGTGCTGAAGTACAACGGCATCATCACCGAC
ACAATCAAGAGCTGGCGGAACAACATCCTGCGGACCCAGGAATCCGAGTG
CGCCTGCGTGAACGGCAGCTGCTTCACCGTGATGACCGACGGCCCTAGCA
ATGGCCAGGCCAGCTACAAGATCTTCCGGATCGAGAAGGGCAAGATCGTG
AAGTCCGTGGAGATGAACGCCCCCAACTACCACTACGAGGAATGCAGCTG
CTACCCCGACAGCAGCGAGATCACCTGTGTGTGCCGGGACAACTGGCACG
GCAGCAACAGACCCTGGGTGTCCTTCAACCAGAATCTGGAATACCAGATC
GGCTACATTTGCAGCGGCATCTTCGGCGACAACCCCAGACCCAACGACAA
GACCGGAAGCTGCGGCCCTGTGTCTAGCAACGGGGCCAACGGCGTGAAGG
GCTTCAGCTTCAAGTACGGCAATGGCGTGTGGATCGGCCGGACCAAGAGC
ATCAGCAGCCGGAACGGCTTCGAGATGATCTGGGACCCCAACGGCTGGAC
CGGCACCGACAACAACTTCAGCATCAAGCAGGACATCGTGGGCATCAACG
AGTGGAGCGGCTACAGCGGCAGCTTCGTGCAGCACCCTGAGCTGACCGGC
CTGGACTGCATCCGGCCCTGCTTTTGGGTGGAGCTGATCAGAGGCAGACC
CAAAGAGAACACCATCTGGACCAGCGGCAGCAGCATCAGCTTTTGCGGCG
TGAACAGCGACACCGTGGGCTGGTCTTGGCCCGATGGGGCCGAGCTGCCC
TTCACCATCGACAAGCGGCGGAAGCGGggaagcggagctactaacttcag
cctgctgaagcaggctggagacgtggaggagaaccctggacctATGAACC
CCAACCAGAAGATCATCACCATCGGCAGCGTGAGCCTGACAATCGCTACC
GTGTGCTTCCTGATGCAGATCGCCATCCTGGTGACCACCGTGACCCTGCA
CTTCAAGCAGTACGAGTGCGACAGCCCCGCCAGCAACCAGGTCATGCCCT
GCGAGCCCATCATCATCGAGCGCAACATCACCGAGATCGTGTACCTGAAC
AACACCACCATCGAGAAGGAAATCTGCCCCAAGGTCGTGGAGTACCGCAA
CTGGTCCAAGCCCCAGTGCCAGATCACCGGCTTCGCCCCCTTCAGCAAGG
ACAACAGCATCCGCCTGAGCGCCGAGGGGACATCTGGGTCACCCGCGAG
CCCTACGTGAGCTGCGACCACGGCAAGTGCTACCAGTTCGCTCTGGGGCA
GGGGACAACACTCGATAACAAGCACAGCAACGACACCATCCACGACCGCA
TCCCCCACCGCACCCTGCTGATGAACGAGCTGGGCGTGCCCTTCCACCTG
GGCACCCGCCAGGTCTGCATCGCCTGGTCCAGCAGCAGCTGCCACGACGG
CAAGGCCTGGCTGCACGTGTGCATCACCGGCGACGACAAGAACGCCACCG
CCAGCTTCATCTACGACGGCCGCCTGGTGGACAGCATCGGCAGCTGGTCC
CAGAACATCCTGCGCACCCAAGAAAGCGAGTGCGTCTGCATCAACGGGAC
CTGCACCGTGGTGATGACCGATGGAAGCGCCAGCGGCAGGGCCGATACCC
GGATCCTGTTCATCGAGGAAGGCAAGATCGTGCACATCAGCCCTCTCAGC
GGCTCCGCCCAGCACGTGGAAGAGTGCAGCTGCTACCCCCGCTACCCCGG
CGTGCGCTGCATCTGCCGCGACAACTGGAAGGGCAGCAACCGCCCCGTGG
TGGACATCAACATGGAGGACTACAGCATCGACAGCAGCTACGTGTGCAGC
GGCCTGGTCGGCGACACACCCCGCAACGACGACCGCAGCAGCAACAGCAA
CTGCCGCAACCCCAACAACGAGCGCGGCAACCAGGGCGTGAAGGGCTGGG
CCTTCGACAACGGCGACGACGTGTGGATGGGCCGCACCATCTCCAAGGAC
CTGCGCAGCGGCTACGAGACCTTCAAGGTGATCGGCGGGTGGAGCACCCC
CAACAGCAAGAGCCAGATCAACCGCCAGGTGATCGTGGACAGCGACAACC
GCTCCGGCTACAGCGGCATCTTCAGCGTGGAGGGCAAGTCCTGCATCAAC
CGCTGCTTCTACGTGGAGCTGATCCGCGGCAGGAAGCAAGAAACCCGCGT
CTGGTGGACCAGCAACTCCATCGTGGTGTTCTGCGGCACCAGCGGCACCT
ACGGCACCGGCAGCTGGCCCGACGGGGCCAACATCAACTTCATGCCCATC
CGGCGGAAGCGGggaagcggCgcCactaacttcagcctgctgaagcaggc
tggagacgtggaggagaaccctggacctATGGCCAGCCAGGGCACCAAGA
GAAGCTACGAGCAGATGGAAACCGACGGCGAGAGGCAGAACGCCACCGAG
ATCAGGGCCAGCGTGGGCAGGATGATCGGCGGCATCGGCAGGTTCTACAT
CCAGATGTGCACCGAGCTGAAGCTGTCCGACTACGAGGGCAGGCTGATCC
AGAACAGCATCACCATCGAGAGGATGGTGCTGTCCGCCTTCGACGAGAGA
AGAAACAAGTACCTGGAAGAGCACCCCAGCGCCGGCAAGGACCCCAAGAA
AACCGGCGGACCCATCTACAGAAGGATCGACGGCAAGTGGATGAGAGAGC
TGATCCTGtgggagaaggacgacatcaagcggatctacaagCAGGCCAAC
AACGGCGAGGACGCCACAGCCGGCCTGACCCACATGATGATCTGGCACAG
CAACCTGAACGACGCCACCTACCAGAGGACCAGGGCCCTCGTCAGAACCG
GCATGGACCCCCGGATGTGCAGCCTGATGCAGGGCAGCACACTGCCCAGA
AGAAGCGGAGCTGCTGGAGCCGCCGTGAAGGGCGTGGGCACCATGGTGAT
GGAACTGATCAGGATGATCAAGAGGGGCATCAACGACAGGAACTTTTGGA
GGGGCGAGAACGGCAGAAGGACCAGGATCGCCTACGAGAGGATGTGCAAC
ATCCTGAAGGGCAAGTTCCAGACAGCCGCCCAGAGGGCCATGATGGACCA
GGTCCGGGAGAGCAGGAACCCCGGCAACGCCGAGATCGAGGACCTGATCT
TCCTGGCCAGAAGCGCCCTGATCCTGAGGGGCAGCGTGGCCCACAAGAGC
TGCCTGCCCGCCTGCGTGTACGGACCCGCCGTGGCCAGCGGCTACGACTT
CGAGAGAGAGGGCTACAGCCTGGTCGGCATCGACCCCTTCAGGCTGCTGC
AGAACTCCCAGGTGTACTCTCTGATCAGGCCCAACGAGAACCCCGCCCAC
AAGTCCCAGCTGGTCTGGATGGCCTGCCACAGCGCCGCCTTCGAGGATCT
GAGAGTGAGCAGCTTCATCAGGGGCACCAGAGTGGTGCCCAGGGGCAAGC
TGTCCACCAGGGGCGTGCAGATCGCCAGCAACGAGAACATGGAAACCATG
GACAGCAGCACCCTGGAACTGAGAAGCAGGTACTGGGCCATCAGGACCAG
AAGCGGCGGCAACACCAACCAGCAGAGGGCCAGCGCCGGACAGATCAGCG
TGCAGCCCACCTTCTCCGTGCAGAGGAACCTGCCCTTCGAGAGGGCCACC
ATCATGGCCGCCTTCACCGGCAACACCGAGGGCAGGACCAGAGACATGAG
GACCGAGATCATCAGAATGATGGAAAGCGCCAGGCCCGAGGACGTGAGCT
```

```
TCCAGGGCAGGGGCGTGTTCGAGCTGTCCGATGAGAAGGCCACCTCCCCC
ATCGTGCCCAGCTTCGACATGAGCAACGAGGGCAGCTACTTCTTCGGCGA
CAACGCCGAGGAATACGACAACCGGCGGAAGCGGggaagcggCgcCacta
acttcagcctgctgaagcaggctggagacgtggaggagaaccctggacct
ATGTCCCTGCTGACAGAGGTGGAGACCTACGTGCTGTCCATCGTGCCCTC
TGGCCCTCTGAAGGCCGAGATCGCCCAGAGACTGGAGGACGTGTTCGCCG
GCAAGAACACAGATCTGGAGGCCCTGATGGAGTGGCTGAAGACAAGGCCA
ATCCTGTCTCCCCTGACCAAGGGCATCCTGGGCTTCGTGTTTACACTGAC
CGTGCCTAGCGAGAGGGACTGCAGCGGAGAAGGTTCGTGCAGAATGCCC
TGAACGGCAATGGCGACCCAAACAATATGGATCGGGCCGTGAAGCTGTAT
AGAAAGCTGAAGAGGGAGATCACCTTTCACGGAGCCAAGGAGGTGGCCCT
GTCTTACAGCGCCGGGGCCCTGGCAAGCTGCATGGGACTGATCTATAACA
GGATGGGCACAGTGACCACAGAGGTGGCCTTCGGCCTGGTGTGCGCAACC
TGTGAGCAGATCGCAGACAGCCAGCACCGCTCCCACAGGCAGATGGTGAC
CACAACCAACCCCCTGATCCGCCACGAGAATCGGATGGTGCTGGCCTCCA
CAACCGCCAAGGCCATGGAGCAGATGGCAGGCAGCTCCGAGCAGGCAGCA
GAGGCCATGAGGTGGCCTCTCAGGCCAGACAGATGGTGCAGGCCATGAG
GACAATCGGAACCCACCCTTCTAGCTCCGCCGGCCTGAAGGACGATCTGA
TCGAGAATCTGCAGGCCTACCAGAAGCGCATGGGCGTGCAGATGCAGCGG
TTTAAGCGGCGGAAGCGGggaagcggagctactaacttcagcctgctgaa
gcaggctggagacgtggaggagaaccctggacctATGTCCCTGCTGACCG
AGGTGGAGACCCCAACACGGAACGAGTGGGGCTGCAGATGTAATGACAGC
TCCGATCCCCTGGTCATCGCCGCCTCTATCATCGGCATCCTGCACCTGAT
CCTGTGGATCCTGGACAGGCTGTTCTTTAAGTGCATCTACCGGAGACTGA
AGTATGGCCTGAAGAGAGGCCCCCTCTACAGAGGGCGTGCCTGAGAGCATG
AGGGAGGAGTACCGCAAGGAGCAGCAGAGCGCCGTGGATGTGGACGATGG
CCACTTCGTGAACATCGAGCTGGAGTGACTAGTTAA
```
Polygene amino acid sequences
(SEQ ID NO 2)
```
MKAILVVLLYTFATANADTLCIGYHANNSTDTVDTVLEKNVTVTHSVNLL
EDKHNGKLCKLRGVAPLHLGKCNIAGWILGNPECESLSTASSWSYIVETP
SSDNGTCYPGDFIDYEELREQLSSVSSFERFEIFPKTSSWPNHDSDKGVT
AACPHAGAKSFYKNLIWLVKKGNSYPKLSKSYINDKGKEVLVLWGIHHPS
TSADQQSLYQNADTYVFVGSSRYSKKFKPEIAIRPKVRDQEGRMNYYWTL
VEPGDKITFEATGNLVVPRYAFAMERNAGSGIIISDTPVHDCNTTCQTPK
GAINTSLPFQNIHPITIGKCPKYVKSTKLRLATGLRNIPSIQSRGLFGAI
AGFIEGGWTGMVDGWYGYHHQNEQGSGYAADLKSTQNAIDEITNKVNSVI
EKMNTQFTAVGKEFNHLEKRIENLNKKVDDGFLDIWTYNAELLVLLENER
TLDYHDSNVKNLYEKVRSQLKNNAKEIGNGCFEFYHKCDNTCMESVKNGT
YDYPKYSEEAKLNREEIDGVKLESTRIYQILAIYSTVASSLVLVVSLGAI
SFWMCSNGSLQCRICIRRKRGSGATNFSLLKQAGDVEENPGPMKTIIALS
YIFCLALGQDLPGNDNSTATLCLGHHAVPNGTLVKTITDDQIEVTNATEL
VQSSSTGKICNNPHRILDGIDCTLIDALLGDPHCDVFQNETWDLFVERSK
AFSNCYPYDVPDYASLRSLVASSGTLEFITEGFTWTGVTQNGGSNACKRG
PGSGFFSRLNWLTKSGSTYPVLNVTMPNNDNFDKLYIWGVHHPSTNQEQT
SLYVQASGRVTVSTRRSQQTIIPNIESRPWVRGLSSRISIYWTIVKPGDV
LVINSNGNLIAPRGYFKMRTGKSSIMRSDAPIDTCISECITPNGSIPNDK
PFQNVNKITYGACPKYVKQNTLKLATGMRNVPEKQTRGLFGAIAGFIENG
WEGMIDGWYGFRHQNSEGTGQAADLKSTQAAIDQINGKLNRVIEKTNEKF
HQIEKEFSEVEGRIQDLEKYVEDTKIDLWSYNAELLVALENQHTIDLTDS
EMNKLFEKTRRQLRENAEDMGNGCFKIYHKCDNACIESIRNGTYDHDVYR
DEALNNRFQIKGVELKSGYKDWILWISFAISCFLLCVVLLGFIMWACQRG
NIRCNICIRRKRGSGATNFSLLKQAGDVEENPGPMNPNQKIITIGSVCMT
IGMANLILQIGNIISIWISHSIQLGNQNQIETCNQSVITYENNTWVNQTY
VNISNTNFAAGQSVVSVKLAGNSSLCPVSGWAIYSKDNSVRIGSKGDVFV
IREPFISCSPLECRTFFLTQGALLNDKHSNGTIKDRSPYRTLMSCPIGEV
PSPYNSRFESVAWSASACHDGINWLTIGISGPDNGAVAVLKYNGIITDTI
KSWRNNILRTQESECACVNGSCFTVMTDGPSNGQASYKIFRIEKGKIVKS
VEMNAPNYHYEECSCYPDSSEITCVCRDNWHGSNRPWVSFNQNLEYQIGY
ICSGIFGDNPRPNDKTGSCGPVSSNGANGVKGFSFKYGNGVWIGRTKSIS
SRNGFEMIWDPNGWTGTDNNFSIKQDIVGINEWSGYSGSFVQHPELTGLD
CIRPCFWVELIRGRPKENTIWTSGSSISFCGVNSDTVGWSWPDGAELPFT
IDKRRKRGSGATNFSLLKQAGDVEENPGPMNPNQKIITIGSVSLTIATVC
FLMQIAILVTTVTLHFKQYECDSPASNQVMPCEPIIIERNITEIVYLNNT
TIEKEICPKVVEYRNWSKPQCQITGFAPFSKDNSIRLSAGGDIWVTREPY
VSCDHGKCYQFALGQGTTLDNKHSNDTIHDRIPHRTLLMNELGVPFHLGT
RQVCIAWSSSSCHDGKAWLHVCITGDDKNATASFIYDGRLVDSIGSWSQN
ILRTQESECVCINGTCTVVMTDGSASGRADTRILFIEEGKIVHISPLSGS
AQHVEECSCYPRYPGVRCICRDNWKGSNRPVVDINMEDYSIDSSYVCSGL
VGDTPRNDDRSSNSNCRNPNNERGNQGVKGWAFDNGDDVWMGRTISKDLR
SGYETFKVIGGWSTPNSKSQINRQVIVDSDNRSGYSGIFSVEGKSCINRC
FYVELIRGRKQETRVWWTSNSIVVFCGTSGTYGTGSWPDGANINFMPIRR
KRGSGATNFSLLKQAGDVEENPGPMASQGTKRSYEQMETDGERQNATEIR
ASVGRMIGGIGRFYIQMCTELKLSDYEGRLIQNSITIERMVLSAFDERRN
KYLEEHPSAGKDPKKTGGPIYRRIDGKWMRELILWEKDDIKRIYKQANNG
EDATAGLTHMMIWHSNLNDATYQRTRALVRTGMDPRMCSLMQGSTLPRRS
GAAGAAVKGVGTMVMELIRMIKRGINDRNFWRGENGRRTRIAYERMCNIL
KGKFQTAAQRAMMDQVRESRNPGNAEIEDLIFLARSALILRGSVAHKSCL
PACVYGPAVASGYDFEREGYSLVGIDPFRLLQNSQVYSLIRPNENPAHKS
QLVWMACHSAAFEDLRVSSFIRGTRVVPRGKLSTRGVQIASNENMETMDS
STLELRSRYWAIRTRSGGNTNQQRASAGQISVQPTFSVQRNLPFERATIM
AAFTGNTEGRTRDMRTEIIRMMESARPEDVSFQGRGVFELSDEKATSPIV
```

-continued

PSFDMSNEGSYFFGDNAEEYDNRRKRGSGATNFSLLKQAGDVEENPGPMS

LLTEVETYVLSIVPSGPLKAEIAQRLEDVFAGKNTDLEALMEWLKTRPIL

SPLTKGILGFVFTLTVPSERGLQRRRFVQNALNGNGDPNNMDRAVKLYRK

LKREITFHGAKEVALSYSAGALASCMGLIYNRMGTVTTEVAFGLVCATCE

QIADSQHRSHRQMVTTTNPLIRHENRMVLASTTAKAMEQMAGSSEQAAEA

MEVASQARQMVQAMRTIGTHPSSSAGLKDDLIENLQAYQKRMGVQMQRFK

RRRKRGSGATNFSLLKQAGDVEENPGPMSLLTEVETPTRNEWGCRCNDSSD

PLVIAASIIGILHLILWILDRLFFKCIYRRLKYGLKRGPSTEGVPESMRE

EYRKEQQSAVDVDDGHFVNIELE

Defined sequences of the cleavage sites making up the linkers in the single nucleic acid construct (SEQ ID NO 1) depicted in FIG. 1:

```
5'-part of linker: furin cleavage site, codon
optimized for human; Nucleotide sequence
                                    (SEQ ID NO 3)
CGGCGGAAGCGG Amino acid sequence
                                    (SEQ ID NO 4)
RRKR 3'-part of linker: porcine teschovirus-1 2A
peptide including GSG encoding sequence;
Nucleotide sequence
                                    (SEQ ID NO 5)
GGAAGCGGAGCTACTAACTTCAGCCTGCTGAAGCAGGCTGGAGACGTGGA

GGAGAACCCTGGACCT

Amino acid sequence
                                    (SEQ ID NO 6)
GSGATNFSLLKQAGDVEENPGP Alternative 3'-part of linker; porcine
teschovirus-1 2A peptide, with KasI restriction
enzyme site, including GSG encoding sequence;
nucleotide sequence
                                    (SEQ ID NO 7)
GGAAGCGGCGCCACTAACTTCAGCCTGCTGAAGCAGGCTGGAGACGTGGA

GGAGAACCCTGGACCT

Amino acid sequence; see SEQ ID NO 6
```

Overview of defined influenza protein coding sequences making up the single nucleic acid construct depicted in FIG. 1, with and without modified HA and NP epitopes potentially implicated of playing a role for narcolepsy:

```
Hemagglutinin (HA) synthetic gene, based on acc.
no. FJ966082 (Influenza A virus A/California/04/09
(H1N1)), contains wild type potential narcolepsy-
inducing codon (aac; Asn), codon optimized for
human; Nucleotide sequence (SEQ ID NO 8)
ATGAAGGCTATCCTGGTGGTGCTGCTGTACACCTTCGCCACCGCCAACGC

CGATACCCTGTGCATCGGCTACCACGCCAACAACAGCACCGACACCGTGG

ATACCGTGCTGGAAAAGAACGTGACCGTGACCCACAGCGTGAACCTGCTG

GAAGATAAGCACAACGGCAAGCTGTGCAAGCTGAGAGGCGTGGCCCCTCT

GCACCTGGGCAAGTGCAATATCGCCGGCTGGATCCTGGGCAACCCCGAGT

GCGAGAGCCTGAGCACCGCCAGCTCTTGGTCCTACATCGTGGAGACACCC

AGCAGCGACAACGGCACCTGTTACCCCGGCGACTTCATCGACTACGAGGA

ACTGCGGGAGCAGCTGTCCAGCGTGTCCAGCTTCGAGCGGTTCGAGATCT

TCCCCAAGACCAGCTCCTGGCCCAACCACGACAGCaacAAGGGCGTGACC

GCCGCCTGTCCTCACGCTGGGGCCAAGAGCTTCTACAAGAACCTGATCTG

GCTGGTGAAGAAGGGCAACAGCTACCCCAAGCTGTCCAAGAGCTACATCA

ACGACAAGGGCAAAGAGGTGCTGGTGCTGTGGGGCATCCACCACCCTAGC

ACCAGCGCCGACCAGCAGAGCCTGTACCAGAACGCCGACACCTACGTGTT

CGTGGGCAGCAGCCGGTACAGCAAGAAGTTCAAGCCCGAGATCGCCATCA

GACCCAAAGTGCGGGACCAGGAAGGCCGGATGAACTACTACTGGACCCTG

GTGGAGCCCGGCGACAAGATCACCTTCGAGGCCACCGGCAATCTGGTGGT

GCCCAGATACGCCTTCGCCATGGAAAGAAACGCCGGCAGCGGCATCATCA

TCAGCGACACCCCCGTGCACGACTGCAACACCACCTGTCAGACCCCCAAG

GGGGCCATCAACACCAGCCTGCCCTTCCAGAACATCCACCCCATCACCAT

CGGCAAGTGCCCTAAGTACGTGAAGTCCACCAAGCTGAGACTGGCCACCG

GCCTGCGGAACATCCCCAGCATCCAGAGCAGAGGCCTGTTCGGGGCCATT

GCCGGCTTTATCGAGGGCGGCTGGACCGGAATGGTGGACGGGTGGTACGG

CTACCACCACCAGAATGAGCAGGGCAGCGGCTACGCCGCCGACCTGAAGT

CCACACAGAACGCCATCGACGAGATCACCAACAAAGTGAACAGCGTGATC

GAGAAGATGAACACCCAGTTCACCGCCGTGGGCAAAGAGTTCAACCACCT

GGAAAAGCGGATCGAGAACCTGAACAAGAAGGTGGACGACGGCTTCCTGG

ACATCTGGACCTACAACGCCGAGCTGCTGGTGCTGCTGGAAAACGAGCGG

ACCCTGGACTACCACGACTCCAACGTGAAGAATCTGTACGAGAAAGTGCG

GAGCCAGCTGAAGAACAACGCCAAAGAGATCGGCAACGGCTGCTTCGAGT

TCTACCACAAGTGCGACAACACCTGTATGGAAAGCGTGAAGAACGGCACC

TACGACTACCCCAAGTACAGCGAGGAAGCCAAGCTGAACCGGGAAGAGAT

CGACGGCGTGAAGCTGGAAAGCACCCGGATCTACCAGATCCTGGCCATCT

ACAGCACCGTGGCCAGCTCACTGGTCCTGGTCGTGTCCCTGGGCGCTATC

AGCTTCTGGATGTGCAGCAACGGCAGCCTGCAGTGCCGGATCTGCATC

Amino acid sequence, (SEQ ID NO 9)
MKAILVVLLYTFATANADTLCIGYHANNSTDTVDTVLEKNVTVTHSVNLL

EDKHNGKLCKLRGVAPLHLGKCNIAGWILGNPECESLSTASSWSYIVETP

SSDNGTCYPGDFIDYEELREQLSSVSSFERFEIFPKTSSWPNHDSNKGVT

AACPHAGAKSFYKNLIWLVKKGNSYPKLSKSYINDKGKEVLVLWGIHHPS

TSADQQSLYQNADTYVFVGSSRYSKKFKPEIAIRPKVRDQEGRMNYYWTL

VEPGDKITFEATGNLVVPRYAFAMERNAGSGIIISDTPVHDCNTTCQTPK

GAINTSLPFQNIHPITIGKCPKYVKSTKLRLATGLRNIPSIQSRGLFGAI

AGFIEGGWTGMVDGWYGYHHQNEQGSGYAADLKSTQNAIDEITNKVNSVI

EKMNTQFTAVGKEFNHLEKRIENLNKKVDDGFLDIWTYNAELLVLLENER

TLDYHDSNVKNLYEKVRSQLKNNAKEIGNGCFEFYHKCDNTCMESVKNGT

YDYPKYSEEAKLNREEIDGVKLESTRIYQILAIYSTVASSLVLVVSLGAI

SFWMCSNGSLQCRICI
```

Hemagglutinin (HA) synthetic gene, based on
acc. no FJ966082 (Influenza A virus A/
California/04/09 (H1N1)), contains modified
potential narcolepsy-inducing codon (gat;
Asp), codon optimized for human;
Nucleotide sequence (SEQ ID NO 10)
atgAAGGCTATCCTGGTGGTGCTGCTGTACACCTTCGCCACCGCCAACGC

CGATACCCTGTGCATCGGCTACCACGCCAACAACAGCACCGACACCGTGG

ATACCGTGCTGGAAAAGAACGTGACCGTGACCCACAGCGTGAACCTGCTG

GAAGATAAGCACAACGGCAAGCTGTGCAAGCTGAGAGGCGTGGCCCCTCT

GCACCTGGGCAAGTGCAATATCGCCGGCTGGATCCTGGGCAACCCCGAGT

GCGAGAGCCTGAGCACCGCCAGCTCTTGGTCCTACATCGTGGAGACACCC

AGCAGCGACAACGGCACCTGTTACCCCGGCGACTTCATCGACTACGAGGA

ACTGCGGGAGCAGCTGTCCAGCGTGTCCAGCTTCGAGCGGTTCGAGATCT

TCCCCAAGACCAGCTCCTGGCCCAACCACGACAGCgatAAGGGCGTGACC

GCCGCCTGTCCTCACGCTGGGGCCAAGAGCTTCTACAAGAACCTGATCTG

GCTGGTGAAGAAGGGCAACAGCTACCCCAAGCTGTCCAAGAGCTACATCA

ACGACAAGGGCAAAGAGGTGCTGGTGCTGTGGGGCATCCACCACCCTAGC

ACCAGCGCCGACCAGCAGAGCCTGTACCAGAACGCCGACACCTACGTGTT

CGTGGGCAGCAGCCGGTACAGCAAGAAGTTCAAGCCCGAGATCGCCATCA

GACCCAAAGTGCGGGACCAGGAAGGCCGGATGAACTACTACTGGACCCTG

GTGGAGCCCGGCGACAAGATCACCTTCGAGGCCACCGGCAATCTGGTGGT

GCCCAGATACGCCTTCGCCATGGAAAGAAACGCCGGCAGCGGCATCATCA

TCAGCGACACCCCCGTGCACGACTGCAACACCACCTGTCAGACCCCCAAG

GGGGCCATCAACACCAGCCTGCCCTTCCAGAACATCCACCCCATCACCAT

CGGCAAGTGCCCTAAGTACGTGAAGTCCACCAAGCTGAGACTGGCCACCG

GCCTGCGGAACATCCCCAGCATCCAGAGCAGAGGCCTGTTCGGGGCCATT

GCCGGCTTTATCGAGGGCGGCTGGACCGGAATGGTGGACGGGTGGTACGG

CTACCACCACCAGAATGAGCAGGGCAGCGGCTACGCCGCCGACCTGAAGT

CCACACAGAACGCCATCGACGAGATCACCAACAAAGTGAACAGCGTGATC

GAGAAGATGAACACCCAGTTCACCGCCGTGGGCAAAGAGTTCAACCACCT

GGAAAAGCGGATCGAGAACCTGAACAAGAAGGTGGACGACGGCTTCCTGG

ACATCTGGACCTACAACGCCGAGCTGCTGGTGCTGCTGGAAAACGAGCGG

ACCCTGGACTACCACGACTCCAACGTGAAGAATCTGTACGAGAAAGTGCG

GAGCCAGCTGAAGAACAACGCCAAAGAGATCGGCAACGGCTGCTTCGAGT

TCTACCACAAGTGCGACAACACCTGTATGGAAAGCGTGAAGAACGGCACC

TACGACTACCCCAAGTACAGCGAGGAAGCCAAGCTGAACCGGGAAGAGAT

CGACGGCGTGAAGCTGGAAAGCACCCGGATCTACCAGATCCTGGCCATCT

ACAGCACCGTGGCCAGCTCACTGGTCCTGGTCGTGTCCCTGGGCGCTATC

AGCTTCTGGATGTGCAGCAACGGCAGCCTGCAGTGCCGGATCTGCATC

Amino acid sequence, (SEQ ID NO 11)
MKAILVVLLYTFATANADTLCIGYHANNSTDTVDTVLEKNVTVTHSVNLL

EDKHNGKLCKLRGVAPLHLGKCNIAGWILGNPECESLSTASSWSYIVETP

SSDNGTCYPGDFIDYEELREQLSSVSSFERFEIFPKTSSWPNHDSDKGVT

AACPHAGAKSFYKNLIWLVKKGNSYPKLSKSYINDKGKEVLVLWGIHHPS

TSADQQSLYQNADTYVFVGSSRYSKKFKPEIAIRPKVRDQEGRMNYYWTL

VEPGDKITFEATGNLVVPRYAFAMERNAGSGIIISDTPVHDCNTTCQTPK

GAINTSLPFQNIHPITIGKCPKYVKSTKLRLATGLRNIPSIQSRGLFGAI

AGFIEGGWTGMVDGWYGYHHQNEQGSGYAADLKSTQNAIDEITNKVNSVI

EKMNTQFTAVGKEFNHLEKRIENLNKKVDDGFLDIWTYNAELLVLLENER

TLDYHDSNVKNLYEKVRSQLKNNAKEIGNGCFEFYHKCDNTCMESVKNGT

YDYPKYSEEAKLNREEIDGVKLESTRIYQILAIYSTVASSLVLVVSLGAI

SFWMCSNGSLQCRICI

Hemagglutinin (HA) synthetic gene, based on
acc. no AB295605 (Influenza A virus A/Aichi/
2/1968(H3N2)), codon optimized for human;
Nucleotide sequence (SEQ ID NO 12)
atgAAAACCATCATCGCCCTGAGCTACATCTTCTGCCTCGCCCTCGGCCA

GGACCTGCCCGGCAACGACAACAGCACCGCCACCCTGTGCCTGGGCCACC

ACGCCGTGCCCAACGGCACCCTGGTGAAAACAATTACCGACGACCAGATC

GAGGTGACCAACGCCACCGAGCTGGTGCAGAGCAGCAGCACCGGCAAGAT

CTGCAACAACCCCCACCGCATCCTGGACGGCATCGACTGCACCCTGATCG

ACGCCCTGCTGGGCGACCCTCACTGCGACGTGTTCCAGAACGAGACCTGG

GACCTGTTCGTGGAGCGCAGCAAGGCCTTCAGCAACTGCTACCCCTACGA

CGTGCCCGACTACGCTTCCCTGCGCAGCCTGGTCGCCAGCTCCGGGACCC

TGGAGTTCATCACCGAGGGCTTCACCTGGACCGGGGTCACACAGAATGGG

GGTCCAACGCCTGCAAGCGCGGACCCGGCAGCGGCTTCTTCAGCCGCCT

GAACTGGCTGACCAAGAGCGGCAGCACCTACCCCGTGCTGAACGTGACCA

TGCCCAACAACGACAACTTCGACAAGCTGTACATCTGGGGCGTGCACCAC

CCCAGCACCAACCAGGAACAGACCAGCCTGTACGTGCAGGCCAGCGGCAG

GGTGACCGTGAGCACCCGCCGCAGCCAGCAGACCATCATCCCCAACATCG

AGTCCCGGCCCTGGGTCCGCGGGCTGTCCAGCCGCATCAGCATCTACTGG

ACCATCGTGAAGCCCGGCGACGTGCTGGTGATCAACAGCAACGGCAACCT

GATCGCCCCCAGGGGCTACTTCAAGATGCGGACCGGCAAGAGCAGCATCA

TGCGCAGCGACGCCCCCATCGACACCTGCATCAGCGAGTGCATCACCCCC

AACGGCAGCATCCCCAACGACAAGCCCTTCCAGAACGTGAACAAGATCAC

CTACGGGGCCTGTCCTAAGTACGTGAAGCAGAACACCCTGAAGCTCGCTA

CCGGCATGCGGAACGTGCCCGAGAAGCAGACCAGGGGCCTGTTCGGGGCC

ATCGCCGGCTTCATCGAGAACGGCTGGGAGGGCATGATCGACGGGTGGTA

TGGCTTCCGCCACCAGAACAGCGAGGGCACCGGCCAGGCCGCCGACCTGA

AGAGCACCCAGGCCGCCATCGACCAGATCAACGGCAAGCTGAACCGCGTG

ATCGAGAAAACCAACGAGAAGTTCCACCAGATCGAGAAAGAGTTCAGCGA

GGTCGAGGGCCGCATCCAGGACCTGGAGAAGTACGTGGAGGACACCAAGA

TCGACCTGTGGAGCTACAACGCCGAGCTGCTGGTCGCCCTGGAGAACCAG

CACACCATCGACCTGACCGACAGCGAGATGAACAAGCTGTTCGAGAAAAC

CCGCAGGCAGCTGCGCGAGAACgCCGAGGACATGGGCAACGGCTGCTTCA

AGATCTACCACAAGTGCGACAACGCCTGCATCGAGAGCATCCGCAACGGC

-continued

ACCTACGACCACGACGTGTACCGCGACGAGGCCCTGAACAACCGCTTCCA

GATCAAGGGCGTGGAGCTGAAGAGCGGCTACAAGGACTGGATCCTGTGGA

TCAGCTTCGCTATCAGCTGCTTCCTGCTGTGCGTGGTGCTGCTGGGCTTC

ATCATGTGGGCCTGCCAGCGGGGCAACATCCGCTGCAACATCTGCATC

Amino acid sequence (SEQ ID NO 13)

MKTIIALSYIFCLALGQDLPGNDNSTATLCLGHHAVPNGTLVKTITDDQI

EVTNATELVQSSSTGKICNNPHRILDGIDCTLIDALLGDPHCDVFQNETW

DLFVERSKAFSNCYPYDVPDYASLRSLVASSGTLEFITEGFTWTGVTQNG

GSNACKRGPGSGFFSRLNWLTKSGSTYPVLNVTMPNNDNFDKLYIWGVHH

PSTNQEQTSLYVQASGRVTVSTRRSQQTIIPNIESRPWVRGLSSRISIYW

TIVKPGDVLVINSNGNLIAPRGYFKMRTGKSSIMRSDAPIDTCISECITP

NGSIPNDKPFQNVNKITYGACPKYVKQNTLKLATGMRNVPEKQTRGLFGA

IAGFIENGWEGMIDGWYGFRHQNSEGTGQAADLKSTQAAIDQINGKLNRV

IEKTNEKFHQIEKEFSEVEGRIQDLEKYVEDTKIDLWSYNAELLVALENQ

HTIDLTDSEMNKLFEKTRRQLRENAEDMGNGCFKIYHKCDNACIESIRNG

TYDHDVYRDEALNNRFQIKGVELKSGYKDWILWISFAISCFLLCVVLLGF

IMWACQRGNIRCNICI

Neuraminidase (NA) synthetic gene, based on acc. no FJ966084 (Influenza A virus A/California/04/09(H1N1)), codon optimized for human;

Nucleotide sequence (SEQ ID NO 14)

ATGAACCCCAACCAGAAGATCATCACCATCGGCAGCGTGTGCATGACCAT

CGGCATGGCCAACCTGATCCTGCAGATCGGCAACATCATCAGCATCTGGA

TCAGCCACAGCATCCAGCTGGGCAACCAGAACCAGATCGAGACATGCAAC

CAGAGCGTGATCACCTACGAGAACAACACCTGGGTGAACCAGACCTACGT

GAACATCAGCAACACCAACTTCGCCGCTGGCCAGAGCGTGGTGTCTGTGA

AGCTGGCCGGCAACAGCAGCCTGTGCCCTGTGTCCGGCTGGGCCATCTAC

AGCAAGGACAACAGCGTGCGGATCGGCAGCAAGGGCGACGTGTTCGTGAT

CCGGGAGCCCTTCATCAGCTGCAGCCCCCTGGAATGCCGGACCTTCTTCC

TGACCCAGGGGGCCCTGCTGAACGACAAGCACAGCAACGGCACCATCAAG

GACAGAAGCCCCTACCGGACCCTGATGAGCTGCCCCATCGGCGAGGTGCC

CAGCCCCTACAACAGCAGATTCGAGTCCGTGGCTTGGAGCGCCTCTGCCT

GCCACGACGGCATCAACTGGCTGACAATCGGCATCAGCGGCCCTGATAAC

GGCGCTGTGGCCGTGCTGAAGTACAACGGCATCATCACCGACACAATCAA

GAGCTGGCGGAACAACATCCTGCGGACCCAGGAATCCGAGTGCGCCTGCG

TGAACGGCAGCTGCTTCACCGTGATGACCGACGGCCCTAGCAATGGCCAG

GCCAGCTACAAGATCTTCCGGATCGAGAAGGGCAAGATCGTGAAGTCCGT

GGAGATGAACGCCCCCAACTACCACTACGAGGAATGCAGCTGCTACCCCG

ACAGCAGCGAGATCACCTGTGTGTGCCGGGACAACTGGCACGGCAGCAAC

AGACCCTGGGTGTCCTTCAACCAGAATCTGGAATACCAGATCGGCTACAT

TTGCAGCGGCATCTTCGGCGACAACCCCAGACCCAACGACAAGACCGGAA

GCTGCGGCCCTGTGTCTAGCAACGGGGCCAACGGCGTGAAGGGCTTCAGC

TTCAAGTACGGCAATGGCGTGTGGATCGGCCGGACCAAGAGCATCAGCAG

-continued

CCGGAACGGCTTCGAGATGATCTGGGACCCCAACGGCTGGACCGGCACCG

ACAACAACTTCAGCATCAAGCAGGACATCGTGGGCATCAACGAGTGGAGC

GGCTACAGCGGCAGCTTCGTGCAGCACCCTGAGCTGACCGGCCTGGACTG

CATCCGGCCCTGCTTTTGGGTGGAGCTGATCAGAGGCAGACCCAAAGAGA

ACACCATCTGGACCAGCGGCAGCAGCATCAGCTTTTGCGGCGTGAACAGC

GACACCGTGGGCTGGTCTTGGCCCGATGGGGCCGAGCTGCCCTTCACCAT

CGACAAG

Amino acid sequence (SEQ ID NO 15)

MNPNQKIITIGSVCMTIGMANLILQIGNIISIWISHSIQLGNQNQIETCN

QSVITYENNTWVNQTYVNISNTNFAAGQSVVSVKLAGNSSLCPVSGWAIY

SKDNSVRIGSKGDVFVIREPFISCSPLECRTFFLTQGALLNDKHSNGTIK

DRSPYRTLMSCPIGEVPSPYNSRFESVAWSASACHDGINWLTIGISGPDN

GAVAVLKYNGIITDTIKSWRNNILRTQESECACVNGSCFTVMTDGPSNGQ

ASYKIFRIEKGKIVKSVEMNAPNYHYEECSCYPDSSEITCVCRDNWHGSN

RPWVSFNQNLEYQIGYICSGIFGDNPRPNDKTGSCGPVSSNGANGVKGFS

FKYGNGVWIGRTKSISSRNGFEMIWDPNGWTGTDNNFSIKQDIVGINEWS

GYSGSFVQHPELTGLDCIRPCFWVELIRGRPKENTIWTSGSSISFCGVNS

DTVGWSWPDGAELPFTIDK

Neuraminidase (NA) synthetic gene, based on acc. no AB295606 Influenza A virus (A/Aichi/2/1968(H3N2)), codon optimized for human;

Nucleotide sequence (SEQ ID NO 16)

atgAACCCCAACCAGAAGATCATCACCATCGGCAGCGTGAGCCTGACAAT

CGCTACCGTGTGCTTCCTGATGCAGATCGCCATCCTGGTGACCACCGTGA

CCCTGCACTTCAAGCAGTACGAGTGCGACAGCCCCGCCAGCAACCAGGTC

ATGCCCTGCGAGCCCATCATCATCGAGCGCAACATCACCGAGATCGTGTA

CCTGAACAACACCACCATCGAGAAGGAAATCTGCCCCAAGGTCGTGGAGT

ACCGCAACTGGTCCAAGCCCCAGTGCCAGATCACCGGCTTCGCCCCCTTC

AGCAAGGACAACAGCATCCGCCTGAGCGCCGGAGGGGACATCTGGGTCAC

CCGCGAGCCCTACGTGAGCTGCGACCACGGCAAGTGCTACCAGTTCGCTC

TGGGGCAGGGGACAACACTCGATAACAAGCACAGCAACGACACCATCCAC

GACCGCATCCCCCACCGCACCCTGCTGATGAACGAGCTGGGCGTGCCCTT

CCACCTGGGCACCCGCCAGGTCTGCATCGCCTGGTCCAGCAGCAGCTGCC

ACGACGGCAAGGCCTGGCTGCACGTGTGCATCACCGGCGACGACAAGAAC

GCCACCGCCAGCTTCATCTACGACGGCCGCCTGGTGGACAGCATCGGCAG

CTGGTCCCAGAACATCCTGCGCACCCAAGAAAGCGAGTGCGTCTGCATCA

ACGGGACCTGCACCGTGGTGATGACCGATGGAAGCGCCAGCGGCAGGGCC

GATACCCGGATCCTGTTCATCGAGGAAGGCAAGATCGTGCACATCAGCCC

TCTCAGCGGCTCCGCCCAGCACGTGGAAGAGTGCAGCTGCTACCCCCGCT

ACCCCGGCGTGCGCTGCATCTGCCGCGACAACTGGAAGGGCAGCAACCGC

CCCGTGGTGGACATCAACATGGAGGACTACAGCATCGACAGCAGCTACGT

GTGCAGCGGCCTGGTCGGCGACACACCCCGCAACGACGACCGCAGCAGCA

ACAGCAACTGCCGCAACCCCAACAACGAGCGCGGCAACCAGGGCGTGAAG

-continued
GGCTGGGCCTTCGACAACGGCGACGACGTGTGGATGGGCCGCACCATCTC

CAAGGACCTGCGCAGCGGCTACGAGACCTTCAAGGTGATCGGCGGGTGGA

GCACCCCCAACAGCAAGAGCCAGATCAACCGCCAGGTGATCGTGGACAGC

GACAACCGCTCCGGCTACAGCGGCATCTTCAGCGTGGAGGGCAAGTCCTG

CATCAACCGCTGCTTCTACGTGGAGCTGATCCGCGGCAGGAAGCAAGAAA

CCCGCGTCTGGTGGACCAGCAACTCCATCGTGGTGTTCTGCGGCACCAGC

GGCACCTACGGCACCGGCAGCTGGCCCGACGGGGCCAACATCAACTTCAT

GCCCATC

Amino acid sequence (SEQ ID NO 17)
MNPNQKIITIGSVSLTIATVCFLMQIAILVTTVTLHFKQYECDSPASNQV

MPCEPIIIERNITEIVYLNNTTIEKEICPKVVEYRNWSKPQCQITGFAPF

SKDNSIRLSAGGDIWVTREPYVSCDHGKCYQFALGQGTTLDNKHSNDTIH

DRIPHRTLLMNELGVPFHLGTRQVCIAWSSSSCHDGKAWLHVCITGDDKN

ATASFIYDGRLVDSIGSWSQNILRTQESECVCINGTCTVVMTDGSASGRA

DTRILFIEEGKIVHISPLSGSAQHVEECSCYPRYPGVRCICRDNWKGSNR

PVVDINMEDYSIDSSYVCSGLVGDTPRNDDRSSNSNCRNPNNERGNQGVK

GWAFDNGDDVWMGRTISKDLRSGYETFKVIGGWSTPNSKSQINRQVIVDS

DNRSGYSGIFSVEGKSCINRCFYVELIRGRKQETRVWWTSNSIVVFCGTS

GTYGTGSWPDGANINFMPI

Nucleoprotein (NP) synthetic gene, based on acc.
no. AY744935 (Influenza A virus A/Brevig Mission/
1/1918 (H1N1)), including wild type potential
narcolepsy-inducing epitope, codon optimized for
human; nucleotide sequence (SEQ ID NO 18)
ATGGCCAGCCAGGGCACCAAGAGAAGCTACGAGCAGATGGAAACCGACGG

CGAGAGGCAGAACGCCACCGAGATCAGGGCCAGCGTGGGCAGGATGATCG

GCGGCATCGGCAGGTTCTACATCCAGATGTGCACCGAGCTGAAGCTGTCC

GACTACGAGGGCAGGCTGATCCAGAACAGCATCACCATCGAGAGGATGGT

GCTGTCCGCCTTCGACGAGAGAAGAAACAAGTACCTGGAAGAGCACCCCA

GCGCCGGCAAGGACCCCAAGAAAACCGGCGGACCCATCTACAGAAGGATC

GACGGCAAGTGGATGAGAGAGCTGATCCTGTACGACAAGGAGGAAATCAG

AAGGATCTGGCGGCAGGCCAACAACGGCGAGGACGCCACAGCCGGCCTGA

CCCACATGATGATCTGGCACAGCAACCTGAACGACGCCACCTACCAGAGG

ACCAGGGCCCTCGTCAGAACCGGCATGGACCCCCGGATGTGCAGCCTGAT

GCAGGGCAGCACACTGCCCAGAAGAAGCGGAGCTGCTGGAGCCGCCGTGA

AGGGCGTGGGCACCATGGTGATGGAACTGATCAGGATGATCAAGAGGGGC

ATCAACGACAGGAACTTTTGGAGGGGCGAGAACGGCAGAAGGACCAGGAT

CGCCTACGAGGATGTGCAACATCCTGAAGGGCAAGTTCCAGACAGCCG

CCCAGAGGGCCATGATGGACCAGGTCCGGGAGAGCAGGAACCCCGGCAAC

GCCGAGATCGAGGACCTGATCTTCCTGGCCAGAAGCGCCCTGATCCTGAG

GGGCAGCGTGGCCCACAAGAGCTGCCTGCCCGCCTGCGTGTACGGACCCG

CCGTGGCCAGCGGCTACGACTTCGAGAGAGAGGGCTACAGCCTGGTCGGC

ATCGACCCCTTCAGGCTGCTGCAGAACTCCCAGGTGTACTCTCTGATCAG

GCCCAACGAGAACCCCGCCCACAAGTCCCAGCTGGTCTGGATGGCCTGCC

ACAGCGCCGCCTTCGAGGATCTGAGAGTGAGCAGCTTCATCAGGGGCACC

AGAGTGGTGCCCAGGGGCAAGCTGTCCACCAGGGGCGTGCAGATCGCCAG

CAACGAGAACATGGAAACCATGGACAGCAGCACCCTGGAACTGAGAAGCA

GGTACTGGGCCATCAGGACCAGAAGCGGCGGCAACACCAACCAGCAGAGG

GCCAGCGCCGGACAGATCAGCGTGCAGCCCACCTTCTCCGTGCAGAGGAA

CCTGCCCTTCGAGAGGGCCACCATCATGGCCGCCTTCACCGGCAACACCG

AGGGCAGGACCAGAGACATGAGGACCGAGATCATCAGAATGATGGAAAGC

GCCAGGCCCGAGGACGTGAGCTTCCAGGGCAGGGGCGTGTTCGAGCTGTC

CGATGAGAAGGCCACCTCCCCCATCGTGCCCAGCTTCGACATGAGCAACG

AGGGCAGCTACTTCTTCGGCGACAACGCCGAGGAATACGACAAC

Amino acid sequence (SEQ ID NO 19)
MASQGTKRSYEQMETDGERQNATEIRASVGRMIGGIGRFYIQMCTELKLS

DYEGRLIQNSITIERMVLSAFDERRNKYLEEHPSAGKDPKKTGGPIYRRI

DGKWMRELILYDKEEIRRIWRQANNGEDATAGLTHMMIWHSNLNDATYQR

TRALVRTGMDPRMCSLMQGSTLPRRSGAAGAAVKGVGTMVMELIRMIKRG

INDRNFWRGENGRRTRIAYERMCNILKGKFQTAAQRAMMDQVRESRNPGN

AEIEDLIFLARSALILRGSVAHKSCLPACVYGPAVASGYDFEREGYSLVG

IDPFRLLQNSQVYSLIRPNENPAHKSQLVWMACHSAAFEDLRVSSFIRGT

RVVPRGKLSTRGVQIASNENMETMDSSTLELRSRYWAIRTRSGGNTNQQR

ASAGQISVQPTFSVQRNLPFERATIMAAFTGNTEGRTRDMRTEIIRMMES

ARPEDVSFQGRGVFELSDEKATSPIVPSFDMSNEGSYFFGDNAEEYDN

Nucleoprotein (NP) synthetic gene, based on acc.
no. AY744935 (Influenza A virus A/Brevig Mission/
1/1918 (H1N1)), with modified potential
narcolepsy-inducing epitope, codon optimized for
human; Nucleotide sequence (SEQ ID NO 20)
atgGCCAGCCAGGGCACCAAGAGAAGCTACGAGCAGATGGAAACCGACGG

CGAGAGGCAGAACGCCACCGAGATCAGGGCCAGCGTGGGCAGGATGATCG

GCGGCATCGGCAGGTTCTACATCCAGATGTGCACCGAGCTGAAGCTGTCC

GACTACGAGGGCAGGCTGATCCAGAACAGCATCACCATCGAGAGGATGGT

GCTGTCCGCCTTCGACGAGAGAAGAAACAAGTACCTGGAAGAGCACCCCA

GCGCCGGCAAGGACCCCAAGAAAACCGGCGGACCCATCTACAGAAGGATC

GACGGCAAGTGGATGAGAGAGCTGATCCTgtgggagaaggacgacatcaa gcggatctacaagCAGGCCAACAACGGCGAGGACGCCACAGCCGGCCTGA

CCCACATGATGATCTGGCACAGCAACCTGAACGACGCCACCTACCAGAGG

ACCAGGGCCCTCGTCAGAACCGGCATGGACCCCCGGATGTGCAGCCTGAT

GCAGGGCAGCACACTGCCCAGAAGAAGCGGAGCTGcTGGAGCCGCCGTGA

AGGGCGTGGGCACCaTGGTGATGGAACTGATCAGGATGATCAAGAGGGGC

ATCAaCGACAGGAACTTTTGGAGGGGCGAGAACGGCAGAAGGACCAGGAT

CGCCTACGAGGATGTGCAACATCCTGAAGGGCAAGTTCCAGACAGCCG

CCCAGAGGGCCATGATGGACCAGGTCCGGGAGAGCAGGAACCCCGGCAAC

GCCGAGATCGAGGACCTGATcTTCCTGGCCAGAAGCGCCCTGATCCTGAG

GGGCAGCGTGGCCCACAAGAGCTGCCTGCCCGCCTGCGTGTACGGACCCG

-continued

CCGTGGCCAGCGGCTACGACTTCGAGAGAGAGGGCTACAGCCTGGTCGGC
ATCGACCCCTTCAGGCTGCTGCAGAACTCCCAGGTGTACTCTCTGATCAG
GCCCAACGAGAACCCCGCCCACAAGTCCCAGCTGGTCTGGATGGCCTGCC
ACAGCGCCGCCTTCGAGGATCTGAGAGTGAGCAGCTTCATCAGGGGCACC
AGAGTGGTGCCCAGGGGCAAGCTGTCCACCAGGGGCGTGCAGATCGCCAG
CAACGAGAACATGGAAACCATGGACAGCAGCACCCTGGAACTGAGAAGCA
GGTACTGGGCCATCAGGACCAGAAGCGGCGGCAACACCAACCAGCAGAGG
GCCAGCGCCGGACAGATCAGCGTGCAGCCCACCTTCTCCGTGCAGAGGAA
CCTGCCCTTCGAGAGGGCCACCATCATGGCCGCCTTCACCGGCAACACCG
AGGGCAGGACCAGAGACATGAGGACCGAGATCATCAGAATGATGGAAAGC
GCCAGGCCCGAGGACGTGAGCTTCCAGGGCAGGGGCGTGTTCGAGCTGTC
CGATGAGAAGGCCACCTCCCCCATCGTGCCCAGCTTCGACATGAGCAACG
AGGGCAGCTACTTCTTCGGCGACAACGCCGAGGAATACGACAAC
Amino acid sequence (SEQ ID NO 21)
MASQGTKRSYEQMETDGERQNATEIRASVGRMIGGIGRFYIQMCTELKLS
DYEGRLIQNSITIERMVLSAFDERRNKYLEEHPSAGKDPKKTGGPIYRRI
DGKWMRELILWEKDDIKRIYKQANNGEDATAGLTHMMIWHSNLNDATYQR
TRALVRTGMDPRMCSLMQGSTLPRRSGAAGAAVKGVGTMVMELIRMIKRG
INDRNFWRGENGRRTRIAYERMCNILKGKFQTAAQRAMMDQVRESRNPGN
AEIEDLIFLARSALILRGSVAHKSCLPACVYGPAVASGYDFEREGYSLVG
IDPFRLLQNSQVYSLIRPNENPAHKSQLVWMACHSAAFEDLRVSSFIRGT
RVVPRGKLSTRGVQIASNENMETMDSSTLELRSRYWAIRTRSGGNTNQQR
ASAGQISVQPTFSVQRNLPFERATIMAAFTGNTEGRTRDMRTEIIRMMES
ARPEDVSFQGRGVFELSDEKATSPIVPSFDMSNEGSYFFGDNAEEYDN

M1 synthetic gene, based on genomic sequence for acc. no. AY130766 (Influenza A virus A/Brevig mission/1/1918 (H1N1)), encoding codon optimized alternative splice variant M1;
Nucleotide sequence (SEQ ID NO 22)
ATGTCCCTGCTGACAGAGGTGGAGACCTACGTGCTGTCCATCGTGCCCTC

TGGCCCTCTGAAGGCCGAGATCGCCCAGAGACTGGAGGACGTGTTCGCCG

GCAAGAACACAGATCTGGAGGCCCTGATGGAGTGGCTGAAGACAAGGCCA

ATCCTGTCTCCCCTGACCAAGGGCATCCTGGGCTTCGTGTTTACACTGAC

CGTGCCTAGCGAGAGGGGACTGCAGCGGAGAAGGTTCGTGCAGAATGCCC

TGAACGGCAATGGCGACCCAAACAATATGGATCGGGCCGTGAAGCTGTAT

AGAAAGCTGAAGAGGGAGATCACCTTTCACGGAGCCAAGGAGGTGGCCCT

GTCTTACAGCGCCGGGGCCCTGGCAAGCTGCATGGGACTGATCTATAACA

GGATGGGCACAGTGACCACAGAGGTGGCCTTCGGCCTGGTGTGCGCAACC

TGTGAGCAGATCGCAGACAGCCAGCACCGCTCCCACAGGCAGATGGTGAC

CACAACCAACCCCCTGATCCGCCACGAGAATCGGATGGTGCTGGCCTCCA

CAACCGCCAAGGCCATGGAGCAGATGGCAGGCAGCTCCGAGCAGGCAGCA

GAGGCCATGGAGGTGGCCTCTCAGGCCAGACAGATGGTGCAGGCCATGAG

GACAATCGGAACCCACCCTTCTAGCTCCGCCGGCCTGAAGGACGATCTGA

-continued

TCGAGAATCTGCAGGCCTACCAGAAGCGCATGGGCGTGCAGATGCAGCGG

TTTAAG

Amino acid sequence; see SEQ ID NO 23
MSLLTEVETYVLSIVPSGPLKAEIAQRLEDVFAGKNTDLEALMEWLKTRP

ILSPLTKGILGFVFTLTVPSERGLQRRRFVQNALNGNGDPNNMDRAVKLY

RKLKREITFHGAKEVALSYSAGALASCMGLIYNRMGTVTTEVAFGLVCAT

CEQIADSQHRSHRQMVTTTNPLIRHENRMVLASTTAKAMEQMAGSSEQAA

EAMEVASQARQMVQAMRTIGTHPSSSAGLKDDLIENLQAYQKRMGVQMQR

FK

M2 synthetic gene, based on genomic sequence for acc. no. AY130766 (Influenza A virus A/Brevig mission/1/1918 (H1N1)), encoding codon optimized alternative splice variant M2;
Nucleotide sequence (SEQ ID NO 24)
ATGTCCCTGCTGACCGAGGTGGAGACCCCAACACGGAACGAGTGGGGCTG

CAGATGTAATGACAGCTCCGATCCCCTGGTCATCGCCGCCTCTATCATCG

GCATCCTGCACCTGATCCTGTGGATCCTGGACAGGCTGTTCTTTAAGTGC

ATCTACCGGAGACTGAAGTATGGCCTGAAGAGAGGCCCCTCTACAGAGGG

CGTGCCTGAGAGCATGAGGGAGGAGTACCGCAAGGAGCAGCAGAGCGCCG

TGGATGTGGACGATGGCCACTTCGTGAACATCGAGCTGGAG

Amino acid sequence; see SEQ ID NO 25
MSLLTEVETPTRNEWGCRCNDSSDPLVIAASIIGILHLILWILDRLFFKC

IYRRLKYGLKRGPSTEGVPESMREEYRKEQQSAVDVDDGHFVNIELE

SEQ ID NOs: 26-29 - amino acid sequences of self-cleaving 2A peptide motifs

SEQ ID NO: 26:
APVKQTLNFDLLKLAGDVESNPGP

SEQ ID NO: 27:
ATNFSLLKQAGDVEENPGP

SEQ ID NO: 28:
QCTNYALLKLAGDVESNPGP

SEQ ID NO: 29:
EGRGSLLTCGDVEENPGP

SEQ ID NO: 30:
GCCACC (Kozak sequence)

Hence the invention is exemplified by SEQ ID NO 1 (depicted in FIG. 1) which is a construction made up of the following sequences:
KOZAK (SEQ ID NO: 30) - SEQ ID NO 10 - SEQ ID NO 3 - SEQ ID NO 5 - SEQ ID NO 12 - SEQ ID NO 3 - SEQ ID NO 5 - SEQ ID NO 14 - SEQ ID NO 3 - SEQ ID NO 5 - SEQ ID NO 16 - SEQ ID NO 3 - SEQ ID NO 7 - SEQ ID NO 20 - SEQ ID NO 3 - SEQ ID NO 7 - SEQ ID NO 22 - SEQ ID NO 3 - SEQ ID NO 5 - SEQ ID NO 24 - STOP.

The invention claimed is:

1. A nucleotide sequence comprising one or more influenza genes encoding haemagglutinin (HA) and one or more influenza genes encoding neuraminidase (NA), said influenza genes being connected by linkers each comprising at least one cleavage site,
  wherein the one or more influenza genes encoding haemagglutinin (HA) are selected from:
  (i) SEQ ID NO:10 or SEQ ID NO:12, or
  (ii) a nucleic acid sequence having at least 80% sequence identity to SEQ ID NO:10 or SEQ ID NO:12,
  wherein the one or more influenza genes encoding neuraminidase (NA) are selected from:
  (iii) SEQ ID NO:14 or SEQ ID NO:16, or
  (iv) a nucleic acid sequence having at least 80% sequence identity to SEQ ID NO:14 or SEQ ID NO:16,
  wherein any amino acid sequence resulting from the nucleic acid sequences of (ii) and (iv) are immunogenic.

2. The nucleotide sequence according to claim 1, wherein the linkers each comprises a self-cleaving 2A peptide or a furin cleavage site.

3. The nucleotide sequence according to claim 1, wherein the linkers each comprises a self-cleaving 2A peptide.

4. The nucleotide sequence according to claim 1, wherein the linkers each comprises at least two cleavage sites.

5. The nucleotide sequence according to claim 1, wherein the linkers each comprises a furin cleavage site and a self-cleaving 2A peptide.

6. The nucleotide sequence according to claim 5, wherein the linkers each comprise a GSG peptide between the furin cleavage site and the self-cleaving 2A peptide.

7. The nucleotide sequence according to claim 2, wherein the furin cleavage site comprises the nucleotide sequence according to SEQ ID NO:3.

8. The nucleotide sequence according to claim 1, wherein the linkers each comprises SEQ ID NO:5 or SEQ ID NO:7.

9. The nucleotide sequence according to claim 1, wherein the nucleotide sequence further comprises one or more influenza genes encoding matrix proteins selected from matrix protein 1 (M1) and matrix protein 2 (M2).

10. The nucleotide sequence according to claim 1, wherein the nucleotide sequence further comprises an influenza gene encoding nucleoprotein (NP).

11. The nucleotide sequence according to claim 9, wherein the one or more influenza genes encoding matrix proteins are selected from:
  (i) SEQ ID NO:22 or SEQ ID NO:24, or
  (ii) a nucleic acid sequence having at least 80% sequence identity to SEQ ID NO:22 or SEQ ID NO:24,
  wherein the amino acid sequences resulting from the nucleic acid sequences of (ii) are immunogenic.

12. The nucleotide sequence according to claim 10, wherein
  the influenza gene encoding nucleoprotein (NP) are selected from:
  (i) SEQ ID NO:20, or
  (ii) a nucleic acid sequence having at least 80% sequence identity to SEQ ID NO:20,
  wherein the amino acid sequences resulting from the nucleic acid sequences of (ii) are immunogenic.

13. The nucleotide sequence according to claim 1, wherein the nucleotide sequence comprises:
  (i) SEQ ID NO:10 and SEQ ID NO:14, or
  (ia) nucleic acid sequences having at least 80% sequence identity to SEQ ID NO:10 and SEQ ID NO:14, or
  (ii) SEQ ID NO:12 and SEQ ID NO:16, or
  (iia) nucleic acid sequences having at least 80% sequence identity to SEQ ID NO:12 and SEQ ID NO:16, or
  (iii) SEQ ID NO:22, SEQ ID NO:24 and SEQ ID NO:20, or
  (iiia) nucleic acid sequences having at least 80% sequence identity to SEQ ID NO:22, SEQ ID NO:24 and SEQ ID NO:20,
  wherein the amino acid sequences resulting from the nucleic acid sequences of (ia), (iia) and (iiia) are immunogenic.

14. The nucleotide sequence according to claim 1, wherein the nucleotide sequence comprises:
  (i) SEQ ID NO:10 and SEQ ID NO:14, or
  (ia) nucleic acid sequences having at least 80% sequence identity to SEQ ID NO:10 and SEQ ID NO:14, and
  (ii) SEQ ID NO:12 and SEQ ID NO:16, or
  (iia) nucleic acid sequences having at least 80% sequence identity to SEQ ID NO:12 and SEQ ID NO:16,
  wherein the amino acid sequences resulting from the nucleic acid sequences of (ia) and (iia) are immunogenic.

15. The nucleotide sequence according to claim 1, wherein the nucleotide sequence comprises:
   (i) SEQ ID NO:10 and SEQ ID NO:14, or
   (ia) nucleic acid sequences having at least 80% sequence identity to SEQ ID NO:10 and SEQ ID NO:14, and
   (ii) SEQ ID NO:12 and SEQ ID NO:16, or
   (iia) nucleic acid sequences having at least 80% sequence identity to SEQ ID NO:12 and SEQ ID NO:16, and
   (iii) SEQ ID NO:22, SEQ ID NO:24 and SEQ ID NO:20, or
   (iiia) nucleic acid sequences having at least 80% sequence identity to SEQ ID NO:22, SEQ ID NO:24 and SEQ ID NO:20,
   wherein the amino acid sequences resulting from the nucleic acid sequences of (ia), (iia) and (iiia) are immunogenic.

16. The nucleotide sequence according to claim 1, wherein SEQ ID NO:10 is replaced by SEQ ID NO:8.

17. The nucleotide sequence according to claim 12, wherein SEQ ID NO:20 is replaced by SEQ ID NO:18.

18. The nucleotide sequence according claim 1, wherein the nucleotide sequence comprises SEQ ID NO:1 or a nucleic acid sequence having at least 80% sequence identity to SEQ ID NO:1.

19. The nucleotide sequence according claim 1, wherein the nucleotide sequence is incorporated into an expression vector.

20. The nucleotide sequence according to claim 1, wherein the nucleotide sequence is expressed and cleaved at each cleavage site in vivo in a subject to provide the individual antigenic peptides encoded by said influenza genes.

* * * * *

SEQUENCE LISTING

<160> NUMBER OF SEQ ID NOS: 37

<210> SEQ ID NO 1
<211> LENGTH: 9228
<212> TYPE: DNA
<213> ORGANISM: Influenza A virus

<400> SEQUENCE: 1
gccaccatga aggctatcct ggtggtgctg ctgtacacct tcgccaccgc caacgccgat 60
accctgtgca tcggctacca cgccaacaac agcaccgaca ccgtggatac cgtgctggaa 120
aagaacgtga ccgtgaccca cagcgtgaac ctgctggaag ataagcacaa cggcaagctg 180
tgcaagctga gaggcgtggc ccctctgcac ctgggcaagt gcaatatcgc cggctggatc 240
ctgggcaacc ccgagtgcga gagcctgagc accgccagct cttggtccta catcgtggag 300
acacccagca gcgacaacgg cacctgttac cccggcgact tcatcgacta cgaggaactg 360
cgggagcagc tgtccagcgt gtccagcttc gagcggttcg agatcttccc caagaccagc 420
tcctggccca accacgacag cgataagggc gtgaccgccg cctgtcctca cgctggggcc 480
aagagcttct acaagaacct gatctggctg gtgaagaagg gcaacagcta ccccaagctg 540
tccaagagct acatcaacga caagggcaaa gaggtgctgg tgctgtgggg catccaccac 600
cctagcacca gcgccgacca gcagagcctg taccagaacg ccgacaccta cgtgttcgtg 660
ggcagcagcc ggtacagcaa gaagttcaag cccgagatcg ccatcagacc caaagtgcgg 720
gaccaggaag gccggatgaa ctactactgg accctggtgg agcccggcga caagatcacc 780
ttcgaggcca ccggcaatct ggtggtgccc agatacgcct tcgccatgga aagaaacgcc 840
ggcagcggca tcatcatcag cgacaccccc gtgcacgact gcaacaccac ctgtcagacc 900
cccaaggggg ccatcaacac cagcctgccc ttccagaaca tccaccccat caccatcggc 960
aagtgcccta agtacgtgaa gtccaccaag ctgagactgg ccaccggcct gcggaacatc 1020
cccagcatcc agagcagagg cctgttcggg gccattgccg gctttatcga gggcggctgg 1080
accggaatgg tggacgggtg gtacggctac caccaccaga atgagcaggg cagcggctac 1140
gccgccgacc tgaagtccac acagaacgcc atcgacgaga tcaccaacaa agtgaacagc 1200
gtgatcgaga agatgaacac ccagttcacc gccgtgggca aagagttcaa ccacctggaa 1260
aagcggatcg agaacctgaa caagaaggtg gacgacggct tcctggacat ctggacctac 1320
aacgccgagc tgctggtgct gctggaaaac gagcggaccc tggactacca cgactccaac 1380
gtgaagaatc tgtacgagaa agtgcggagc cagctgaaga acaacgccaa agagatcggc 1440
aacggctgct tcgagttcta ccacaagtgc gacaacacct gtatggaaag cgtgaagaac 1500
ggcacctacg actaccccaa gtacagcgag gaagccaagc tgaaccggga agagatcgac 1560
ggcgtgaagc tggaaagcac ccggatctac cagatcctgg ccatctacag caccgtggcc 1620
agctcactgg tcctggtcgt gtccctgggc gctatcagct tctggatgtg cagcaacggc 1680
agcctgcagt gccggatctg catccggcgg aagcggggaa gcggagctac taacttcagc 1740
ctgctgaagc aggctggaga cgtggaggag aaccctggac ctatgaaaac catcatcgcc 1800
ctgagctaca tcttctgcct cgccctcggc caggacctgc ccggcaacga caacagcacc 1860
gccaccctgt gcctgggcca ccacgccgtg cccaacggca ccctggtgaa aacaattacc 1920
gacgaccaga tcgaggtgac caacgccacc gagctggtgc agagcagcag caccggcaag 1980
atctgcaaca acccccaccg catcctggac ggcatcgact gcaccctgat cgacgccctg 2040
ctgggcgacc ctcactgcga cgtgttccag aacgagacct gggacctgtt cgtggagcgc 2100

```
agcaaggcct tcagcaactg ctaccoctac gacgtgcccg actacgcttc cctgcgcagc    2160
ctggtcgcca gctccgggac cctggagttc atcaccgagg gcttcacctg gaccggggtc    2220
acacagaatg gggggtccaa cgcctgcaag cgcggacccg gcagcggctt cttcagccgc    2280
ctgaactggc tgaccaagag cggcagcacc taccccgtgc tgaacgtgac catgcccaac    2340
aacgacaact tcgacaagct gtacatctgg ggcgtgcacc accccagcac caaccaggaa    2400
cagaccagcc tgtacgtgca ggccagcggc agggtgaccg tgagcacccg ccgcagccag    2460
cagaccatca tccccaacat cgagtcccgg ccctgggtcc gcgggctgtc cagccgcatc    2520
agcatctact ggaccatcgt gaagcccggc gacgtgctgg tgatcaacag caacggcaac    2580
ctgatcgccc caggggcta cttcaagatg cggaccggca agagcagcat catgcgcagc    2640
gacgccccca tcgacacctg catcagcgag tgcatcaccc ccaacggcag catccccaac    2700
gacaagccct tccagaacgt gaacaagatc acctacgggg cctgtcctaa gtacgtgaag    2760
cagaacaccc tgaagctcgc taccggcatg cggaacgtgc ccgagaagca gaccagggc    2820
ctgttcgggg ccatcgccgg cttcatcgag aacggctggg agggcatgat cgacgggtgg    2880
tatggcttcc gccaccagaa cagcgagggc accggccagg ccgccgacct gaagagcacc    2940
caggccgcca tcgaccagat caacggcaag ctgaaccgcg tgatcgagaa aaccaacgag    3000
aagttccacc agatcgagaa agagttcagc gaggtcgagg gccgcatcca ggacctggag    3060
aagtacgtgg aggacaccaa gatcgacctg tggagctaca acgccgagct gctggtcgcc    3120
ctggagaacc agcacaccat cgacctgacc gacagcgaga tgaacaagct gttcgagaaa    3180
acccgcaggc agctgcgcga aacgccgag gacatgggca acggctgctt caagatctac    3240
cacaagtgcg acaacgcctg catcgagagc atccgcaacg gcacctacga ccacgacgtg    3300
taccgcgacg aggccctgaa caaccgcttc cagatcaagg gcgtggagct gaagagcggc    3360
tacaaggact ggatcctgtg gatcagcttc gctatcagct gcttcctgct gtgcgtggtg    3420
ctgctgggct tcatcatgtg ggcctgccag cggggcaaca tccgctgcaa catctgcatc    3480
cggcggaagc ggggaagcgg agctactaac ttcagcctgc tgaagcaggc tggagacgtg    3540
gaggagaacc ctggacctat gaaccccaac cagaagatca tcaccatcgg cagcgtgtgc    3600
atgaccatcg gcatggccaa cctgatcctg cagatcggca acatcatcag catctggatc    3660
agccacagca tccagctggg caaccagaac cagatcgaga catgcaacca gagcgtgatc    3720
acctacgaga caacacctg ggtgaaccag acctacgtga acatcagcaa caccaacttc    3780
gccgctggcc agagcgtggt gtctgtgaag ctggccggca acagcagcct gtgccctgtg    3840
tccggctggg ccatctacag caaggacaac agcgtgcgga tcggcagcaa gggcgacgtg    3900
ttcgtgatcc gggagccctt catcagctgc agccccctgg aatgccggac cttcttcctg    3960
acccaggggg ccctgctgaa cgacaagcac agcaacggca ccatcaagga cagaagcccc    4020
taccggaccc tgatgagctg ccccatcggc gaggtgccca gccctacaa cagcagattc    4080
gagtccgtgg cttggagcgc ctctgcctgc cacgacggca tcaactggct gacaatcggc    4140
atcagcggcc ctgataacgg cgctgtggcc gtgctgaagt acaacggcat catcaccgac    4200
acaatcaaga gctggcggaa caacatcctg cggacccagg aatccgagtg cgcctgcgtg    4260
aacggcagct gcttcaccgt gatgaccgac ggccctagca atggccaggc cagctacaag    4320
atcttccgga tcgagaaggg caagatcgtg aagtccgtgg agatgaacgc ccccaactac    4380
cactacgagg aatgcagctg ctaccccgac agcagcgaga tcacctgtgt gtgccgggac    4440
```

```
aactggcacg gcagcaacag accctggctg tccttcaacc agaatctgga ataccagatc    4500
ggctacattt gcagcggcat cttcggcgac aaccccagac ccaacgacaa gaccggaagc    4560
tgcggccctg tgtctagcaa cggggccaac ggcgtgaagg gcttcagctt caagtacggc    4620
aatggcgtgt ggatcggccg gaccaagagc atcagcagcc ggaacggctt cgagatgatc    4680
tgggacccca acggctggac cggcaccgac aacaacttca gcatcaagca ggacatcgtg    4740
ggcatcaacg agtggagcgg ctacagcggc agcttcgtgc agcaccctga gctgaccggc    4800
ctggactgca tccggccctg cttttgggtg gagctgatca gaggcagacc caaagagaac    4860
accatctgga ccagcggcag cagcatcagc ttttgcggcg tgaacagcga caccgtgggc    4920
tggtcttggc ccgatggggc cgagctgccc ttcaccatcg acaagcggcg aagcgggga    4980 agcggagcta ctaacttcag cctgctgaag caggctggag acgtggagga gaaccctgga    5040
cctatgaacc ccaaccagaa gatcatcacc atcggcagcg tgagcctgac aatcgctacc    5100
gtgtgcttcc tgatgcagat cgccatcctg tgaccaccg tgaccctgca cttcaagcag    5160
tacgagtgcg acagccccgc cagcaaccag gtcatgccct gcgagcccat catcatcgag    5220
cgcaacatca ccgagatcgt gtacctgaac aacaccacca tcgagaagga aatctgcccc    5280
aaggtcgtgg agtaccgcaa ctggtccaag ccccagtgcc agatcaccgg cttcgccccc    5340
ttcagcaagg acaacagcat ccgcctgagc gccggagggg acatctgggt cacccgcgag    5400
ccctacgtga gctgcgacca cggcaagtgc taccagttcg ctctggggca ggggacaaca    5460
ctcgataaca agcacagcaa cgacaccatc cacgaccgca tccccaccg caccctgctg    5520 atgaacgagc tgggcgtgcc cttccacctg ggcacccgcc aggtctgcat cgcctggtcc    5580
agcagcagct gccacgacgg caaggcctgg ctgcacgtgt gcatcaccgg cgacgacaag    5640
aacgccaccg ccagcttcat ctacgacggc cgcctggtgg acagcatcgg cagctggtcc    5700
cagaacatcc tgcgcaccca agaaagcgag tgcgtctgca tcaacgggac ctgcaccgtg    5760
gtgatgaccg atggaagcgc cagcggcagg gccgataccc ggatcctgtt catcgaggaa    5820
ggcaagatcg tgcacatcag ccctctcagc ggctccgccc agcacgtgga agagtgcagc    5880
tgctaccccc gctaccccgg cgtgcgctgc atctgccgcg acaactggaa gggcagcaac    5940
cgccccgtgg tggacatcaa catggaggac tacagcatcg acagcagcta cgtgtgcagc    6000
ggcctggtcg cgacacacc ccgcaacgac gaccgcagca gcacagcaa ctgccgcaac    6060 cccaacaacg agcgcggcaa ccagggcgtg aagggctggg ccttcgacaa cggcgacgac    6120
gtgtggatgg gccgcaccat ctccaaggac ctgcgcagcg gctacgagac cttcaaggtg    6180
atcggcgggt ggagcacccc caacagcaag agccagatca accgccaggt gatcgtggac    6240
agcgacaacc gctccggcta cagcggcatc ttcagcgtgg agggcaagtc ctgcatcaac    6300
cgctgcttct acgtggagct gatccgcggc aggaagcaag aaacccgcgt ctggtggacc    6360
agcaactcca tcgtggtgtt ctgcggcacc agcggcacct acggcaccgg cagctggccc    6420
gacggggcca acatcaactt catgcccatc cggcggaagc ggggaagcgg cgccactaac    6480
ttcagcctgc tgaagcaggc tggagacgtg aggagaacc ctggacctat ggccagccag    6540
ggcaccaaga gaagctacga gcagatggaa accgacggcg agaggcagaa cgccaccgag    6600
atcagggcca gcgtgggcag gatgatcggc ggcatcggca ggttctacat ccagatgtgc    6660
accgagctga agctgtccga ctacgagggc aggctgatcc agaacagcat caccatcgag    6720
aggatggtgc tgtccgcctt cgacgagaga agaaacaagt acctggaaga gcaccccagc    6780
gccggcaagg accccaagaa aaccggcgga cccatctaca agaggatcga cggcaagtgg    6840
```

```
atgagagagc tgatcctgtg ggagaaggac gacatcaagc ggatctacaa gcaggccaac      6900
aacggcgagg acgccacagc cggcctgacc cacatgatga tctggcacag caacctgaac      6960
gacgccacct accagaggac cagggccctc gtcagaaccg gcatggaccc ccggatgtgc      7020
agcctgatgc agggcagcac actgcccaga agaagcggag ctgctggagc cgccgtgaag      7080
ggcgtgggca ccatggtgat ggaactgatc aggatgatca agaggggcat caacgacagg      7140
aacttttgga ggggcgagaa cggcagaagg accaggatcg cctacgagag gatgtgcaac      7200
atcctgaagg gcaagttcca gacagccgcc cagagggcca tgatggacca ggtccgggag      7260
agcaggaacc ccggcaacgc cgagatcgag gacctgatct tcctggccag aagcgccctg      7320
atcctgaggg gcagcgtggc ccacaagagc tgcctgcccg cctgcgtgta cggacccgcc      7380
gtggccagcg gctacgactt cgagagagag ggctacagcc tggtcggcat cgaccccttc      7440
aggctgctgc agaactccca ggtgtactct ctgatcaggc ccaacgagaa ccccgcccac      7500
aagtcccagc tggtctggat ggcctgccac agcgccgcct tcgaggatct gagagtgagc      7560
agcttcatca ggggcaccag agtggtgccc aggggcaagc tgtccaccag gggcgtgcag      7620
atcgccagca acgagaacat ggaaaccatg gacagcagca ccctggaact gagaagcagg      7680
tactgggcca tcaggaccag aagcggcggc aacaccaacc agcagagggc cagcgccgga      7740
cagatcagcg tgcagcccac cttctccgtg cagaggaacc tgcccttcga ggggccacc      7800
atcatggccg ccttcaccgg caacaccgag ggcaggacca gagacatgag gaccgagatc      7860
atcagaatga tggaaagcgc caggcccgag gacgtgagct tccagggcag gggcgtgttc      7920
gagctgtccg atgagaaggc cacctccccc atcgtgccca gcttcgacat gagcaacgag      7980
ggcagctact tcttcggcga caacgccgag gaatacgaca accggcggaa gcggggaagc      8040
ggcgccacta acttcagcct gctgaagcag gctggagacg tggaggagaa ccctggacct      8100
atgagcctgc tgaccgaggt ggagacctac gtgctgagca tcgtgcccag cggcccctg      8160
aaggccgaga tcgcccagcg gctggaggac gtgttcgccg gcaagaacac cgacctggag      8220
gccctgatgg agtggctgaa gacccggccc atcctgagcc ccctgaccaa gggcatcctg      8280
ggcttcgtgt tcacccctgac cgtgcccagc gagcggggcc tgcagcggcg gcggttcgtg      8340
cagaacgccc tgaacggcaa cggcgacccc aacaacatgg accgggccgt gaagctgtac      8400
cggaagctga agcgggagat cacccttccac ggagccaagg aggtggccct gagctacagc      8460
gccggagccc tggccagctg catgggcctg atctacaacc ggatgggcac cgtgaccacc      8520
gaggtggcct tcgcctggt gtgcgccacc tgcgagcaga tcgccgacag ccagcaccgg      8580
agccaccggc agatggtgac caccaccaac cccctgatcc ggcacgagaa ccggatggtg      8640
ctggccagca ccaccgccaa ggccatggag cagatggccg gcagcagcga gcaggccgcc      8700
gaggccatgg aggtggccag ccaggcccgg cagatggtgc aggccatgcg gaccatcggc      8760
acccaccccca gcagcagcgc cggcctgaag gacgacctga tcgagaacct gcaggcctac      8820
cagaagcgga tgggcgtgca gatgcagcgg ttcaagcggc ggaagcgggg aagcggagct      8880
actaacttca gcctgctgaa gcaggctgga gacgtggagg agaaccctgg acctatgagc      8940
ctgctgacca ggtggagac ccccacccgg aacgagtggg gctgccggtg caacgacagc      9000
agcgaccccc tggtgatcgc cgccagcatc atcggcatcc tgcacctgat cctgtggatc      9060
ctggaccggc tgttcttcaa gtgcatctac cggcggctga gtacggcct gaagcggggc      9120
cccagcaccg agggcgtgcc cgagagcatg cgggaggagt accggaagga gcagcagagc      9180
```

```
gccgtggacg tggacgacgg ccacttcgtg aacatcgagc tggagtga                    9228
```

<210> SEQ ID NO 2
<211> LENGTH: 3073
<212> TYPE: PRT
<213> ORGANISM: Influenza A virus

<400> SEQUENCE: 2

| Met | Lys | Ala | Ile | Leu | Val | Val | Leu | Leu | Tyr | Thr | Phe | Ala | Thr | Ala | Asn |
|---|---|---|---|---|---|---|---|---|---|---|---|---|---|---|---|
| 1 | | | | 5 | | | | | 10 | | | | | 15 | |

| Ala | Asp | Thr | Leu | Cys | Ile | Gly | Tyr | His | Ala | Asn | Asn | Ser | Thr | Asp | Thr |
|---|---|---|---|---|---|---|---|---|---|---|---|---|---|---|---|
| | | | 20 | | | | | 25 | | | | | 30 | | |

| Val | Asp | Thr | Val | Leu | Glu | Lys | Asn | Val | Thr | Val | Thr | His | Ser | Val | Asn |
|---|---|---|---|---|---|---|---|---|---|---|---|---|---|---|---|
| | | 35 | | | | | 40 | | | | | 45 | | | |

| Leu | Leu | Glu | Asp | Lys | His | Asn | Gly | Lys | Leu | Cys | Lys | Leu | Arg | Gly | Val |
|---|---|---|---|---|---|---|---|---|---|---|---|---|---|---|---|
| | 50 | | | | | 55 | | | | | 60 | | | | |

| Ala | Pro | Leu | His | Leu | Gly | Lys | Cys | Asn | Ile | Ala | Gly | Trp | Ile | Leu | Gly |
|---|---|---|---|---|---|---|---|---|---|---|---|---|---|---|---|
| 65 | | | | | 70 | | | | | 75 | | | | | 80 |

| Asn | Pro | Glu | Cys | Glu | Ser | Leu | Ser | Thr | Ala | Ser | Ser | Trp | Ser | Tyr | Ile |
|---|---|---|---|---|---|---|---|---|---|---|---|---|---|---|---|
| | | | | 85 | | | | | 90 | | | | | 95 | |

| Val | Glu | Thr | Pro | Ser | Ser | Asp | Asn | Gly | Thr | Cys | Tyr | Pro | Gly | Asp | Phe |
|---|---|---|---|---|---|---|---|---|---|---|---|---|---|---|---|
| | | | 100 | | | | | 105 | | | | | 110 | | |

| Ile | Asp | Tyr | Glu | Glu | Leu | Arg | Glu | Gln | Leu | Ser | Ser | Val | Ser | Ser | Phe |
|---|---|---|---|---|---|---|---|---|---|---|---|---|---|---|---|
| | | | 115 | | | | | 120 | | | | | 125 | | |

| Glu | Arg | Phe | Glu | Ile | Phe | Pro | Lys | Thr | Ser | Ser | Trp | Pro | Asn | His | Asp |
|---|---|---|---|---|---|---|---|---|---|---|---|---|---|---|---|
| | 130 | | | | | 135 | | | | | 140 | | | | |

| Ser | Asp | Lys | Gly | Val | Thr | Ala | Ala | Cys | Pro | His | Ala | Gly | Ala | Lys | Ser |
|---|---|---|---|---|---|---|---|---|---|---|---|---|---|---|---|
| 145 | | | | | 150 | | | | | 155 | | | | | 160 |

| Phe | Tyr | Lys | Asn | Leu | Ile | Trp | Leu | Val | Lys | Lys | Gly | Asn | Ser | Tyr | Pro |
|---|---|---|---|---|---|---|---|---|---|---|---|---|---|---|---|
| | | | | 165 | | | | | 170 | | | | | 175 | |

| Lys | Leu | Ser | Lys | Ser | Tyr | Ile | Asn | Asp | Lys | Gly | Lys | Glu | Val | Leu | Val |
|---|---|---|---|---|---|---|---|---|---|---|---|---|---|---|---|
| | | | 180 | | | | | 185 | | | | | 190 | | |

| Leu | Trp | Gly | Ile | His | His | Pro | Ser | Thr | Ser | Ala | Asp | Gln | Gln | Ser | Leu |
|---|---|---|---|---|---|---|---|---|---|---|---|---|---|---|---|
| | | 195 | | | | | 200 | | | | | 205 | | | |

| Tyr | Gln | Asn | Ala | Asp | Thr | Tyr | Val | Phe | Val | Gly | Ser | Ser | Arg | Tyr | Ser |
|---|---|---|---|---|---|---|---|---|---|---|---|---|---|---|---|
| | 210 | | | | | 215 | | | | | 220 | | | | |

| Lys | Lys | Phe | Lys | Pro | Glu | Ile | Ala | Ile | Arg | Pro | Lys | Val | Arg | Asp | Gln |
|---|---|---|---|---|---|---|---|---|---|---|---|---|---|---|---|
| 225 | | | | | 230 | | | | | 235 | | | | | 240 |

| Glu | Gly | Arg | Met | Asn | Tyr | Tyr | Trp | Thr | Leu | Val | Glu | Pro | Gly | Asp | Lys |
|---|---|---|---|---|---|---|---|---|---|---|---|---|---|---|---|
| | | | | 245 | | | | | 250 | | | | | 255 | |

| Ile | Thr | Phe | Glu | Ala | Thr | Gly | Asn | Leu | Val | Val | Pro | Arg | Tyr | Ala | Phe |
|---|---|---|---|---|---|---|---|---|---|---|---|---|---|---|---|
| | | | 260 | | | | | 265 | | | | | 270 | | |

| Ala | Met | Glu | Arg | Asn | Ala | Gly | Ser | Gly | Ile | Ile | Ile | Ser | Asp | Thr | Pro |
|---|---|---|---|---|---|---|---|---|---|---|---|---|---|---|---|
| | | 275 | | | | | 280 | | | | | 285 | | | |

| Val | His | Asp | Cys | Asn | Thr | Thr | Cys | Gln | Thr | Pro | Lys | Gly | Ala | Ile | Asn |
|---|---|---|---|---|---|---|---|---|---|---|---|---|---|---|---|
| | 290 | | | | | 295 | | | | | 300 | | | | |

| Thr | Ser | Leu | Pro | Phe | Gln | Asn | Ile | His | Pro | Ile | Thr | Ile | Gly | Lys | Cys |
|---|---|---|---|---|---|---|---|---|---|---|---|---|---|---|---|
| 305 | | | | | 310 | | | | | 315 | | | | | 320 |

| Pro | Lys | Tyr | Val | Lys | Ser | Thr | Lys | Leu | Arg | Leu | Ala | Thr | Gly | Leu | Arg |
|---|---|---|---|---|---|---|---|---|---|---|---|---|---|---|---|
| | | | | 325 | | | | | 330 | | | | | 335 | |

| Asn | Ile | Pro | Ser | Ile | Gln | Ser | Arg | Gly | Leu | Phe | Gly | Ala | Ile | Ala | Gly |
|---|---|---|---|---|---|---|---|---|---|---|---|---|---|---|---|
| | | | 340 | | | | | 345 | | | | | 350 | | |

| Phe | Ile | Glu | Gly | Gly | Trp | Thr | Gly | Met | Val | Asp | Gly | Trp | Tyr | Gly | Tyr |
|---|---|---|---|---|---|---|---|---|---|---|---|---|---|---|---|
| | | 355 | | | | | 360 | | | | | 365 | | | |

```
His His Gln Asn Glu Gln Gly Ser Gly Tyr Ala Ala Asp Leu Lys Ser
    370                 375                 380
Thr Gln Asn Ala Ile Asp Glu Ile Thr Asn Lys Val Asn Ser Val Ile
385                 390                 395                 400
Glu Lys Met Asn Thr Gln Phe Thr Ala Val Gly Lys Glu Phe Asn His
                405                 410                 415
Leu Glu Lys Arg Ile Glu Asn Leu Asn Lys Lys Val Asp Asp Gly Phe
                420                 425                 430
Leu Asp Ile Trp Thr Tyr Asn Ala Glu Leu Leu Val Leu Leu Glu Asn
                435                 440                 445
Glu Arg Thr Leu Asp Tyr His Asp Ser Asn Val Lys Asn Leu Tyr Glu
            450                 455                 460
Lys Val Arg Ser Gln Leu Lys Asn Asn Ala Lys Glu Ile Gly Asn Gly
465                 470                 475                 480
Cys Phe Glu Phe Tyr His Lys Cys Asp Asn Thr Cys Met Glu Ser Val
                485                 490                 495
Lys Asn Gly Thr Tyr Asp Tyr Pro Lys Tyr Ser Glu Glu Ala Lys Leu
                500                 505                 510
Asn Arg Glu Glu Ile Asp Gly Val Lys Leu Glu Ser Thr Arg Ile Tyr
                515                 520                 525
Gln Ile Leu Ala Ile Tyr Ser Thr Val Ala Ser Ser Leu Val Leu Val
            530                 535                 540
Val Ser Leu Gly Ala Ile Ser Phe Trp Met Cys Ser Asn Gly Ser Leu
545                 550                 555                 560
Gln Cys Arg Ile Cys Ile Arg Arg Lys Arg Gly Ser Gly Ala Thr Asn
                565                 570                 575
Phe Ser Leu Leu Lys Gln Ala Gly Asp Val Glu Glu Asn Pro Gly Pro
                580                 585                 590
Met Lys Thr Ile Ile Ala Leu Ser Tyr Ile Phe Cys Leu Ala Leu Gly
                595                 600                 605
Gln Asp Leu Pro Gly Asn Asp Asn Ser Thr Ala Thr Leu Cys Leu Gly
            610                 615                 620
His His Ala Val Pro Asn Gly Thr Leu Val Lys Thr Ile Thr Asp Asp
625                 630                 635                 640
Gln Ile Glu Val Thr Asn Ala Thr Glu Leu Val Gln Ser Ser Ser Thr
                645                 650                 655
Gly Lys Ile Cys Asn Asn Pro His Arg Ile Leu Asp Gly Ile Asp Cys
                660                 665                 670
Thr Leu Ile Asp Ala Leu Leu Gly Asp Pro His Cys Asp Val Phe Gln
            675                 680                 685
Asn Glu Thr Trp Asp Leu Phe Val Glu Arg Ser Lys Ala Phe Ser Asn
            690                 695                 700
Cys Tyr Pro Tyr Asp Val Pro Asp Tyr Ala Ser Leu Arg Ser Leu Val
705                 710                 715                 720
Ala Ser Ser Gly Thr Leu Glu Phe Ile Thr Glu Gly Phe Thr Trp Thr
                725                 730                 735
Gly Val Thr Gln Asn Gly Gly Ser Asn Ala Cys Lys Arg Gly Pro Gly
                740                 745                 750
Ser Gly Phe Phe Ser Arg Leu Asn Trp Leu Thr Lys Ser Gly Ser Thr
                755                 760                 765
Tyr Pro Val Leu Asn Val Thr Met Pro Asn Asn Asp Asn Phe Asp Lys
770                 775                 780
```

-continued

```
Leu Tyr Ile Trp Gly Val His His Pro Ser Thr Asn Gln Glu Gln Thr
785                 790                 795                 800

Ser Leu Tyr Val Gln Ala Ser Gly Arg Val Thr Val Ser Thr Arg Arg
        805                 810                 815

Ser Gln Gln Thr Ile Ile Pro Asn Ile Glu Ser Arg Pro Trp Val Arg
            820                 825                 830

Gly Leu Ser Ser Arg Ile Ser Ile Tyr Trp Thr Ile Val Lys Pro Gly
                835                 840                 845

Asp Val Leu Val Ile Asn Ser Asn Gly Asn Leu Ile Ala Pro Arg Gly
850                 855                 860

Tyr Phe Lys Met Arg Thr Gly Lys Ser Ser Ile Met Arg Ser Asp Ala
865                 870                 875                 880

Pro Ile Asp Thr Cys Ile Ser Glu Cys Ile Thr Pro Asn Gly Ser Ile
                885                 890                 895

Pro Asn Asp Lys Pro Phe Gln Asn Val Asn Lys Ile Thr Tyr Gly Ala
            900                 905                 910

Cys Pro Lys Tyr Val Lys Gln Asn Thr Leu Lys Leu Ala Thr Gly Met
        915                 920                 925

Arg Asn Val Pro Glu Lys Gln Thr Arg Gly Leu Phe Gly Ala Ile Ala
930                 935                 940

Gly Phe Ile Glu Asn Gly Trp Glu Gly Met Ile Asp Gly Trp Tyr Gly
945                 950                 955                 960

Phe Arg His Gln Asn Ser Glu Gly Thr Gly Gln Ala Ala Asp Leu Lys
                965                 970                 975

Ser Thr Gln Ala Ala Ile Asp Gln Ile Asn Gly Lys Leu Asn Arg Val
            980                 985                 990

Ile Glu Lys Thr Asn Glu Lys Phe His Gln Ile Glu Lys  Glu Phe Ser
        995                 1000                1005

Glu Val  Glu Gly Arg Ile Gln  Asp Leu Glu Lys Tyr  Val Glu Asp
     1010                1015                1020

Thr Lys  Ile Asp Leu Trp Ser  Tyr Asn Ala Glu Leu  Leu Val Ala
     1025                1030                1035

Leu Glu  Asn Gln His Thr Ile  Asp Leu Thr Asp Ser  Glu Met Asn
     1040                1045                1050

Lys Leu  Phe Glu Lys Thr Arg  Arg Gln Leu Arg Glu  Asn Ala Glu
     1055                1060                1065

Asp Met  Gly Asn Gly Cys Phe  Lys Ile Tyr His Lys  Cys Asp Asn
     1070                1075                1080

Ala Cys  Ile Glu Ser Ile Arg  Asn Gly Thr Tyr Asp  His Asp Val
     1085                1090                1095

Tyr Arg  Asp Glu Ala Leu Asn  Asn Arg Phe Gln Ile  Lys Gly Val
     1100                1105                1110

Glu Leu  Lys Ser Gly Tyr Lys  Asp Trp Ile Leu Trp  Ile Ser Phe
     1115                1120                1125

Ala Ile  Ser Cys Phe Leu Leu  Cys Val Val Leu Leu  Gly Phe Ile
     1130                1135                1140

Met Trp  Ala Cys Gln Arg Gly  Asn Ile Arg Cys Asn  Ile Cys Ile
     1145                1150                1155

Arg Arg  Lys Arg Gly Ser Gly  Ala Thr Asn Phe Ser  Leu Leu Lys
     1160                1165                1170

Gln Ala  Gly Asp Val Glu Glu  Asn Pro Gly Pro Met  Asn Pro Asn
     1175                1180                1185
```

-continued

Gln Lys Ile Ile Thr Ile Gly Ser Val Cys Met Thr Ile Gly Met
1190                1195                1200

Ala Asn Leu Ile Leu Gln Ile Gly Asn Ile Ile Ser Ile Trp Ile
1205                1210                1215

Ser His Ser Ile Gln Leu Gly Asn Gln Asn Gln Ile Glu Thr Cys
1220                1225                1230

Asn Gln Ser Val Ile Thr Tyr Glu Asn Asn Thr Trp Val Asn Gln
1235                1240                1245

Thr Tyr Val Asn Ile Ser Asn Thr Asn Phe Ala Ala Gly Gln Ser
1250                1255                1260

Val Val Ser Val Lys Leu Ala Gly Asn Ser Ser Leu Cys Pro Val
1265                1270                1275

Ser Gly Trp Ala Ile Tyr Ser Lys Asp Asn Ser Val Arg Ile Gly
1280                1285                1290

Ser Lys Gly Asp Val Phe Val Ile Arg Glu Pro Phe Ile Ser Cys
1295                1300                1305

Ser Pro Leu Glu Cys Arg Thr Phe Phe Leu Thr Gln Gly Ala Leu
1310                1315                1320

Leu Asn Asp Lys His Ser Asn Gly Thr Ile Lys Asp Arg Ser Pro
1325                1330                1335

Tyr Arg Thr Leu Met Ser Cys Pro Ile Gly Glu Val Pro Ser Pro
1340                1345                1350

Tyr Asn Ser Arg Phe Glu Ser Val Ala Trp Ser Ala Ser Ala Cys
1355                1360                1365

His Asp Gly Ile Asn Trp Leu Thr Ile Gly Ile Ser Gly Pro Asp
1370                1375                1380

Asn Gly Ala Val Ala Val Leu Lys Tyr Asn Gly Ile Ile Thr Asp
1385                1390                1395

Thr Ile Lys Ser Trp Arg Asn Asn Ile Leu Arg Thr Gln Glu Ser
1400                1405                1410

Glu Cys Ala Cys Val Asn Gly Ser Cys Phe Thr Val Met Thr Asp
1415                1420                1425

Gly Pro Ser Asn Gly Gln Ala Ser Tyr Lys Ile Phe Arg Ile Glu
1430                1435                1440

Lys Gly Lys Ile Val Lys Ser Val Glu Met Asn Ala Pro Asn Tyr
1445                1450                1455

His Tyr Glu Glu Cys Ser Cys Tyr Pro Asp Ser Ser Glu Ile Thr
1460                1465                1470

Cys Val Cys Arg Asp Asn Trp His Gly Ser Asn Arg Pro Trp Val
1475                1480                1485

Ser Phe Asn Gln Asn Leu Glu Tyr Gln Ile Gly Tyr Ile Cys Ser
1490                1495                1500

Gly Ile Phe Gly Asp Asn Pro Arg Pro Asn Asp Lys Thr Gly Ser
1505                1510                1515

Cys Gly Pro Val Ser Ser Asn Gly Ala Asn Gly Val Lys Gly Phe
1520                1525                1530

Ser Phe Lys Tyr Gly Asn Gly Val Trp Ile Gly Arg Thr Lys Ser
1535                1540                1545

Ile Ser Ser Arg Asn Gly Phe Glu Met Ile Trp Asp Pro Asn Gly
1550                1555                1560

Trp Thr Gly Thr Asp Asn Asn Phe Ser Ile Lys Gln Asp Ile Val
1565                1570                1575

-continued

```
Gly Ile Asn Glu Trp Ser Gly Tyr Ser Gly Ser Phe Val Gln His
1580            1585            1590

Pro Glu Leu Thr Gly Leu Asp Cys Ile Arg Pro Cys Phe Trp Val
1595            1600            1605

Glu Leu Ile Arg Gly Arg Pro Lys Glu Asn Thr Ile Trp Thr Ser
1610            1615            1620

Gly Ser Ser Ile Ser Phe Cys Gly Val Asn Ser Asp Thr Val Gly
1625            1630            1635

Trp Ser Trp Pro Asp Gly Ala Glu Leu Pro Phe Thr Ile Asp Lys
1640            1645            1650

Arg Arg Lys Arg Gly Ser Gly Ala Thr Asn Phe Ser Leu Leu Lys
1655            1660            1665

Gln Ala Gly Asp Val Glu Glu Asn Pro Gly Pro Met Asn Pro Asn
1670            1675            1680

Gln Lys Ile Ile Thr Ile Gly Ser Val Ser Leu Thr Ile Ala Thr
1685            1690            1695

Val Cys Phe Leu Met Gln Ile Ala Ile Leu Val Thr Thr Val Thr
1700            1705            1710

Leu His Phe Lys Gln Tyr Glu Cys Asp Ser Pro Ala Ser Asn Gln
1715            1720            1725

Val Met Pro Cys Glu Pro Ile Ile Ile Glu Arg Asn Ile Thr Glu
1730            1735            1740

Ile Val Tyr Leu Asn Asn Thr Thr Ile Glu Lys Glu Ile Cys Pro
1745            1750            1755

Lys Val Val Glu Tyr Arg Asn Trp Ser Lys Pro Gln Cys Gln Ile
1760            1765            1770

Thr Gly Phe Ala Pro Phe Ser Lys Asp Asn Ser Ile Arg Leu Ser
1775            1780            1785

Ala Gly Gly Asp Ile Trp Val Thr Arg Glu Pro Tyr Val Ser Cys
1790            1795            1800

Asp His Gly Lys Cys Tyr Gln Phe Ala Leu Gly Gln Gly Thr Thr
1805            1810            1815

Leu Asp Asn Lys His Ser Asn Asp Thr Ile His Asp Arg Ile Pro
1820            1825            1830

His Arg Thr Leu Leu Met Asn Glu Leu Gly Val Pro Phe His Leu
1835            1840            1845

Gly Thr Arg Gln Val Cys Ile Ala Trp Ser Ser Ser Cys His
1850            1855            1860

Asp Gly Lys Ala Trp Leu His Val Cys Ile Thr Gly Asp Asp Lys
1865            1870            1875

Asn Ala Thr Ala Ser Phe Ile Tyr Asp Gly Arg Leu Val Asp Ser
1880            1885            1890

Ile Gly Ser Trp Ser Gln Asn Ile Leu Arg Thr Gln Glu Ser Glu
1895            1900            1905

Cys Val Cys Ile Asn Gly Thr Cys Thr Val Val Met Thr Asp Gly
1910            1915            1920

Ser Ala Ser Gly Arg Ala Asp Thr Arg Ile Leu Phe Ile Glu Glu
1925            1930            1935

Gly Lys Ile Val His Ile Ser Pro Leu Ser Gly Ser Ala Gln His
1940            1945            1950

Val Glu Glu Cys Ser Cys Tyr Pro Arg Tyr Pro Gly Val Arg Cys
1955            1960            1965
```

-continued

```
Ile Cys Arg Asp Asn Trp Lys Gly Ser Asn Arg Pro Val Val Asp
1970                1975                1980
Ile Asn Met Glu Asp Tyr Ser Ile Asp Ser Ser Tyr Val Cys Ser
1985                1990                1995
Gly Leu Val Gly Asp Thr Pro Arg Asn Asp Asp Arg Ser Ser Asn
2000                2005                2010
Ser Asn Cys Arg Asn Pro Asn Asn Glu Arg Gly Asn Gln Gly Val
2015                2020                2025
Lys Gly Trp Ala Phe Asp Asn Gly Asp Asp Val Trp Met Gly Arg
2030                2035                2040
Thr Ile Ser Lys Asp Leu Arg Ser Gly Tyr Glu Thr Phe Lys Val
2045                2050                2055
Ile Gly Gly Trp Ser Thr Pro Asn Ser Lys Ser Gln Ile Asn Arg
2060                2065                2070
Gln Val Ile Val Asp Ser Asp Asn Arg Ser Gly Tyr Ser Gly Ile
2075                2080                2085
Phe Ser Val Glu Gly Lys Ser Cys Ile Asn Arg Cys Phe Tyr Val
2090                2095                2100
Glu Leu Ile Arg Gly Arg Lys Gln Glu Thr Arg Val Trp Trp Thr
2105                2110                2115
Ser Asn Ser Ile Val Val Phe Cys Gly Thr Ser Gly Thr Tyr Gly
2120                2125                2130
Thr Gly Ser Trp Pro Asp Gly Ala Asn Ile Asn Phe Met Pro Ile
2135                2140                2145
Arg Arg Lys Arg Gly Ser Gly Ala Thr Asn Phe Ser Leu Leu Lys
2150                2155                2160
Gln Ala Gly Asp Val Glu Glu Asn Pro Gly Pro Met Ala Ser Gln
2165                2170                2175
Gly Thr Lys Arg Ser Tyr Glu Gln Met Glu Thr Asp Gly Glu Arg
2180                2185                2190
Gln Asn Ala Thr Glu Ile Arg Ala Ser Val Gly Arg Met Ile Gly
2195                2200                2205
Gly Ile Gly Arg Phe Tyr Ile Gln Met Cys Thr Glu Leu Lys Leu
2210                2215                2220
Ser Asp Tyr Glu Gly Arg Leu Ile Gln Asn Ser Ile Thr Ile Glu
2225                2230                2235
Arg Met Val Leu Ser Ala Phe Asp Glu Arg Arg Asn Lys Tyr Leu
2240                2245                2250
Glu Glu His Pro Ser Ala Gly Lys Asp Pro Lys Lys Thr Gly Gly
2255                2260                2265
Pro Ile Tyr Arg Arg Ile Asp Gly Lys Trp Met Arg Glu Leu Ile
2270                2275                2280
Leu Trp Glu Lys Asp Asp Ile Lys Arg Ile Tyr Lys Gln Ala Asn
2285                2290                2295
Asn Gly Glu Asp Ala Thr Ala Gly Leu Thr His Met Met Ile Trp
2300                2305                2310
His Ser Asn Leu Asn Asp Ala Thr Tyr Gln Arg Thr Arg Ala Leu
2315                2320                2325
Val Arg Thr Gly Met Asp Pro Arg Met Cys Ser Leu Met Gln Gly
2330                2335                2340
Ser Thr Leu Pro Arg Arg Ser Gly Ala Ala Gly Ala Ala Val Lys
2345                2350                2355
```

```
Gly Val Gly Thr Met Val Met Glu Leu Ile Arg Met Ile Lys Arg
    2360            2365            2370

Gly Ile Asn Asp Arg Asn Phe Trp Arg Gly Glu Asn Gly Arg Arg
    2375            2380            2385

Thr Arg Ile Ala Tyr Glu Arg Met Cys Asn Ile Leu Lys Gly Lys
    2390            2395            2400

Phe Gln Thr Ala Ala Gln Arg Ala Met Met Asp Gln Val Arg Glu
    2405            2410            2415

Ser Arg Asn Pro Gly Asn Ala Glu Ile Glu Asp Leu Ile Phe Leu
    2420            2425            2430

Ala Arg Ser Ala Leu Ile Leu Arg Gly Ser Val Ala His Lys Ser
    2435            2440            2445

Cys Leu Pro Ala Cys Val Tyr Gly Pro Ala Val Ala Ser Gly Tyr
    2450            2455            2460

Asp Phe Glu Arg Glu Gly Tyr Ser Leu Val Gly Ile Asp Pro Phe
    2465            2470            2475

Arg Leu Leu Gln Asn Ser Gln Val Tyr Ser Leu Ile Arg Pro Asn
    2480            2485            2490

Glu Asn Pro Ala His Lys Ser Gln Leu Val Trp Met Ala Cys His
    2495            2500            2505

Ser Ala Ala Phe Glu Asp Leu Arg Val Ser Ser Phe Ile Arg Gly
    2510            2515            2520

Thr Arg Val Val Pro Arg Gly Lys Leu Ser Thr Arg Gly Val Gln
    2525            2530            2535

Ile Ala Ser Asn Glu Asn Met Glu Thr Met Asp Ser Ser Thr Leu
    2540            2545            2550

Glu Leu Arg Ser Arg Tyr Trp Ala Ile Arg Thr Arg Ser Gly Gly
    2555            2560            2565

Asn Thr Asn Gln Gln Arg Ala Ser Ala Gly Gln Ile Ser Val Gln
    2570            2575            2580

Pro Thr Phe Ser Val Gln Arg Asn Leu Pro Phe Glu Arg Ala Thr
    2585            2590            2595

Ile Met Ala Ala Phe Thr Gly Asn Thr Glu Gly Arg Thr Arg Asp
    2600            2605            2610

Met Arg Thr Glu Ile Ile Arg Met Met Glu Ser Ala Arg Pro Glu
    2615            2620            2625

Asp Val Ser Phe Gln Gly Arg Gly Val Phe Glu Leu Ser Asp Glu
    2630            2635            2640

Lys Ala Thr Ser Pro Ile Val Pro Ser Phe Asp Met Ser Asn Glu
    2645            2650            2655

Gly Ser Tyr Phe Phe Gly Asp Asn Ala Glu Glu Tyr Asp Asn Arg
    2660            2665            2670

Arg Lys Arg Gly Ser Gly Ala Thr Asn Phe Ser Leu Leu Lys Gln
    2675            2680            2685

Ala Gly Asp Val Glu Glu Asn Pro Gly Pro Met Ser Leu Leu Thr
    2690            2695            2700

Glu Val Glu Thr Tyr Val Leu Ser Ile Val Pro Ser Gly Pro Leu
    2705            2710            2715

Lys Ala Glu Ile Ala Gln Arg Leu Glu Asp Val Phe Ala Gly Lys
    2720            2725            2730

Asn Thr Asp Leu Glu Ala Leu Met Glu Trp Leu Lys Thr Arg Pro
    2735            2740            2745
```

```
Ile Leu Ser Pro Leu Thr Lys Gly Ile Leu Gly Phe Val Phe Thr
2750                2755                2760

Leu Thr Val Pro Ser Glu Arg Gly Leu Gln Arg Arg Arg Phe Val
2765                2770                2775

Gln Asn Ala Leu Asn Gly Asn Gly Asp Pro Asn Met Asp Arg
2780                2785                2790

Ala Val Lys Leu Tyr Arg Lys Leu Lys Arg Glu Ile Thr Phe His
2795                2800                2805

Gly Ala Lys Glu Val Ala Leu Ser Tyr Ser Ala Gly Ala Leu Ala
2810                2815                2820

Ser Cys Met Gly Leu Ile Tyr Asn Arg Met Gly Thr Val Thr Thr
2825                2830                2835

Glu Val Ala Phe Gly Leu Val Cys Ala Thr Cys Glu Gln Ile Ala
2840                2845                2850

Asp Ser Gln His Arg Ser His Arg Gln Met Val Thr Thr Thr Asn
2855                2860                2865

Pro Leu Ile Arg His Glu Asn Arg Met Val Leu Ala Ser Thr Thr
2870                2875                2880

Ala Lys Ala Met Glu Gln Met Ala Gly Ser Ser Glu Gln Ala Ala
2885                2890                2895

Glu Ala Met Glu Val Ala Ser Gln Ala Arg Gln Met Val Gln Ala
2900                2905                2910

Met Arg Thr Ile Gly Thr His Pro Ser Ser Ser Ala Gly Leu Lys
2915                2920                2925

Asp Asp Leu Ile Glu Asn Leu Gln Ala Tyr Gln Lys Arg Met Gly
2930                2935                2940

Val Gln Met Gln Arg Phe Lys Arg Arg Lys Arg Gly Ser Gly Ala
2945                2950                2955

Thr Asn Phe Ser Leu Leu Lys Gln Ala Gly Asp Val Glu Glu Asn
2960                2965                2970

Pro Gly Pro Met Ser Leu Leu Thr Glu Val Glu Thr Pro Thr Arg
2975                2980                2985

Asn Glu Trp Gly Cys Arg Cys Asn Asp Ser Ser Asp Pro Leu Val
2990                2995                3000

Ile Ala Ala Ser Ile Ile Gly Ile Leu His Leu Ile Leu Trp Ile
3005                3010                3015

Leu Asp Arg Leu Phe Phe Lys Cys Ile Tyr Arg Arg Leu Lys Tyr
3020                3025                3030

Gly Leu Lys Arg Gly Pro Ser Thr Glu Gly Val Pro Glu Ser Met
3035                3040                3045

Arg Glu Glu Tyr Arg Lys Glu Gln Gln Ser Ala Val Asp Val Asp
3050                3055                3060

Asp Gly His Phe Val Asn Ile Glu Leu Glu
3065                3070

<210> SEQ ID NO 3
<211> LENGTH: 12
<212> TYPE: DNA
<213> ORGANISM: Homo sapiens

<400> SEQUENCE: 3
cggcggaagc gg                                                         12

<210> SEQ ID NO 4
<211> LENGTH: 4
```

```
<212> TYPE: PRT
<213> ORGANISM: Homo sapiens

<400> SEQUENCE: 4

Arg Arg Lys Arg
1

<210> SEQ ID NO 5
<211> LENGTH: 66
<212> TYPE: DNA
<213> ORGANISM: Porcine hemagglutinating encephalomyelitis coronavirus

<400> SEQUENCE: 5
ggaagcggag ctactaactt cagcctgctg aagcaggctg gagacgtgga ggagaaccct    60
ggacct                                                                66

<210> SEQ ID NO 6
<211> LENGTH: 22
<212> TYPE: PRT
<213> ORGANISM: Porcine hemagglutinating encephalomyelitis coronavirus

<400> SEQUENCE: 6

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 7
<211> LENGTH: 66
<212> TYPE: DNA
<213> ORGANISM: Porcine hemagglutinating encephalomyelitis coronavirus

<400> SEQUENCE: 7
ggaagcggcg ccactaactt cagcctgctg aagcaggctg gagacgtgga ggagaaccct    60
ggacct                                                                66

<210> SEQ ID NO 8
<211> LENGTH: 1698
<212> TYPE: DNA
<213> ORGANISM: Influenza A virus

<400> SEQUENCE: 8
atgaaggcta tcctggtggt gctgctgtac accttcgcca ccgccaacgc cgataccctg    60
tgcatcggct accacgccaa caacagcacc gacaccgtgg ataccgtgct ggaaaagaac   120
gtgaccgtga cccacagcgt gaacctgctg gaagataagc acaacggcaa gctgtgcaag   180
ctgagaggcg tggcccctct gcacctgggc aagtgcaata tcgccggctg gatcctgggc   240
aaccccgagt gcgagagcct gagcaccgcc agctcttggt cctacatcgt ggagacaccc   300
agcagcgaca acggcacctg ttaccccggc gacttcatcg actacgagga actgcgggag   360
cagctgtcca gcgtgtccag cttcgagcgg ttcgagatct cccccaagac cagctcctgg   420
cccaaccacg acagcaacaa gggcgtgacc gccgcctgtc ctcacgctgg gccaagagc    480 ttctacaaga acctgatctg gctggtgaag aagggcaaca gctaccccaa gctgtccaag   540
agctacatca acgacaaggg caaagaggtg ctggtgctgt ggggcatcca ccaccctagc   600
accagcgccg accagcagag cctgtaccag aacgccgaca cctacgtgtt cgtgggcagc   660
agccggtaca gcaagaagtt caagcccgag atcgccatca gacccaaagt gcgggaccag   720
gaaggccgga tgaactacta ctggaccctg gtggagcccg gcgacaagat caccttcgag   780
```

```
gccaccggca atctggtggt gcccagatac gccttcgcca tggaaagaaa cgccggcagc    840
ggcatcatca tcagcgacac ccccgtgcac gactgcaaca ccacctgtca gacccccaag    900
ggggccatca acaccagcct gcccttccag aacatccacc ccatcaccat cggcaagtgc    960
cctaagtacg tgaagtccac caagctgaga ctggccaccg gctgcggaaa catcccccag   1020
atccagagca gaggcctgtt cggggccatt gccggcttta tcgagggcgg ctggaccgga   1080
atggtggacg gtggtacgg ctaccaccac cagaatgagc agggcagcgg ctacgccgcc   1140
gacctgaagt ccacacagaa cgccatcgac gagatcacca caaagtgaa cagcgtgatc   1200 gagaagatga cacccagtt caccgccgtg ggcaaagagt tcaaccacct ggaaaagcgg   1260
atcgagaacc tgaacaagaa ggtggacgac ggcttcctgg acatctggac ctacaacgcc   1320
gagctgctgg tgctgctgga aaacgagcgg accctggact accacgactc caacgtgaag   1380
aatctgtacg agaaagtgcg gagccagctg aagaacaacg ccaaagagat cggcaacggc   1440
tgcttcgagt tctaccacaa gtgcgacaac acctgtatgg aaagcgtgaa gaacggcacc   1500
tacgactacc ccaagtacag cgaggaagcc aagctgaacc gggaagagat cgacggcgtg   1560
aagctggaaa gcacccggat ctaccagatc ctggccatct acagcaccgt ggccagctca   1620
ctggtcctgg tcgtgtccct gggcgctatc agcttctgga tgtgcagcaa cggcagcctg   1680
cagtgccgga tctgcatc                                                 1698

<210> SEQ ID NO 9
<211> LENGTH: 566
<212> TYPE: PRT
<213> ORGANISM: Influenza A virus

<400> SEQUENCE: 9

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
        50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
                100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
        130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205
```

```
Tyr Gln Asn Ala Asp Thr Tyr Val Phe Val Gly Ser Ser Arg Tyr Ser
        210                 215                 220
Lys Lys Phe Lys Pro Glu Ile Ala Ile Arg Pro Lys Val Arg Asp Gln
225                 230                 235                 240
Glu Gly Arg Met Asn Tyr Tyr Trp Thr Leu Val Glu Pro Gly Asp Lys
                245                 250                 255
Ile Thr Phe Glu Ala Thr Gly Asn Leu Val Val Pro Arg Tyr Ala Phe
            260                 265                 270
Ala Met Glu Arg Asn Ala Gly Ser Gly Ile Ile Ile Ser Asp Thr Pro
        275                 280                 285
Val His Asp Cys Asn Thr Thr Cys Gln Thr Pro Lys Gly Ala Ile Asn
    290                 295                 300
Thr Ser Leu Pro Phe Gln Asn Ile His Pro Ile Thr Ile Gly Lys Cys
305                 310                 315                 320
Pro Lys Tyr Val Lys Ser Thr Lys Leu Arg Leu Ala Thr Gly Leu Arg
                325                 330                 335
Asn Ile Pro Ser Ile Gln Ser Arg Gly Leu Phe Gly Ala Ile Ala Gly
            340                 345                 350
Phe Ile Glu Gly Gly Trp Thr Gly Met Val Asp Gly Trp Tyr Gly Tyr
        355                 360                 365
His His Gln Asn Glu Gln Gly Ser Gly Tyr Ala Ala Asp Leu Lys Ser
    370                 375                 380
Thr Gln Asn Ala Ile Asp Glu Ile Thr Asn Lys Val Asn Ser Val Ile
385                 390                 395                 400
Glu Lys Met Asn Thr Gln Phe Thr Ala Val Gly Lys Glu Phe Asn His
                405                 410                 415
Leu Glu Lys Arg Ile Glu Asn Leu Asn Lys Lys Val Asp Asp Gly Phe
            420                 425                 430
Leu Asp Ile Trp Thr Tyr Asn Ala Glu Leu Leu Val Leu Leu Glu Asn
        435                 440                 445
Glu Arg Thr Leu Asp Tyr His Asp Ser Asn Val Lys Asn Leu Tyr Glu
    450                 455                 460
Lys Val Arg Ser Gln Leu Lys Asn Asn Ala Lys Glu Ile Gly Asn Gly
465                 470                 475                 480
Cys Phe Glu Phe Tyr His Lys Cys Asp Asn Thr Cys Met Glu Ser Val
                485                 490                 495
Lys Asn Gly Thr Tyr Asp Tyr Pro Lys Tyr Ser Glu Glu Ala Lys Leu
            500                 505                 510
Asn Arg Glu Glu Ile Asp Gly Val Lys Leu Glu Ser Thr Arg Ile Tyr
        515                 520                 525
Gln Ile Leu Ala Ile Tyr Ser Thr Val Ala Ser Ser Leu Val Leu Val
    530                 535                 540
Val Ser Leu Gly Ala Ile Ser Phe Trp Met Cys Ser Asn Gly Ser Leu
545                 550                 555                 560
Gln Cys Arg Ile Cys Ile
                565

<210> SEQ ID NO 10
<211> LENGTH: 1698
<212> TYPE: DNA
<213> ORGANISM: Influ

<400> SEQUENCE: 10

```
atgaaggcta tcctggtggt gctgctgtac accttcgcca ccgccaacgc cgatacctg      60
tgcatcggct accacgccaa caacagcacc gacaccgtgg ataccgtgct ggaaaagaac     120
gtgaccgtga cccacagcgt gaacctgctg aagataagc acaacggcaa gctgtgcaag      180
ctgagaggcg tggcccctct gcacctgggc aagtgcaata cgccggctg datcctgggc      240
aaccccgagt gcgagagcct gagcaccgcc agctcttggt cctacatcgt ggagacaccc     300
agcagcgaca acggcacctg ttaccccggc gacttcatcg actacgagga actgcgggag     360
cagctgtcca gcgtgtccag cttcgagcgg ttcgagatct ccccaagac cagctcctgg      420
cccaaccacg acagcgataa gggcgtgacc gccgcctgtc ctcacgctgg ggccaagagc     480
ttctacaaga acctgatctg gctggtgaag aagggcaaca gctaccccaa gctgtccaag     540
agctacatca cgacaaggg caaagaggtg ctggtgctgt ggggcatcca ccaccctagc      600
accagcgccg accagcagag cctgtaccag aacgccgaca cctacgtgtt cgtgggcagc     660
agccggtaca gcaagaagtt caagcccgag atcgccatca gaccaaagt gcgggaccag      720
gaaggccgga tgaactacta ctggaccctg gtggagcccg cgacaagat caccttcgag      780
gccaccggca atctggtggt gcccagatac gccttcgcca tggaaagaaa cgccggcagc     840
ggcatcatca tcagcgacac ccccgtgcac gactgcaaca ccaccctgtca gaccccaag     900
ggggccatca acaccagcct gccctccag aacatccacc ccatcaccat cggcaagtgc      960
cctaagtacg tgaagtccac caagctgaga ctggccaccg gcctgcggaa catccccagc    1020
atccagagca gaggcctgtt cggggccatt gccggctta tcgagggcgg ctggaccgga     1080
atggtggacg ggtggtacgg ctaccaccac cagaatgagc agggcagcgg ctacgccgcc    1140
gacctgaagt ccacacagaa cgccatcgac gagatcacca caaagtgaa cagcgtgatc     1200
gagaagatga acacccagtt caccgccgtg ggcaaagagt tcaaccacct ggaaaagcgg    1260
atcgagaacc tgaacaagaa ggtggacgac ggcttcctgg acatctggac ctacaacgcc   1320
gagctgctgg tgctgctgga aaacgagcgg accctggact accacgactc caacgtgaag    1380
aatctgtacg agaaagtgcg gagccagctg aagaacaacg ccaaagagat cggcaacggc    1440
tgcttcgagt tctaccacaa gtgcgacaac acctgtatgg aaagcgtgaa gaacggcacc    1500
tacgactacc ccaagtacag cgaggaagcc aagctgaacc gggaagagat cgacggcgtg    1560
aagctggaaa gcaccggat ctaccagatc ctggccatct acagcaccgt ggccagctca    1620
ctggtcctgg tcgtgtccct gggcgctatc agcttctgga tgtgcagcaa cggcagcctg    1680
cagtgccgga tctgcatc                                                  1698
```

<210> SEQ ID NO 11
<211> LENGTH: 566
<212> TYPE: PRT
<213> ORGANISM: Influenza A virus

<400> SEQUENCE: 11

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp

```
Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
 65                  70                  75                  80

Asn Pro Glu Cys Glu Ser Leu Ser Thr Ala Ser Ser Trp Ser Tyr Ile
                 85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
            130                 135                 140

Ser Asp Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
                180                 185                 190

Leu Trp Gly Ile His His Pro Ser Thr Ser Ala Asp Gln Gln Ser Leu
            195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
    450                 455                 460
```

```
Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
            485                 490                 495

Lys Asn Gly Thr Tyr Asp Tyr Pro Lys Tyr Ser Glu Glu Ala Lys Leu
        500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
            530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 12
<211> LENGTH: 1698
<212> TYPE: DNA
<213> ORGANISM: Influenza A virus

<400> SEQUENCE: 12
atgaaaacca tcatcgccct gagctacatc ttctgcctcg ccctcggcca ggacctgccc      60
ggcaacgaca cagcaccgc caccctgtgc ctgggccacc acgccgtgcc aacggcacc      120 ctggtgaaaa caattaccga cgaccagatc gaggtgacca acgccaccga gctggtgcag      180
agcagcagca ccggcaagat ctgcaacaac ccccaccgca tcctggacgg catcgactgc      240
accctgatcg acgccctgct gggcgaccct cactgcgacg tgttccagaa cgagacctgg      300
gacctgttcg tggagcgcag caaggccttc agcaactgct accccta cga cgtgccgac      360 tacgcttccc tgcgcagcct ggtcgccagc tccgggaccc tggagttcat caccgagggc      420
ttcacctgga ccggggtcac acagaatggg gggtccaacg cctgcaagcg cggacccggc      480
agcggcttct tcagccgcct gaactggctg accaagagcg gcagcaccta ccccgtgctg      540
aacgtgacca tgcccaacaa cgacaacttc gacaagctgt acatctgggg cgtgcaccac      600
cccagcacca accaggaaca gaccagcctg tacgtgcagg ccagcggcag ggtgaccgtg      660
agcacccgcc gcagccagca gaccatcatc cccaacatcg agtcccggcc ctgggtccgc      720
gggctgtcca gccgcatcag catctactgg accatcgtga gcccggcga cgtgctggtg      780 atcaacagca cggcaacct gatcgccccc aggggctact caagatgcg gaccggcaag      840 agcagcatca tgcgcagcga cgcccccatc gacacctgca tcagcgagtg catcacccc      900 aacggcagca tccccaacga caagcccttc cagaacgtga acaagatcac ctacggggcc      960
tgtcctaagt acgtgaagca gaacaccctg aagctcgcta ccggcatgcg gaacgtgccc     1020
gagaagcaga ccaggggcct gttcggggcc atcgccggct tcatcgagaa cggctgggag     1080
ggcatgatcg acgggtggta tggcttccgc caccagaaca gcgagggcac cggccaggcc     1140
gccgacctga agagcaccca ggccgccatc gaccagatca cggcaagct gaaccgcgtg     1200 atcgagaaaa ccaacgagaa gttccaccag atcgagaaag agttcagcga ggtcgagggc     1260
cgcatccagg acctggagaa gtacgtggag gacaccaaga tcgacctgtg gagctacaac     1320
gccgagctgc tggtcgccct ggagaaccag cacaccatcg acctgaccga cagcgagatg     1380
aacaagctgt tcgagaaaac ccgcaggcag ctgcgcgaga cgccgagga catgggcaac     1440 ggctgcttca agatctacca caagtgcgac aacgcctgca tcgagagcat ccgcaacggc     1500
```

-continued

```
acctacgacc acgacgtgta ccgcgacgag gccctgaaca accgcttcca gatcaagggc    1560
gtggagctga agagcggcta caaggactgg atcctgtgga tcagcttcgc tatcagctgc    1620
ttcctgctgt gcgtggtgct gctgggcttc atcatgtggg cctgccagcg gggcaacatc    1680
cgctgcaaca tctgcatc                                                  1698
```

<210> SEQ ID NO 13
<211> LENGTH: 566
<212> TYPE: PRT
<213> ORGANISM: Influenza A virus

<400> SEQUENCE: 13

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Glu Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335
```

```
Arg Asn Val Pro Glu Lys Gln Thr Arg Gly Leu Phe Gly Ala Ile Ala
                340                 345                 350
Gly Phe Ile Glu Asn Gly Trp Glu Gly Met Ile Asp Gly Trp Tyr Gly
            355                 360                 365
Phe Arg His Gln Asn Ser Glu Gly Thr Gly Gln Ala Ala Asp Leu Lys
        370                 375                 380
Ser Thr Gln Ala Ala Ile Asp Gln Ile Asn Gly Lys Leu Asn Arg Val
385                 390                 395                 400
Ile Glu Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Asn Lys Leu Phe
        450                 455                 460
Glu Lys Thr Arg Arg Gln Leu Arg Glu Asn Ala Glu Asp Met Gly Asn
465                 470                 475                 480
Gly Cys Phe Lys Ile Tyr His Lys Cys Asp Asn Ala Cys Ile Glu Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
530                 535                 540
Val Val Leu Leu Gly Phe Ile Met Trp Ala Cys Gln Arg Gly Asn Ile
545                 550                 555                 560
Arg Cys Asn Ile Cys Ile
                565

<210> SEQ ID NO 14
<211> LENGTH: 1407
<212> TYPE: DNA
<213> ORGANISM: Influenza A virus

<400> SEQUENCE: 14
atgaacccca accagaagat catcaccatc ggcagcgtgt gcatgaccat cggcatggcc      60
aacctgatcc tgcagatcgg caacatcatc agcatctgga tcagccacag catccagctg     120
ggcaaccaga accagatcga catgcaac cagagcgtga tcacctacga gaacaacacc       180
tgggtgaacc agacctacgt gaacatcagc aacaccaact cgccgctgg ccagagcgtg      240
gtgtctgtga gctggccgg caacagcagc ctgtgccctg tgtccggctg ggccatctac      300
agcaaggaca cagcgtgcg gatcggcagc aagggcgacg tgttcgtgat ccgggagccc      360
ttcatcagct gcagccccct ggaatgccgg accttcttcc tgacccaggg ggccctgctg     420
aacgacaagc acagcaacgg caccatcaag acagaagcc cctaccggac cctgatgagc     480
tgccccatcg cgaggtgcc cagcccctac aacagcagat cgagtccgt ggcttggagc      540
gcctctgcct gcacgacgg catcaactgg ctgacaatcg catcagcgg ccctgataac      600
ggcgctgtgg ccgtgctgaa gtacaacggc atcatcaccg acacaatcaa gagctggcgg    660
aacaacatcc tgcggaccca ggaatccgag tgcgcctgcg tgaacggcag ctgcttcacc    720
gtgatgaccg acggccctag caatggccag gccagctaca gatcttccg gatcgagaag    780
```

```
ggcaagatcg tgaagtccgt ggagatgaac gcccccaact accactacga ggaatgcagc    840
tgctaccccg acagcagcga gatcacctgt gtgtgccggg acaactggca cggcagcaac    900
agaccctggg tgtccttcaa ccagaatctg gaataccaga tcggctacat ttgcagcggc    960
atcttcggcg acaaccccag acccaacgac aagaccggaa gctgcggccc tgtgtctagc   1020
aacggggcca acggcgtgaa gggcttcagc ttcaagtacg gcaatggcgt gtggatcggc   1080
cggaccaaga gcatcagcag ccggaacggc ttcgagatga tctgggaccc caacggctgg   1140
accggcaccg acaacaactt cagcatcaag caggacatcg tgggcatcaa cgagtggagc   1200
ggctacagcg gcagcttcgt gcagcaccct gagctgaccg gcctggactg catccggccc   1260
tgcttttggg tggagctgat cagaggcaga cccaaagaga caccatctg gaccagcggc    1320 agcagcatca gcttttgcgg cgtgaacagc gacaccgtgg gctggtcttg gcccgatggg   1380
gccgagctgc ccttcaccat cgacaag                                       1407
```

<210> SEQ ID NO 15
<211> LENGTH: 469
<212> TYPE: PRT
<213> ORGANISM: Influenza A virus

<400> SEQUENCE: 15

```
Met Asn Pro Asn Gln Lys Ile Ile Thr Ile Gly Ser Val Cys Met Thr
 1               5                  10                  15

Ile Gly Met Ala Asn Leu Ile Leu Gln Ile Gly Asn Ile Ile Ser Ile
                20                  25                  30

Trp Ile Ser His Ser Ile Gln Leu Gly Asn Gln Asn Gln Ile Glu Thr
            35                  40                  45

Cys Asn Gln Ser Val Ile Thr Tyr Glu Asn Asn Thr Trp Val Asn Gln
        50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255
```

```
Arg Ile Glu Lys Gly Lys Ile Val Lys Ser Val Met Asn Ala Pro
            260                 265                 270

Asn Tyr His Tyr Glu Glu Cys Ser Cys Tyr Pro Asp Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
                340                 345                 350

Tyr Gly Asn Gly Val Trp Ile Gly Arg Thr Lys Ser Ile Ser Ser Arg
            355                 360                 365

Asn Gly Phe Glu Met Ile Trp Asp Pro Asn Gly Trp Thr Gly Thr Asp
        370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465

<210> SEQ ID NO 16
<211> LENGTH: 1407
<212> TYPE: DNA
<213> ORGANISM: Influenza A virus

<400> SEQUENCE: 16
atgaacccca accagaagat catcaccatc ggcagcgtga gcctgacaat cgctaccgtg     60
tgcttcctga tgcagatcgc catcctggtg accaccgtga ccctgcactt caagcagtac    120
gagtgcgaca gccccgccag caaccaggtc atgccctgcg agcccatcat catcgagcgc    180
aacatcaccg agatcgtgta cctgaacaac accaccatcg agaaggaaat ctgccccaag    240
gtcgtggagt accgcaactg gtccaagccc cagtgccaga tcaccggctt cgccccttc     300
agcaaggaca cagcatccg cctgagcgcc ggagggaca tctgggtcac ccgcgagccc      360
tacgtgagct gcgaccacgg caagtgctac cagttcgctc tggggcaggg gacaacactc    420
gataacaagc acagcaacga caccatccac gaccgcatcc ccaccgcac cctgctgatg     480
aacgagctgg gcgtgcccct ccacctgggc acccgccagg tctgcatcgc ctggtccagc    540
agcagctgcc acgacggcaa ggcctggctg cacgtgtgca tcaccggcga cgacaagaac    600
gccaccgcca gcttcatcta cgacggccgc ctggtggaca gcatcggcag ctggtcccag    660
aacatcctgc gcacccaaga aagcgagtgc gtctgcatca acgggacctg caccgtggtg    720
atgaccgatg gaagcgccag cggcagggcc gatacccgga tcctgttcat cgaggaaggc    780
aagatcgtgc acatcagccc tctcagcggc tccgcccagc acgtggaaga gtgcagctgc    840
```

-continued

```
taccccccgct accccggcgt gcgctgcatc tgccgcgaca actggaaggg cagcaaccgc    900
cccgtggtgg acatcaacat ggaggactac agcatcgaca gcagctacgt gtgcagcggc    960
ctggtcggcg acacaccccg caacgacgac cgcagcagca acagcaactg ccgcaacccc   1020
aacaacgagc gcggcaacca gggcgtgaag ggctgggcct tcgacaacgg cgacgacgtg   1080
tggatgggcc gcaccatctc caaggacctg cgcagcggct acgagacctt caaggtgatc   1140
ggcgggtgga gcacccccaa cagcaagagc cagatcaacc gccaggtgat cgtggacagc   1200
gacaaccgct ccggctacag cggcatcttc agcgtggagg gcaagtcctg catcaaccgc   1260
tgcttctacg tggagctgat ccgcggcagg aagcaagaaa cccgcgtctg gtggaccagc   1320
aactccatcg tggtgttctg cggcaccagc ggcacctacg gcaccggcag ctggcccgac   1380
ggggccaaca tcaacttcat gcccatc                                       1407
```

```

<210> SEQ ID NO 17
<211> LENGTH: 469
<212> TYPE: PRT
<213> ORGANISM: Influenza A virus

<400> SEQUENCE: 17

Met Asn Pro Asn Gln Lys Ile Ile Thr Ile Gly Ser Val Ser Leu Thr
1               5                   10                  15

Ile Ala Thr Val Cys Phe Leu Met Gln Ile Ala Ile Leu Val Thr Thr
            20                  25                  30

Val Thr Leu His Phe Lys Gln Tyr Glu Cys Asp Ser Pro Ala Ser Asn
        35                  40                  45

Gln Val Met Pro Cys Glu Pro Ile Ile Ile Glu Arg Asn Ile Thr Glu
    50                  55                  60

Ile Val Tyr Leu Asn Asn Thr Thr Ile Glu Lys Glu Ile Cys Pro Lys
65                  70                  75                  80

Val Val Glu Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp His Gly Lys
        115                 120                 125

Cys Tyr Gln Phe Ala Leu Gly Gln Gly Thr Thr Leu Asp Asn Lys His
    130                 135                 140

Ser Asn Asp Thr Ile His Asp Arg Ile Pro His Arg Thr Leu Leu Met
145                 150                 155                 160

Asn Glu Leu Gly Val Pro Phe His Leu Gly Thr Arg Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asp
        195                 200                 205

Gly Arg Leu Val Asp Ser Ile Gly Ser Trp Ser Gln Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Glu Glu Gly Lys Ile Val His Ile Ser Pro Leu Ser Gly Ser Ala
            260                 265                 270
```

```
Gln His Val Glu Glu Cys Ser Cys Tyr Pro Arg Tyr Pro Gly Val Arg
        275                 280                 285

Cys Ile Cys Arg Asp Asn Trp Lys Gly Ser Asn Arg Pro Val Val Asp
    290                 295                 300

Ile Asn Met Glu Asp Tyr Ser Ile Asp Ser Ser Tyr Val Cys Ser Gly
305                 310                 315                 320

Leu Val Gly Asp Thr Pro Arg Asn Asp Arg Ser Asn Ser Asn
                325                 330                 335

Cys Arg Asn Pro Asn Asn Glu Arg Gly Asn Gln Gly Val Lys Gly Trp
                340                 345                 350

Ala Phe Asp Asn Gly Asp Asp Val Trp Met Gly Arg Thr Ile Ser Lys
        355                 360                 365

Asp Leu Arg Ser Gly Tyr Glu Thr Phe Lys Val Ile Gly Gly Trp Ser
    370                 375                 380

Thr Pro Asn Ser Lys Ser Gln Ile Asn Arg Gln Val Ile Val Asp Ser
385                 390                 395                 400

Asp Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
                420                 425                 430

Glu Thr Arg Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asn Ile
        450                 455                 460

Asn Phe Met Pro Ile
465

<210> SEQ ID NO 18
<211> LENGTH: 1494
<212> TYPE: DNA
<213> ORGANISM: Influenza A virus

<400> SEQUENCE: 18
atggccagcc agggcaccaa gagaagctac gagcagatgg aaaccgacgg cgagaggcag      60
aacgccaccg agatcagggc cagcgtgggc aggatgatcg gcggcatcgg caggttctac     120
atccagatgt gcaccgagct gaagctgtcc gactacgagg caggctgat ccagaacagc      180 atcaccatcg agaggatggt gctgtccgcc ttcgacgaga agaaacaa gtacctggaa       240 gagcacccca gcgccggcaa ggaccccaag aaaaccggcg acccatcta cagaaggatc      300 gacggcaagt ggatgagaga gctgatcctg tacgacaagg aggaaatcag aaggatctgg     360
cggcaggcca caacggcga ggacgccaca gccggcctga cccacatgat gatctggcac     420
agcaacctga cgacgccac ctaccagagg accaggccc tcgtcagaac cggcatggac      480
ccccggatgt gcagcctgat gcagggcagc acactgccca agaagcgg agctgctgga      540 gccgccgtga agggcgtggg caccatggtg atggaactga tcaggatgat caagaggggc     600
atcaacgaca ggaacttttg gaggggcgag aacggcagaa ggaccaggat cgcctacgag     660
aggatgtgca acatcctgaa gggcaagttc cagacagccg cccagagggc catgatggac     720
caggtccggg agagcaggaa ccccggcaac gccgagatcg aggacctgat cttcctggcc     780
agaagcgccc tgatcctgag gggcagcgtg gcccacaaga gctgcctgcc cgcctgcgtg     840
tacggacccg ccgtgccag cggctacgac ttcgagagag agggctacag cctggtcggc     900 atcgaccct tcaggctgct gcagaactcc caggtgtact ctctgatcag gcccaacgag     960
```

-continued

```
aaccccgccc acaagtccca gctggtctgg atggcctgcc acagcgccgc cttcgaggat    1020
ctgagagtga gcagcttcat caggggcacc agagtggtgc ccaggggcaa gctgtccacc    1080
aggggcgtgc agatcgccag caacgagaac atggaaacca tggacagcag caccctggaa    1140
ctgagaagca ggtactgggc catcaggacc agaagcggcg caacaccaa ccagcagagg     1200 gccagcgccg acagatcag cgtgcagccc accttctccg tgcaggaa  cctgcccttc      1260 gagagggcca ccatcatggc cgccttcacc ggcaacaccg agggcaggac cagagacatg    1320
aggaccgaga tcatcagaat gatggaaagc gccaggcccg aggacgtgag cttccagggc    1380
aggggcgtgt cgagctgtc cgatgagaag gccacctccc ccatcgtgcc cagcttcgac     1440
atgagcaacg agggcagcta cttcttcggc gacaacgccg aggaatacga caac          1494
```

<210> SEQ ID NO 19
<211> LENGTH: 498
<212> TYPE: PRT
<213> ORGANISM: Influenza A virus

<400> SEQUENCE: 19

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Ile Asp Gly Lys Trp Met Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285
```

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
                340                 345                 350

Val Pro Arg Gly Lys Leu Ser Thr Arg Gly Val Gln Ile Ala Ser Asn
            355                 360                 365

Glu Asn Met Glu Thr Met Asp Ser Ser Thr Leu Glu Leu Arg Ser Arg
370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
                420                 425                 430

Thr Glu Gly Arg Thr Arg Asp Met Arg Thr Glu Ile Ile Arg Met Met
            435                 440                 445

Glu Ser Ala Arg Pro Glu Asp Val Ser Phe Gln Gly Arg Gly Val Phe
450                 455                 460

Glu Leu Ser Asp Glu Lys Ala Thr Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 20
<211> LENGTH: 1494
<212> TYPE: DNA
<213> ORGANISM: Influenza A virus

<400> SEQUENCE: 20
atggccagcc agggcaccaa gagaagctac gagcagatgg aaaccgacgg cgagaggcag      60
aacgccaccg agatcagggc cagcgtgggc aggatgatcg gcggcatcgg caggttctac     120
atccagatgt gcaccgagct gaagctgtcc gactacgagg caggctgat ccagaacagc      180 atcaccatcg agaggatggt gctgtccgcc ttcgacgaga agaaacaa gtacctggaa       240 gagcacccca gcgccggcaa ggaccccaag aaaaccggcg acccatcta cagaaggatc      300 gacggcaagt ggatgagaga gctgatcctg tgggagaagg acgacatcaa gcggatctac     360
aagcaggcca acaacggcga ggacgccaca gccggcctga cccacatgat gatctggcac     420
agcaacctga cgacgccac ctaccagagg accagggccc tcgtcagaac cggcatggac      480 cccggatgt gcagcctgat gcaggcagc acactgccca agaagcgg agctgctgga        540 gccgccgtga agggcgtggg caccatggtg atggaactga tcaggatgat caagaggggc     600
atcaacgaca ggaactttg gaggggcgag aacggcagaa ggaccaggat cgcctacgag      660
aggatgtgca acatcctgaa gggcaagttc cagacagccg cccagagggc catgatggac     720
caggtccggg agagcaggaa ccccggcaac gccgagatcg aggacctgat cttcctggcc     780
agaagcgccc tgatcctgag gggcagcgtg gcccacaaga gctgcctgcc cgcctgcgtg     840
tacggacccg ccgtggccag cggctacgac ttcgagagag agggctacag cctggtcggc     900

-continued

```
atcgacccct tcaggctgct gcagaactcc caggtgtact ctctgatcag gcccaacgag    960
aaccccgccc acaagtccca gctggtctgg atggcctgcc acagcgccgc cttcgaggat   1020
ctgagagtga gcagcttcat caggggcacc agagtggtgc ccaggggcaa gctgtccacc   1080
aggggcgtgc agatcgccag caacgagaac atggaaacca tggacagcag caccctggaa   1140
ctgagaagca ggtactgggc catcaggacc agaagcggcg gcaacaccaa ccagcagagg   1200
gccagcgccg gacagatcag cgtgcagccc accttctccg tgcagaggaa cctgcccttc   1260
gagagggcca ccatcatggc cgccttcacc ggcaacaccg agggcaggac cagagacatg   1320
aggaccgaga tcatcagaat gatggaaagc gccaggcccg aggacgtgag cttccagggc   1380
aggggcgtgt tcgagctgtc cgatgagaag gccacctccc ccatcgtgcc cagcttcgac   1440
atgagcaacg agggcagcta cttcttcggc gacaacgccg aggaatacga caac         1494
```

<210> SEQ ID NO 21
<211> LENGTH: 498
<212> TYPE: PRT
<213> ORGANISM: Influenza A virus

<400> SEQUENCE: 21

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Ile Asp Gly Lys Trp Met Arg Glu Leu Ile Leu Trp Glu
            100                 105                 110

Lys Asp Asp Ile Lys Arg Ile Tyr Lys Gln Ala Asn Asn Gly Glu Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270
```

```
Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
        290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Lys Leu Ser Thr Arg Gly Val Gln Ile Ala Ser Asn
        355                 360                 365

Glu Asn Met Glu Thr Met Asp Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Arg Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Thr Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 22
<211> LENGTH: 756
<212> TYPE: DNA
<213> ORGANISM: Influenza A virus

<400> SEQUENCE: 22
atgtccctgc tgacagaggt ggagacctac gtgctgtcca tcgtgccctc tggccctctg      60
aaggccgaga tcgcccagag actggaggac gtgttcgccg gcaagaacac agatctggag     120
gccctgatgg agtggctgaa gacaaggcca atcctgtctc ccctgaccaa ggcatcctg      180 ggcttcgtgt ttacactgac cgtgcctagc gagagggac tgcagcggag aaggttcgtg      240
cagaatgccc tgaacggcaa tggcgaccca aacaatatgg atcgggccgt gaagctgtat     300
agaaagctga gagggagat cacctttcac ggagccaagg aggtggccct gtcttacagc      360
gccggggccc tggcaagctg catgggactg atctataaca ggatgggcac agtgaccaca     420
gaggtggcct tcggcctggt gtgcgcaacc tgtgagcaga tcgcagacag ccagcaccgc     480
tcccacaggc agatggtgac acaaccaac ccctgatcc gccacgagaa tcggatggtg       540
ctggcctcca caaccgccaa ggccatggag cagatggcag cagctccga gcaggcagca     600 gaggccatgg aggtggcctc tcaggccaga cagatggtgc aggccatgag acaatcgga     660 acccacccctt ctagctccgc cggcctgaag gacgatctga tcgagaatct gcaggcctac    720
cagaagcgca tgggcgtgca gatgcagcgg tttaag                               756
```

```
<210> SEQ ID NO 23
<211> LENGTH: 252
<212> TYPE: PRT
<213> ORGANISM: Influenza A virus

<400> SEQUENCE: 23

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Ala Gly Ala Leu Ala Ser Cys Met
        115                 120                 125

Gly Leu Ile Tyr Asn Arg Met Gly Thr Val Thr Thr Glu Val Ala Phe
130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
210                 215                 220

Ser Ser Ala Gly Leu Lys Asp Asp Leu Ile Glu Asn Leu Gln Ala Tyr
225                 230                 235                 240

Gln Lys Arg Met Gly Val Gln Met Gln Arg Phe Lys
                245                 250

<210> SEQ ID NO 24
<211> LENGTH: 291
<212> TYPE: DNA
<213> ORGANISM: Influenza A virus

<400> SEQUENCE: 24
atgtccctgc tgaccgaggt ggagacccca acacggaacg agtggggctg cagatgtaat      60
gacagctccg atccctggt catcgccgcc tctatcatcg gcatcctgca cctgatcctg      120
tggatcctgg acaggctgtt ctttaagtgc atctaccgga gactgaagta tggcctgaag      180
agaggcccct ctacagaggg cgtgcctgag agcatgaggg aggagtaccg caaggagcag      240
cagagcgccg tggatgtgga cgatggccac ttcgtgaaca tcgagctgga g              291

<210> SEQ ID NO 25
<211> LENGTH: 97
<212> TYPE: PRT
<213> ORGANISM: Influenza A virus
```

```
<400> SEQUENCE: 25

Met Ser Leu Leu Thr Glu Val Glu Thr Pro Thr Arg Asn Glu Trp Gly
1               5                   10                  15

Cys Arg Cys Asn Asp Ser Ser Asp Pro Leu Val Ile Ala Ala Ser Ile
            20                  25                  30

Ile Gly Ile Leu His Leu Ile Leu Trp Ile Leu Asp Arg Leu Phe Phe
        35                  40                  45

Lys Cys Ile Tyr Arg Arg Leu Lys Tyr Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Ser Ala Val Asp Val Asp Asp Gly His Phe Val Asn Ile Glu Leu
                85                  90                  95

Glu

<210> SEQ ID NO 26
<211> LENGTH: 24
<212> TYPE: PRT
<213> ORGANISM: Porcine hemagglutinating encephalomyelitis coronavirus

<400> SEQUENCE: 26

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 27
<211> LENGTH: 19
<212> TYPE: PRT
<213> ORGANISM: Porcine hemagglutinating encephalomyelitis coronavirus

<400> SEQUENCE: 27

Ala Thr Asn Phe Ser Leu Leu Lys Gln Ala Gly Asp Val Glu Glu Asn
1               5                   10                  15

Pro Gly Pro

<210> SEQ ID NO 28
<211> LENGTH: 20
<212> TYPE: PRT
<213> ORGANISM: Porcine hemagglutinating encephalomyelitis coronavirus

<400> SEQUENCE: 28

Gln Cys Thr Asn Tyr Ala Leu Leu Lys Leu Ala Gly Asp Val Glu Ser
1               5                   10                  15

Asn Pro Gly Pro
            20

<210> SEQ ID NO 29
<211> LENGTH: 18
<212> TYPE: PRT
<213> ORGANISM: Porcine hemagglutinating encephalomyelitis coronavirus

<400> SEQUENCE: 29

Glu Gly Arg Gly Ser Leu Leu Thr Cys Gly Asp Val Glu Glu Asn Pro
1               5                   10                  15

Gly Pro

<210> SEQ ID NO 30
```

```
<211> LENGTH: 6
<212> TYPE: DNA
<213> ORGANISM: Artificial Sequence
<220> FEATURE:
<223> OTHER INFORMATION: Kozak sequence

<400> SEQUENCE: 30 gccacc                                                              6

<210> SEQ ID NO 31
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 31

Arg Xaa Arg Arg
1

<210> SEQ ID NO 32
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 32

Arg Xaa Lys Arg
1

<210> SEQ ID NO 33
<211> LENGTH: 7
<212> TYPE: PRT
<213> ORGANISM: Influenza A virus

<400> SEQUENCE: 33

His Asp Ser Asn Lys Gly Val
1               5

<210> SEQ ID NO 34
<211> LENGTH: 7
<212> TYPE: PRT
<213> ORGANISM: Artificial Sequence
<220> FEATURE:
<223> OTHER INFORMATION: altered HA (H1N1) amino acid sequence

<400> SEQUENCE: 34

His Asp Ser Asp Lys Gly Val
1               5

<210> SEQ ID NO 35
<211> LENGTH: 11
<212> TYPE: PRT
<213> ORGANISM: Influenza A virus

<400> SEQUENCE: 35

Tyr Asp Lys Glu Glu Ile Arg Arg Ile Trp Arg
1               5                   10
```

```
<210> SEQ ID NO 36
<211> LENGTH: 11
<212> TYPE: PRT
<213> ORGANISM: Artificial Sequence
<220> FEATURE:
<223> OTHER INFORMATION: altered NP(H1N1) epitope sequence

<400> SEQUENCE: 36

Trp Glu Lys Asp Asp Ile Lys Arg Ile Tyr Lys
1               5                   10

<210> SEQ ID NO 37
<211> LENGTH: 11
<212> TYPE: DNA
<213> ORGANISM: Artificial Sequence
<220> FEATURE:
<223> OTHER INFORMATION: termination sequence

<400> SEQUENCE: 37
tgactagtta a                                                          11
```